(12) United States Patent
Siddiqui-Jain et al.

(10) Patent No.: US 11,279,694 B2
(45) Date of Patent: Mar. 22, 2022

(54) ALVOCIDIB PRODRUGS AND THEIR USE AS PROTEIN KINASE INHIBITORS

(71) Applicant: Sumitomo Dainippon Pharma Oncology, Inc., Cambridge, MA (US)

(72) Inventors: Adam Siddiqui-Jain, South Jordan, UT (US); Yusuke Sawayama, Osaka (JP); Wataru Hirose, Osaka (JP); Hitoshi Ban, Hyogo (JP)

(73) Assignee: Sumitomo Dainippon Pharma Oncology, Inc., Cambridge, MA (US)

( * ) Notice: Subject to any disclaimer, the term of this patent is extended or adjusted under 35 U.S.C. 154(b) by 0 days.

(21) Appl. No.: 16/462,094

(22) PCT Filed: Nov. 17, 2017

(86) PCT No.: PCT/US2017/062408
§ 371 (c)(1),
(2) Date: May 17, 2019

(87) PCT Pub. No.: WO2018/094275
PCT Pub. Date: May 24, 2018

(65) Prior Publication Data
US 2020/0048228 A1 Feb. 13, 2020

Related U.S. Application Data

(60) Provisional application No. 62/424,255, filed on Nov. 18, 2016.

(51) Int. Cl.
| | | |
|---|---|---|
| *C07D 405/04* | (2006.01) | |
| *C07F 9/6558* | (2006.01) | |
| *C07F 9/6574* | (2006.01) | |
| *C07F 9/6584* | (2006.01) | |

(52) U.S. Cl.
CPC ........ *C07D 405/04* (2013.01); *C07F 9/65586* (2013.01); *C07F 9/65742* (2013.01); *C07F 9/65844* (2013.01)

(58) Field of Classification Search
CPC .................................................. C07D 405/04
USPC ....................................................... 549/399
See application file for complete search history.

(56) References Cited

U.S. PATENT DOCUMENTS

| | | |
|---|---|---|
| 4,132,710 A | 1/1979 | Gauthier et al. |
| 4,146,629 A | 3/1979 | Kubel et al. |
| 4,522,811 A | 6/1985 | Eppstein et al. |
| 4,676,980 A | 6/1987 | Segal et al. |
| 4,816,567 A | 3/1989 | Cabilly et al. |
| 4,900,727 A | 2/1990 | Kattige et al. |
| 4,946,778 A | 8/1990 | Ladner et al. |
| 4,971,909 A | 11/1990 | Kaneoya et al. |
| 5,225,539 A | 7/1993 | Winter |
| 5,284,856 A | 2/1994 | Naik et al. |
| 5,310,763 A | 5/1994 | Campion et al. |
| 5,545,806 A | 8/1996 | Lonberg et al. |
| 5,545,807 A | 8/1996 | Surani et al. |
| 5,569,825 A | 10/1996 | Lonberg et al. |
| 5,587,458 A | 12/1996 | King et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,674,980 A | 10/1997 | Frankel et al. |
| 5,747,498 A | 5/1998 | Schnur et al. |
| 5,792,783 A | 8/1998 | Tang et al. |
| 5,804,604 A | 9/1998 | Frankel et al. |

(Continued)

FOREIGN PATENT DOCUMENTS

| | | |
|---|---|---|
| CN | 1583776 A | 2/2005 |
| CN | 105919955 A | 9/2016 |

(Continued)

OTHER PUBLICATIONS

Venkatesh, J. Pharm. Sci. 89, 145-54 (2000) (p. 146, left column).*
Wolff, Burger's medicinal Chemistry and Drug Discovery, vol. 1, Principles and Practice, John Wiley & sons, New York, 1997.*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Linenberger, Biochemistry and Molecular Biology Education, 2014, 203-212.*
Burnette, Antiviral Chemistry & Chemotherapy (1992) 3(3), 157-164.*
Férriz, Current Pharmaceutical Design, 2010, 16, 2033-2052.*
Jornada, Molecules 2016, 21, 42, 1-31.*
Bundgard, H., Design of Prodrugs (1985), pp. 7-9, 21-24 (Elsevier, Amsterdam).*

(Continued)

*Primary Examiner* — Nizal S Chandrakumar
(74) *Attorney, Agent, or Firm* — Hamilton, Brook, Smith & Reynolds, P.C.

(57) ABSTRACT

Compounds having the following structure (I) or a stereoisomer, tautomer or pharmaceutically acceptable salt thereof, wherein $R^1$, $R^2$ and $R^3$ are as defined herein, and wherein at least one of $R^1$, $R^2$ and $R^3$ is not H, are provided. Pharmaceutical compositions comprising the compounds and methods for use of the compounds for treating diseases associated with overexpression of a cyclin-dependent kinase (CDK) are also provided.

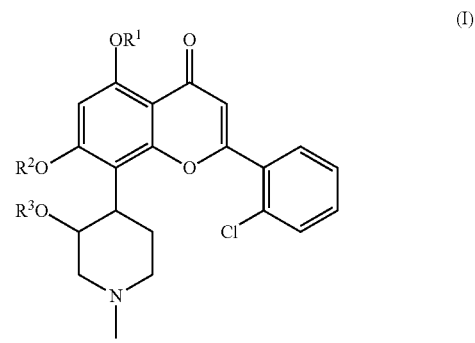

(I)

4 Claims, 3 Drawing Sheets

(56) References Cited

U.S. PATENT DOCUMENTS

| | | | |
|---|---|---|---|
| 5,834,504 | A | 11/1998 | Tang et al. |
| 5,849,733 | A | 12/1998 | Kim |
| 5,861,510 | A | 1/1999 | Piscopio et al. |
| 5,863,949 | A | 1/1999 | Robinson et al. |
| 5,877,305 | A | 3/1999 | Huston et al. |
| 5,883,113 | A | 3/1999 | Tang et al. |
| 5,886,020 | A | 3/1999 | Tang et al. |
| 5,908,934 | A | 6/1999 | Kim |
| 5,916,771 | A | 6/1999 | Hori et al. |
| 5,932,595 | A | 8/1999 | Bender et al. |
| 5,939,598 | A | 8/1999 | Kucherlapati et al. |
| 5,965,703 | A | 10/1999 | Horne et al. |
| 6,077,864 | A | 6/2000 | Burgess et al. |
| 6,087,366 | A | 7/2000 | Park et al. |
| 6,087,392 | A | 7/2000 | Reiter |
| 6,090,852 | A | 7/2000 | Dack et al. |
| 6,110,964 | A | 8/2000 | Robinson |
| 6,136,981 | A | 10/2000 | Brion et al. |
| 6,147,061 | A | 11/2000 | Reiter |
| 6,153,609 | A | 11/2000 | Robinson et al. |
| 6,177,401 | B1 | 1/2001 | Ullrich et al. |
| 6,207,669 | B1 | 3/2001 | Cockerill et al. |
| 6,214,872 | B1 | 4/2001 | Robinson |
| 6,225,473 | B1 | 5/2001 | Breipohl et al. |
| 6,258,540 | B1 | 7/2001 | Lo et al. |
| 6,284,764 | B1 | 9/2001 | Kath et al. |
| 6,291,455 | B1 | 9/2001 | Thomas et al. |
| 6,294,532 | B1 | 9/2001 | Thomas et al. |
| 6,303,636 | B1 | 10/2001 | Robinson, Jr. et al. |
| 6,362,336 | B1 | 3/2002 | Lohmann et al. |
| 6,399,633 | B1 | 6/2002 | Breipohl et al. |
| 6,406,912 | B1 | 6/2002 | Holla |
| 6,437,136 | B2 | 8/2002 | Breipohl et al. |
| 6,492,383 | B1 | 12/2002 | Munchhof et al. |
| 6,495,568 | B1 | 12/2002 | Dack et al. |
| 6,511,993 | B1 | 1/2003 | Dack et al. |
| 6,576,647 | B2 | 6/2003 | Bafus et al. |
| 6,587,123 | B2 | 7/2003 | Ando et al. |
| 6,596,726 | B1 | 7/2003 | Bridges et al. |
| 6,599,890 | B1 | 7/2003 | McClure et al. |
| 6,723,726 | B1 | 4/2004 | Cockerill et al. |
| 6,821,990 | B2 | 11/2004 | Kesseler |
| 6,828,320 | B2 | 12/2004 | Cockerill et al. |
| 6,849,631 | B2 | 2/2005 | Carini |
| 7,064,193 | B1 | 6/2006 | Cory et al. |
| 7,119,090 | B2 | 10/2006 | Tang et al. |
| 7,332,582 | B2 | 2/2008 | Hardy et al. |
| 7,417,055 | B2 | 8/2008 | Cannizzaro et al. |
| 7,452,901 | B2 | 11/2008 | Boojamra et al. |
| 7,488,802 | B2 | 2/2009 | Collins et al. |
| 7,572,924 | B2 | 8/2009 | Tang et al. |
| 7,695,715 | B2 | 4/2010 | Hardy et al. |
| 7,714,005 | B2 | 5/2010 | Chen et al. |
| 7,790,902 | B2 | 9/2010 | Larson et al. |
| 7,816,398 | B2 * | 10/2010 | Swindell ............ A61P 3/10 514/449 |
| 7,829,662 | B2 | 11/2010 | Korsmeyer et al. |
| 7,868,133 | B2 | 1/2011 | Korsmeyer et al. |
| 7,884,127 | B2 | 2/2011 | Lal et al. |
| 7,943,743 | B2 | 5/2011 | Korman et al. |
| 8,008,449 | B2 | 8/2011 | Korman et al. |
| 8,168,179 | B2 | 5/2012 | Honjo et al. |
| 8,168,755 | B2 | 5/2012 | Cardone et al. |
| 8,217,149 | B2 | 7/2012 | Irving et al. |
| 8,221,966 | B2 | 7/2012 | Letai |
| 8,304,449 | B2 * | 11/2012 | Lal ............ A61P 35/00 514/422 |
| 8,354,509 | B2 | 1/2013 | Craven et al. |
| 8,372,819 | B2 | 2/2013 | Jones et al. |
| 8,460,927 | B2 | 6/2013 | Chen |
| 8,552,154 | B2 | 10/2013 | Freeman et al. |
| 8,552,156 | B2 | 10/2013 | Takayanagi et al. |
| 8,686,119 | B2 | 4/2014 | Roten-Yehudar et al. |
| 8,735,553 | B1 | 5/2014 | Li et al. |
| 8,758,752 | B2 | 6/2014 | Govindan et al. |
| 8,779,108 | B2 | 7/2014 | Queva et al. |
| 8,822,526 | B2 | 9/2014 | Rathos et al. |
| 8,841,418 | B2 | 9/2014 | Karsunky et al. |
| 8,907,053 | B2 | 12/2014 | Sasikumar et al. |
| 8,927,697 | B2 | 1/2015 | Davis et al. |
| 8,975,239 | B2 | 3/2015 | Green et al. |
| 8,993,731 | B2 | 3/2015 | Tyson |
| 9,102,727 | B2 | 8/2015 | Freeman et al. |
| 9,138,485 | B2 | 9/2015 | Govindan et al. |
| 9,163,087 | B2 | 10/2015 | Kuchroo et al. |
| 9,175,082 | B2 | 11/2015 | Zhou et al. |
| 9,199,973 | B2 | 12/2015 | Carter et al. |
| 9,205,148 | B2 | 12/2015 | Langermann et al. |
| 9,241,941 | B2 | 1/2016 | Wendel et al. |
| 9,244,059 | B2 | 1/2016 | Triebel et al. |
| 9,340,524 | B2 | 5/2016 | Chen et al. |
| 9,360,473 | B2 | 6/2016 | Cardone |
| 9,493,454 | B2 | 11/2016 | Zeng et al. |
| 9,505,839 | B2 | 11/2016 | Lonberg et al. |
| 9,540,674 | B2 | 1/2017 | Letai |
| 9,605,070 | B2 | 3/2017 | Seabatos-Peyton et al. |
| 9,683,048 | B2 | 6/2017 | Freeman et al. |
| 9,758,539 | B2 * | 9/2017 | Siddiqui-Jain ...... C07F 9/65586 |
| 9,856,303 | B2 | 1/2018 | Korsmeyer et al. |
| 9,901,574 | B2 | 2/2018 | Warner et al. |
| 9,902,759 | B2 | 2/2018 | Korsmeyer et al. |
| 9,925,192 | B2 | 3/2018 | Strack et al. |
| 9,988,452 | B2 | 6/2018 | Freeman et al. |
| 10,132,797 | B2 | 11/2018 | Bearss et al. |
| 10,259,835 | B2 | 4/2019 | Siddiqui-Jain et al. |
| 10,267,787 | B2 | 4/2019 | Bearss et al. |
| 10,357,488 | B2 | 7/2019 | Warner et al. |
| 10,422,788 | B2 | 9/2019 | Bearss et al. |
| 10,562,925 | B2 | 2/2020 | Siddiqui-Jain et al. |
| 10,568,887 | B2 | 2/2020 | Bearss et al. |
| 10,624,880 | B2 | 4/2020 | Warner et al. |
| 10,682,356 | B2 | 6/2020 | Bearss et al. |
| 10,793,915 | B2 | 10/2020 | Dettman et al. |
| 10,835,537 | B2 | 11/2020 | Bearss et al. |
| 11,034,710 | B2 | 6/2021 | Siddiqui-Jain et al. |
| 2001/0021704 | A1 | 9/2001 | Ghyczy et al. |
| 2002/0016293 | A1 | 2/2002 | Ratain et al. |
| 2002/0115613 | A1 | 8/2002 | Kumar |
| 2002/0177609 | A1 | 11/2002 | Swindell et al. |
| 2003/0065023 | A1 | 4/2003 | Swindell et al. |
| 2003/0073661 | A1 | 4/2003 | Matsuyama et al. |
| 2003/0119816 | A1 * | 6/2003 | Haesslein ............ A61P 17/06 514/217.03 |
| 2004/0106647 | A1 | 6/2004 | Schneider et al. |
| 2004/0171809 | A1 | 9/2004 | Korsmeyer et al. |
| 2004/0235783 | A1 | 11/2004 | Ghyczy et al. |
| 2005/0026959 | A1 | 2/2005 | Kesseler |
| 2005/0153991 | A1 | 7/2005 | Gianella-Borradori et al. |
| 2005/0261253 | A1 | 11/2005 | Cannizzaro et al. |
| 2006/0079478 | A1 | 4/2006 | Boojamra et al. |
| 2007/0093490 | A1 | 4/2007 | Prien et al. |
| 2008/0027105 | A1 | 1/2008 | Suarez et al. |
| 2008/0108657 | A1 | 5/2008 | Kesseler |
| 2009/0030005 | A1 | 1/2009 | Kamb et al. |
| 2009/0142337 | A1 | 6/2009 | Squires |
| 2010/0143350 | A1 | 6/2010 | Green et al. |
| 2010/0286057 | A1 | 11/2010 | Walensky et al. |
| 2011/0008371 | A1 | 1/2011 | Michelson |
| 2011/0251240 | A1 | 10/2011 | Suarez et al. |
| 2012/0225851 | A1 | 9/2012 | Cardone et al. |
| 2013/0079424 | A1 | 3/2013 | Gerber et al. |
| 2013/0122492 | A1 | 5/2013 | Khosravi et al. |
| 2013/0210024 | A1 | 8/2013 | Yu et al. |
| 2014/0080838 | A1 | 3/2014 | Wendel et al. |
| 2014/0113919 | A1 | 4/2014 | Baffert et al. |
| 2014/0120035 | A1 | 5/2014 | Govindan et al. |
| 2014/0286860 | A1 | 9/2014 | Govindan et al. |
| 2014/0286861 | A1 | 9/2014 | Govindan et al. |
| 2014/0303167 | A1 | 10/2014 | Choidas et al. |
| 2015/0051249 | A1 | 2/2015 | Walensky |
| 2015/0150869 | A1 | 6/2015 | Cardone et al. |
| 2015/0259420 | A1 | 9/2015 | Triebel et al. |
| 2015/0301053 | A1 | 10/2015 | Pierceall et al. |
| 2015/0352097 | A1 | 12/2015 | Cardone et al. |

(56) References Cited

U.S. PATENT DOCUMENTS

| | | |
|---|---|---|
| 2015/0362479 A1 | 12/2015 | Letai et al. |
| 2016/0178612 A1 | 6/2016 | Cardone |
| 2016/0231314 A1 | 8/2016 | Ryan et al. |
| 2016/0235779 A1 | 8/2016 | Marcus |
| 2016/0258933 A1 | 9/2016 | Letai |
| 2016/0273020 A1 | 9/2016 | Pierceall et al. |
| 2016/0279106 A1 | 9/2016 | Ueda et al. |
| 2016/0303101 A1 | 10/2016 | Warner et al. |
| 2016/0340376 A1 | 11/2016 | Siddiqui-Jain et al. |
| 2017/0184567 A1 | 6/2017 | Letai |
| 2017/0260268 A1 | 9/2017 | Beatty et al. |
| 2018/0256580 A1 | 9/2018 | Bearss et al. |
| 2018/0280407 A1 | 10/2018 | Warner et al. |
| 2019/0030017 A1 | 1/2019 | Warner et al. |
| 2019/0177350 A1 | 6/2019 | Siddiqui-Jain et al. |
| 2019/0314357 A1 | 10/2019 | Bearss et al. |
| 2020/0131210 A1 | 4/2020 | Siddiqui-Jain et al. |
| 2020/0200737 A1 | 6/2020 | Bearss et al. |
| 2020/0215071 A1 | 7/2020 | Bearss et al. |
| 2020/0255462 A1 | 8/2020 | Siddiqui-Jain et al. |
| 2020/0276174 A1 | 9/2020 | Bearss et al. |
| 2020/0276215 A1 | 9/2020 | Bearss et al. |
| 2020/0281949 A1 | 9/2020 | Warner et al. |
| 2020/0316084 A1 | 10/2020 | Warner et al. |
| 2021/0052568 A1 | 2/2021 | Warner et al. |

FOREIGN PATENT DOCUMENTS

| | | |
|---|---|---|
| EP | 0137193 A2 | 4/1985 |
| EP | 0253739 B1 | 10/1989 |
| EP | 0253738 B1 | 1/1990 |
| EP | 0 507 278 A2 | 10/1992 |
| EP | 0 241 003 B1 | 10/1993 |
| EP | 0 321 918 B1 | 3/1994 |
| EP | 0 606 046 A1 | 7/1994 |
| EP | 0 366 061 B1 | 1/1996 |
| EP | 0 474 129 B1 | 12/1996 |
| EP | 0 780 386 A1 | 6/1997 |
| EP | 0 818 442 A2 | 1/1998 |
| EP | 0 931 788 A2 | 7/1999 |
| EP | 1 004 578 A2 | 5/2000 |
| EP | 0 979 824 B1 | 10/2004 |
| EP | 3049443 A4 | 4/2017 |
| FR | 2 338 043 A1 | 8/1977 |
| GB | 9912961.1 | 6/1999 |
| IN | CHENP-2007-03645 A | 8/2007 |
| JP | 2004-529125 A | 9/2004 |
| JP | 2007-291111 A | 11/2007 |
| JP | 2008-513494 A | 5/2008 |
| JP | 2009-507820 A | 2/2009 |
| JP | 2011-511803 A | 4/2011 |
| JP | 2013-533213 A | 8/2013 |
| RU | 2 438 664 C2 | 1/2012 |
| RU | 2 474 582 C2 | 2/2013 |
| RU | 2 552 642 C2 | 6/2015 |
| WO | 1990/005719 A1 | 5/1990 |
| WO | 91/00360 A1 | 1/1991 |
| WO | 92/20373 A1 | 11/1992 |
| WO | 1992/009589 A1 | 11/1992 |
| WO | 93/08829 A1 | 5/1993 |
| WO | 94/02602 A1 | 2/1994 |
| WO | 94/11026 A2 | 5/1994 |
| WO | 1995/019970 A1 | 7/1995 |
| WO | 1995/021613 A1 | 8/1995 |
| WO | 96/15263 A1 | 5/1996 |
| WO | 96/27011 A1 | 9/1996 |
| WO | 1996/027583 A1 | 9/1996 |
| WO | 96/33735 A1 | 10/1996 |
| WO | 96/34096 A1 | 10/1996 |
| WO | 1996/033172 A1 | 10/1996 |
| WO | 97/05265 A1 | 2/1997 |
| WO | 97/13760 A1 | 4/1997 |
| WO | 97/16447 A1 | 5/1997 |
| WO | 1997/022596 A1 | 6/1997 |
| WO | 97/30174 A1 | 8/1997 |
| WO | 1997/032856 A1 | 9/1997 |
| WO | 97/42949 A1 | 11/1997 |
| WO | 1998/002434 A1 | 1/1998 |
| WO | 1998/002437 A1 | 1/1998 |
| WO | 1998/002438 A1 | 1/1998 |
| WO | 1998/003516 A1 | 1/1998 |
| WO | 1998/007697 A1 | 2/1998 |
| WO | 98/13344 A1 | 4/1998 |
| WO | 98/14451 A1 | 4/1998 |
| WO | 1998/030566 A1 | 7/1998 |
| WO | 98/33798 A2 | 8/1998 |
| WO | 98/34915 A1 | 8/1998 |
| WO | 1998/033768 A1 | 8/1998 |
| WO | 1998/034918 A1 | 8/1998 |
| WO | 98/50356 A1 | 11/1998 |
| WO | 98/54093 A1 | 12/1998 |
| WO | 1999/007675 A1 | 2/1999 |
| WO | 1999/010349 A1 | 3/1999 |
| WO | 99/16755 A1 | 4/1999 |
| WO | 99/16787 A1 | 4/1999 |
| WO | 1999/024440 A1 | 5/1999 |
| WO | 1999/029667 A1 | 6/1999 |
| WO | 99/35132 A1 | 7/1999 |
| WO | 1999/035146 A1 | 7/1999 |
| WO | 99/53049 A1 | 10/1999 |
| WO | 1999/052889 A1 | 10/1999 |
| WO | 1999/052910 A1 | 10/1999 |
| WO | 1999/061422 A1 | 12/1999 |
| WO | 1999/062890 A1 | 12/1999 |
| WO | 00/06134 A2 | 2/2000 |
| WO | 00/12071 A2 | 3/2000 |
| WO | 00/44362 A2 | 8/2000 |
| WO | 00/59526 A1 | 10/2000 |
| WO | 01/12661 A2 | 2/2001 |
| WO | 2001/060814 A2 | 8/2001 |
| WO | 02/20568 A2 | 3/2002 |
| WO | 03/028001 A1 | 4/2003 |
| WO | 03/040168 A2 | 5/2003 |
| WO | 2004/022580 A2 | 3/2004 |
| WO | 2004/058804 A1 | 7/2004 |
| WO | 2005/017107 A2 | 2/2005 |
| WO | 2005/044839 A2 | 5/2005 |
| WO | 2006/099667 A1 | 9/2006 |
| WO | 2006/101846 A1 | 9/2006 |
| WO | 2006/121168 A1 | 11/2006 |
| WO | 2007/123791 A2 | 11/2007 |
| WO | 2008/021484 A2 | 2/2008 |
| WO | 2008/106635 A1 | 9/2008 |
| WO | 2008/132601 A1 | 11/2008 |
| WO | 2009/044273 A2 | 4/2009 |
| WO | 2010/019570 A2 | 2/2010 |
| WO | 2010/027827 A2 | 3/2010 |
| WO | 2010/030727 A1 | 3/2010 |
| WO | 2010/093742 A1 | 8/2010 |
| WO | 2010/147961 A1 | 12/2010 |
| WO | 2011/066342 A2 | 6/2011 |
| WO | 2011/088137 A2 | 7/2011 |
| WO | 2011/143660 A2 | 11/2011 |
| WO | 2011/153374 A1 | 12/2011 |
| WO | 2012/122370 A2 | 9/2012 |
| WO | 2012/145493 A1 | 10/2012 |
| WO | 2013/079174 A2 | 6/2013 |
| WO | 2013/082660 A1 | 6/2013 |
| WO | 2013/138702 A2 | 9/2013 |
| WO | 2013/170176 A2 | 11/2013 |
| WO | 2013/182519 A1 | 12/2013 |
| WO | 2013/188355 A1 | 12/2013 |
| WO | 2013/188978 A1 | 12/2013 |
| WO | 2014/022758 A1 | 2/2014 |
| WO | 2014/047342 A1 | 3/2014 |
| WO | 2014/055897 | 4/2014 |
| WO | 2014/059028 A1 | 4/2014 |
| WO | 2014/066848 A1 | 5/2014 |
| WO | 2014/100079 A1 | 6/2014 |
| WO | 2014/140180 A1 | 9/2014 |
| WO | 2014/179664 A2 | 11/2014 |
| WO | 2014/194302 A2 | 12/2014 |
| WO | 2014/209804 A1 | 12/2014 |
| WO | 2013/170176 A3 | 1/2015 |

(56) References Cited

FOREIGN PATENT DOCUMENTS

| | | |
|---|---|---|
| WO | 2015/010094 A1 | 1/2015 |
| WO | 2015/017788 A1 | 2/2015 |
| WO | 2015/042249 A1 | 3/2015 |
| WO | 2015/047510 A1 | 4/2015 |
| WO | 2015/061668 A1 | 4/2015 |
| WO | 2015/066305 A1 | 5/2015 |
| WO | 2015/070020 A2 | 5/2015 |
| WO | 2015/081158 A1 | 6/2015 |
| WO | 2015/085847 A1 | 6/2015 |
| WO | 2015/109124 A2 | 7/2015 |
| WO | 2015/112800 A1 | 7/2015 |
| WO | 2015/112805 A1 | 7/2015 |
| WO | 2015/116539 A1 | 8/2015 |
| WO | 2015/130585 A1 | 9/2015 |
| WO | 2015/161247 A1 | 10/2015 |
| WO | 2015/181342 A1 | 12/2015 |
| WO | 2015/195163 A1 | 12/2015 |
| WO | 2015/200119 A1 | 12/2015 |
| WO | 2016/000619 A1 | 1/2016 |
| WO | 2016/028672 A1 | 2/2016 |
| WO | 2016/061144 A1 | 4/2016 |
| WO | 2016/071448 A1 | 5/2016 |
| WO | 2016/073913 A1 | 5/2016 |
| WO | 2016/092419 A1 | 6/2016 |
| WO | 2016/111947 A2 | 7/2016 |
| WO | 2016/115105 A1 | 7/2016 |
| WO | 2016/144803 A2 | 9/2016 |
| WO | 2016/149613 A2 | 9/2016 |
| WO | 2016/154380 A1 | 9/2016 |
| WO | 2016/161248 A1 | 10/2016 |
| WO | 2016/161270 A1 | 10/2016 |
| WO | 2016/172214 A1 | 10/2016 |
| WO | 2016/176288 A1 | 11/2016 |
| WO | 2016/176299 A1 | 11/2016 |
| WO | 2016/187316 A1 | 11/2016 |
| WO | 2017/024073 A1 | 2/2017 |
| WO | 2017/075349 A2 | 5/2017 |
| WO | 2018/013918 A2 | 1/2018 |
| WO | 2018/094275 A1 | 5/2018 |
| WO | 2018/119000 A1 | 6/2018 |
| WO | 2019/055579 A1 | 3/2019 |
| WO | 2019/200243 A1 | 10/2019 |
| WO | 2019/246421 A1 | 12/2019 |
| WO | 2020/077300 A1 | 4/2020 |
| WO | 2020/092615 A1 | 5/2020 |
| WO | 2020/117988 A1 | 6/2020 |
| WO | 2020/118252 A1 | 6/2020 |
| WO | 2020/191326 A1 | 9/2020 |
| WO | 2021/007316 | 1/2021 |
| WO | 2021/007314 | 2/2021 |

OTHER PUBLICATIONS

Higuchi, T., et al., "Pro-drugs as Novel Delivery Systems," A.C.S. Symposium Series, vol. 14, 1975.*
Buccisano et al., "Prognostic and therapeutic implications of minimal residual disease detection in acute myeloid leukemia," Blood 119(2):332-341, 2012.
Fernandez et al., "Anthracycline Dose Intensification in Acute Myeloid Leukemia," New England Journal of Medicine 361(13):1249-1259, 2009.
Gores et al., "Selectively targeting Mcl-1 for the treatment of acute myelogenous leukemia and solid tumors," Genes & Development 26:305-311, 2012.
Hourigan et al., "Development of therapeutic agents for elderly patients with acute myelogenous leukemia," Curr Opin Investig Drugs 11(6): 669-677, 2010.
Kantarjian et al., "Decitabine Improves Patient Outcomes in Myelodysplastic Syndromes," Cancer 106(8): 1794-1803, 2006.
Karp et al., "Timed Sequential Therapy of Acute Leukemia with Flavopiridol: In Vitro Model for a Phase I Clinical Trial," Clin. Cancer Res. 9: 307-315, 2003.
Lazarus et al., "High-Dose Cytosine Arabinoside and Daunorubicin as Primary Therapy in Elderly Patients With Acute Myelogenous Leukemia," Cancer 63:1055-1059, 1989.
Thomas et al., "Phase I Clinical and Pharmacokinetic Trial of the Cyclin-Dependent Kinase Inhibitor Flavopiridol," Cancer Chemother Pharmacol 50:465-472, 2002.
U.S. Appl. No. 16/382,726, filed Apr. 12, 2019.
Adams et al., "The Bcl-2 Protein Family: Arbiters of Cell Survival," Science 281(5381): 1322-1326, 1998.
Adlard et al., "Prediction of the response of colorectal cancer to systemic therapy," The Lancet Oncology 3:75-82, 2002.
Aït-Ikhlef et al., "The motoneuron degeneration in the wobbler mouse is independent of the overexpression of a Bcl2 transgene in neurons," Neurosci Lett 199:163-166, 1995.
Almarzooqi et al., "Comparison of Peripheral Blood versus Bone Marrow Blasts Immunophenotype in Pediatric Acute Leukemias," Ibnosina Journal of Medicine and Biomedical Sciences, pp. 195-204, 2011, (10 pages).
Altschul et al., "Gapped BLAST and PSI-BLAST: a new generation of protein database search programs," Nucleic Acids Res. 25:3389-3402, 1997.
Arguello et al., "Flavopiridol induces apoptosis of normal lymphoid cells, causes immunosuppression, and has potent antitumor activity in vivo against human leukemia and lymphoma xenografts," Blood 91(7):2482-2490, 1998.
Bae et al., "Underphosphorylated BAD interacts with diverse antiapoptotic Bcl-2 family proteins to regulate apoptosis," Apoptosis 6:319-330, 2001.
Barretina et al., "The Cancer Cell Line Encyclopedia enables predictive modelling of anticancer drug sensitivity," Nature 483(7391):603-601, 2012; Erratum in: Nature 492(7428):290, 2012.
Bearss, "NOXA Priming—Predictive Biomarker for Patients With Acute Myeloid Leukemia to Improve Treatment Outcomes," 2016, retrieved from https://openforum.hbs.org/challenge/precision-medicine/submit-ideas/noxa-priming-predic . . . , 7 pages.
Bearss, "Targeting MCL1 dependent cancers by CDK9 inhibition," Abstract for Keynote Address, 9th International Conference on Leukemia and Hematologic Oncology, Oct. 5-6, 2017 London, UK, J Hematol Thrombo Dis 5(5 Suppl), 2017. (1 page).
Bible et al., "Cytotoxic Synergy Between Flavopiridol (NSC 649890, L86-8275) and Various Antineoplastic Agents: The Importance of Sequence of Administration," Cancer Research 57:3375-3380, 1997.
Blachly et al., "Emerging Drug Profile: Cyclin-Dependent Kinase Inhibitors," Leuk Lymphoma 54:2133-2143, 2013. (22 pages).
Bodet et al., "BH3-only protein Bik is involved in both apoptosis induction and sensitivity to oxidative stress in multiple myeloma," Br. J. Cancer 103:1808-1814, 2010.
Bogenberger et al., "BCL-2 family proteins as 5-Azacytidine-sensitizing targets and determinants of response in myeloid malignancies," Leukemia 28(8):1657-1665, 2014.
Bogenberger et al., "Combined venetoclax and alvocidib in acute myeloid leukemia," Oncotarget 8(63):107206-107222, 2017.
Bose et al., "Mcl-1 as a therapeutic target in acute myelogenous leukemia (AML)," Leukemia Research Reports 2:12-14, 2013.
Bouillet et al., "Proapoptotic Bcl-2 Relative Bim Required for Certain Apoptotic Responses, Leukocyte Homeostatis, and to Preclude Autoimmunity," Science 286:1735-1738, 1999.
Boyd et al., "Bik, a novel death-inducing protein shares a distinct sequence motif with Bcl-2 family proteins and interacts with viral and cellular survival-promoting proteins," Oncogene 11(9):1921-1928, 1995.
Brady et al., "Reflections on a peptide," Nature 368:692-693, 1994.
Braun et al., "Preclinical Study of the Bromodomain Inhibitor OTX015 in Acute Myeloid (AML) and Lymphoid (ALL) Leukemias," Blood 122:4218, 2013. (5 pages) (Abstract Only).
Brennan et al., "Preparation of Bispecific Antibodies by Chemical Recombination of Monoclonal Immunoglobulin $G_1$ Fragments," Science 229:81, 1985, 4 pages.
Brooks et al., "CVT-313, a specific and potent inhibitor of CDK2 that prevents neointimal proliferation," J. Biol. Chem. 272(46):29207-29211, 1997.

(56) References Cited

OTHER PUBLICATIONS

Brunelle et al., "MCL-1-dependent leukemia cells are more sensitive to chemotherapy than BCL-2-dependent counterparts," *J. Cell. Biol.* 187(3):429-442, 2009.
Brunetto et al., "First-in-human, Pharmacokinetic and Pharmacodynamic Phase I Study of Resminostat, an Oral Histone Deacetylase Inhibitor, in Patients with Advanced Solid Tumors," *Clinical Cancer Research* 19:5494-5504, 2013.
Buggy et al., "CRA-024781: a novel synthetic inhibitor of histone deacetylase enzymes with antitumor activity in vitro and in vivo," *Mol Cancer Ther* 5:1309-1317, 2006.
Buijs et al., "A novel CBFA2 single-nucleotide Mutation in Familial Platelet Disorder with Propensity to Develop Myeloid Malignancies," *Blood* 98(9):2856-2858, 2001.
Buron et al., "Use of human cancer cell lines mitochondira to explore the mechanisms of BH3 peptides and ABT-737-induced mitochondrial membrane permeabilization," *PLoS One* 5(3):e9924, 2010, 13 pages.
Byrd et al., "Chronic Lymphocytic Leukemia," *Hematology*, pp. 163-183, 2004. (21 pages).
Byrd et al., "Flavopiridol Administered as a Pharmacologically-Derived Schedule Demonstrates Marked Clinical Activity in Refractory, Genetically High Risk, Chronic Lymphocytic Leukemia (CLL)," *Blood* 104:341, 2004, (2 pages).
Byrd et al., "Flavopiridol administered using a pharmacologically derived schedule is associated with marked clinical efficacy in refractory, genetically high-risk chronic lymphocytic leukemia," *Blood* 109:399-494, 2007.
Byrd et al., "Flavopiridol Induces Apoptosis in Chronic Lymphocytic Leukemia Cells via Activation of Caspase-3 Without Evidence of bcl-2 Modulation or Dependence on Functional p53," *Blood* 92:3804-3816, 1998.
Byrd et al., "Sequential Phase II Studies of Flavopiridol by 72-Hour Continuous Infusion and 1-Hour Intravenous Bolus for the Treatment of Relapsed B-Cell Chronic Lymphocytic Leukemia: Results from CALGB Study 19805," *Blood* 104:3485, 2004. (2 pages).
Byrd et al., "Treatment of Relapsed Chronic Lymphocytic Leukemia by 72-Hour Continuous Infusion or 1-Hour Bolus Infusion of Flavopiridol: Results from Cancer and Leukemia Group B Study 19805," *Clin Cancer Res* 11:4176-4181, 2005.
Calin et al., "A MicroRNA Signature Associated with Prognosis and Progression in Chronic Lymphocytic Leukemia," *N. Engl. J. Med.* 353:1793-1801, 2005.
Carlson et al., "Flavopiridol Induces $G_1$ Arrest with Inhibition of Cyclin-dependent Kinase (CDK) 2 and CDK4 in Human Breast Carcinoma Cells," *Cancer Research* 56:2973-2978, 1996.
Caron et al., "Engineered Humanized Dimeric Forms of IgG Are More Effective Antibodies," *J. Exp. Med.* 176:1191-1195, 1992.
Cartron et al., "The first α Helix of Bax Plays a Necessary Role in Its Ligand-Induced Activation by the BH3-Only Proteins Bid and PUMA," *Mol. Cell.* 16:807-818, 2004.
CAS Registry No. 146426-40-6—Flavopiridol, 1993.
Certo et al., "Mitochondria Primed by Death Signals Determine Cellular Addiction to Antiapoptotic BCL-2 Family Members," *Cancer Cell* 9:351-365, 2006.
Chang et al., "Adenovirus-mediated over-expression of the cyclin/cyclin-dependent kinase inhibitor, p21 inhibits vascular smooth muscle cell proliferation and neointima formation in the rat carotid artery model of balloon angioplasty," *J. Clin. Invest.* 96:2260-2268, 1995.
Chao et al., "Flavopiridol Inactivates P-TEFb and Blocks Most RNA Polymerase II Transcription in Vivo," *The Journal of Biological Chemistry* 276:31793-31799, 2001.
Chao et al., "Flavopiridol Inhibits P-TEFb and Blocks HIV-1 Replication," *The Journal of Biological Chemistry* 275:28345-28348, 2000.
Chen et al., "Caspase cleavage of $BIM_{EL}$ triggers a positive feedback amplification of apoptotic signaling," *Proc. Natl. Acad. Sci. USA* 101(5):1235-1240, 2004.

Chen et al., "Downregulation of cyclin-dependent kinase 2 activity and cyclin A promoter activity in vascular smooth muscle cells by p27(KIP1), an inhibitor of neointima formation in the rat carotid artery," *J. Clin. Invest.* 99:2334-2341, 1997.
Chen et al., "Mcl-1 Down-regulation Potentiates ABT-737 Lethality by Cooperatively Inducing Bak Activation and Bax Translocation," *Cancer Res* 67(2):782-791, 2007.
Chen et al., "Differential Targeting of Prosurvival Bcl-2 Proteins by Their BH3-Only Ligands Allows Complementary Apoptotic Function," *Molecular Cell* 17:393-403, 2005.
Chen et al., "Mechanism of action of SNS-032, a novel cyclin-dependent kinase inhibitor in chronic lymphocytic leukemia," *Blood* 113:4637-4645, 2009.
Chen et al., "Transcription inhibition by flavopiridol: mechanism of chronic lymphocytic leukemia cell death," *Blood* 106:2513-2519, 2005.
Cheng et al., "Bax-independent inhibition of apoptosis by $Bcl-x_L$," *Nature* 379:554-556, 1996.
Cheng et al., "BCL-2, $BCL-X_L$ Sequester BH3 Domain-Only Molecules Preventing BAX- and BAK-Mediated Mitochondrial Apoptosis," *Mol. Cell* 8(3):705-711, 2001.
Cheronis, "Semimicro Experimental Organic Chemistry," deGratt, pp. 67-69 (1958).
Cheson et al., "National Cancer Institute-Sponsored Working Group Guidelines for Chronic Lymphocytic Leukemia: Revised Guidelines for Diagnosis and Treatment," *Blood* 87:4990-4997, 1996.
Chipuk et al., "Direct Activation of Bax by p53 Mediates Mitochondrial Membrane Permeabilization and Apoptosis," *Science* 303:1010-1014, 2004.
Chittenden et al., "A conserved domain in Bak, distinct from BH1 and BH2, mediates cell death and protein binding functions," *EMBO J* 14(22):5589-5596, 1995.
Chittenden et al., "Induction of apoptosis by the Bcl-2 homologue Bak," *Nature* 374(6524):733-736, 1995.
Chonghaile et al., "Mitochondrial Apoptotic Priming Measured by BH3 Profiling Regulates Clinical Response to Chemotherapy in Myeloma and Acute Lymphoblastic Leukemia and Explains Therapeutic Index," Abstract 1442, 53rd ASH Annual Meeting and Exposition, Dec. 10-13, 2011, American Society of Hematology, 6 pages.
Chonghaile et al., "Mimicking the BH3 domain to kill cancer cells," *Oncogene* 27:S149-S157, 2009.
Chonghaile et al., "Pretreatment mitochondrial priming correlates with clinical response to cytotoxic chemotherapy," *Science* 334(6059):1129-1133, 2011.
Chonghaile et al., "Pretreatment mitochondrial priming correlates with clinical response to cytotoxic chemotherapy," *Science* 334(6059):1129-1133, 2011. Supporting Online Material, 36 pages.
Choudhary et al., "MCL-1 and BCL-xL-dependent resistance to the BCL-2 inhibitor ABT-199 can be overcome by preventing PI3K/AKT/mTOR activation in lymphoid malignancies," *Cell Death and Disease* 6:e1593, 2015. (12 pages).
Clowes et al., "Significance of quiescent smooth muscle migration in the injured rat carotid artery," *Circ. Res.* 56(1):139-145, 1985.
Cole et al., "The EBV-Hybridoma technique and its application to human lung cancer," *Monoclonal Antibodies and Cancer Therapy*:77-96, 1985.
Conaway et al., "The Mediator Complex and Transcription Elongation," *Biochim Biophys Acta* 1829:69-75, 2013. (16 pages).
Cory et al., "The Bcl2 Family: Regulators of the Cellular Life-or-Death Switch," *Nat. Rev. Cancer* 2(9):647-656, 2002.
Cosulich et al., "Regulation of apoptosis by BH3 domains in a cell-free system," *Curr. Biol* 7(12):913-920, 1997.
Cote et al., "Generation of human monoclonal antibiotics reactive with cellular antigens," *Proc. Natl. Acad. Sci. USA* 80:2026-2030, 1983.
Czabotar et al., "Bax Activation by Bim?," *Cell Death and Differentiation* 16:1187-1191, 2009.
Czabotar et al., "Structural insights into the degradation of Mcl-1 induced by BH3 domains," *PNAS* 104:6211-6222, 2007.
Czech et al., "Antitumoral activity of flavone L 86-8275," *International Journal of Oncology* 6:31-36, 1995.

(56) References Cited

OTHER PUBLICATIONS

Daigle et al., "Potent Inhibition of DOT1L as Treatment of MLL-fusion Leukemia," *Blood* 122:1017-1025, 2013.
Danial et al., "Cell Death: Critical Control Points," *Cell* 116:205-219, 2004.
Davids et al., "BH3 profiling demonstrates that restoration of apoptotic priming contributes to increased sensitivity to PI3K inhibition in stroma-exposed chronic lymphocytic leukemia cells," *Blood* 118(21): Nov. 18, 2011, Abstract.
Davids et al., "Targeting the B-cell lymphoma/leukemia 2 family in cancer," *J Clin Oncol* 30(25):3121-3135, 2012.
De Azevedo Jr. et al., "Structural basis for inhibition of cyclin-dependent kinase 9 by flavopiridol," *Biochemical and Biophysical Research Communications* 293:566-511, 2002.
DeYoung et al., "Gene therapy for restenosis, Are We Ready?" *Circ. Res.* 82:306-313, 1998.
Debrincat et al., "BCL-2 is dispensable for thrombopoiesis and platelet survival," *Cell Death & Disease* 6:e1721, 2015. (8 pages).
DeGrado, "Design of peptides and proteins," *Adv. Protein Chem* 39:51-124, 1988.
Deng et al., "BH3 Profiling Identifies Three Distinct Classes of Apoptotic Blocks to Predict Response to ABT-737 and Conventional Chemotherapeutic Agents," *Cancer Cell* 12:171-185, 2007.
Derenne et al., "Antisense strategy shows that Mcl-1 rather than Bcl-2 or Bcl-$x_L$ is an essential survival protein of human myeloma cells," *Blood* 100:194-199, 2002.
Desagher et al., "Bid-induced Conformational Change of Bax Is Responsible for Mitochondrial Cytochrome c Release during Apoptosis," *J. Cell Biol* 144(5):891-901, 1999.
Dettman et al., "Abstract 3400: Mitochondrial profiling in AML patients treated with an Alvocidib containing regimen reveals MCL1 dependency in responder bone marrow," *Cancer Res* 75:3400, 2015. (2 pages).
Dettman et al., "Context Dependent Diagnostics Test for Guiding Cancer Treatment," U.S. Appl. No. 62/102,499, filed Jan. 12, 2015, 71 pages.
Di Lisa et al., "Mitochondrial Function and Cell Injury in Single Cardiac Myocytes Exposed to Anoxia and Reoxygenation," *Transplant. Proc.* 27(5):2829-2830, 1995.
Di Lisa et al., "Mitochondrial membrane potential in single living adult rat cardiac myocytes exposed to anoxia or metabolic inhibition," *J. Physiol* 486(1):1-13, 1995.
Diamandis et al., *Immunoassay*, Academic Press, Inc., NY, 1996.
Dinnen et al., "Redirecting Apoptosis to Aponecrosis Induces Selective Cytotoxicity to Pancreatic Cancer Cells through Increased ROS, Decline in ATP Levels, and VDAC," *Molecular Cancer Therapeutics* 12:2792-2803, 2013.
Dohner et al., "Genomic Aberrations and Survival in Chronic Lymphocytic Leukemia," *N. Engl. J. Med.* 343:1910-1916, 2000.
Drees et al., "Flavopiridol (L86-8275): Selective antitumor activity in vitro and activity in vivo for prostate carcinoma cells," *Clin. Cancer Res.* 3:273-279, 1997.
Egle et al., "Bim is a suppressor of Myc-induced mouse B cell leukemia," *Proc. Natl. Acad. Sci USA* 101(16):6164-6169, 2004.
Ellerby et al., "Anti-cancer activity of targeted pro-apoptotic peptides," *Nat. Med.* 5(9):1032-1038, 1999.
Elliott et al., "Intercellular Trafficking and Protein Delivery by a Herpesvirus Structural Protein," *Cell* 88:223-233, 1997.
Elston et al., "Pathological prognostic factors in breast cancer. I. The value of histological grade in breast cancer: experience from a large study with long-term follow-up," *Histopathology* 19:403-410, 1991.
Ember et al., "Acetyl-lysine Binding Site of Bromodomain-Containing Protein 4 (BRD4) Interacts with Diverse Kinase Inhibitors," *ACS Chemical Biology* 9:1160-1171, 2014.
Eskes et al., "Bid Induces the Oligomerization and Insertion of Bax into the Outer Mitochondrial Membrane," *Mol. Cell. Biol.* 20(3):929-935, 2000.
Falkenberg et al., "Histone deacetylases and their inhibitors in cancer, neurological diseases and immune disorders," *Nature Reviews Drug Discovery* 13:673-691, 2014.

Fanidi et al., "Cooperative interaction between c-myc and bcl-2 proto-oncogenes," *Nature* 359:554-556, 1992.
Filippakopoulos et al., "Selective inhibition of BET bromodomains," *Nature* 468:1067-1073, 2010.
Filippakopoulos et al., "Targeting bromodomains: epigenetic readers of lysine acetylation," *Nature Reviews Drug Discovery* 13:337-356, 2014.
Fish et al., "Identification of a Chemical Probe for Bromo and Extra C-Terminal Bromodomain Inhibition through Optimization of a Fragment-Derived Hit," *Journal of Medicinal Chemistry* 55:9831-9837, 2012.
Fiskum et al., "Apoptosis-Related Activities Measured with Isolated Mitochondria and Digitonin—Permeabilized Cells," *Methods in Enzymology* 322:222-234, 2000.
Fiskus et al., "Highly Active Combination of BRD4 Antagonist and Histone Deacetylase Inhibitor against Human Acute Myelogenous Leukemia Cells," *Molecular Cancer Therapeutics* 13:1142-1154, 2014.
Flinn et al., "Flavopiridol Administered as a 24-Hour Continuous Infusion in Chronic Lymphocytic Leukemia lacks Clinical Activity," *Leukemia Res* 29:1253-1257, 2005.
Foight et al., "Designed BH3 Peptides with High Affinity and Specificity for Targeting Mcl-1 in Cells," *ACS Chem. Biol.* 9:1962-1968, 2014.
Frankel et al., "Activity of synthetic peptides from the Tat protein of human immunodeficiency virus type 1," *Proc. Natl. Acad. Sci. USA* <35:7397-7401, 1989.
Friedman et al., "Precision medicine for cancer with next-generation functional diagnostics," *Nat Rev Cancer* 75(12):747-756, 2015.
Fuchs et al., "Pathway for Polyarginine Entry into Mammalian Cells," *Biochemistry* 43(9):2438-2444, 2004.
Fukui et al., "The Analysis of the Effect of JQ1 and Flavopiridol on Chondrocytes under Inflammatory Stimuli," ORS 2014 Annual Meeting, 4 pages.
Futaki et al., "Arginine-rich Peptides: An Abundant Source of Membrane-Permeable Peptides Having Potential as Carriers for Intracellular Protein Delivery," *J. Biol. Chem* 275(8):5836-5840, 2001.
Geng et al., "Apoptosis of vascular smooth muscle cells induced by in vitro stimulation with interferon-$\gamma$, tumor necrosis factor-$\alpha$, and interleukin-1$\beta$," *Arterioscler. Thromb. Biol* 16:19-27, 1996.
Gerber et al., "Association of acute myeloid leukemia's most immature phenotype with risk groups and outcomes," *Haematologica* 101(5):607-616, 2016. (18 pages).
Geserick et al., "The ratio of Mcl-1 and Noxa determines ABT737 resistance in squamous cell carcinoma of the skin," *Cell Death and Disease* 5:e1412, 2014. (14 pages).
Ghyczy et al., "Electrophilic Methyl Groups Present in the Diet Ameliorate Pathological States Induced by Reductive and Oxidative Stress: A Hypothesis," *British Journal of Nutrition* 85(4):409-414, 2001.
Giles et al., "A Phase I Study of Intravenous LBH589, a Novel Cinnamic Hydroxamic Acid Analogue Histone Deacetylase Inhibitor in Patients with Refractory Hematologic Malignancies," *Clin Cancer Res* 72:4628-4635, 2006.
Gojo et al., "The Cyclin-dependent Kinase Inhibitor Flavopiridol Induces Apoptosis in Multiple Myeloma Cells through Transcriptional Repression and Down-Regulation of Mcl-1," *Clinical Cancer Research* 8:3527-3538, 2002.
Goldsmith et al., "BH3 peptidomimetics potently activate apoptosis and demonstrate single agent efficacy in neuroblastoma," *Oncogene* 25:4525-4533, 2006.
Göttlicher et al., "Valproic acid defines a novel class of HDAC inhibitors inducing differentiation of transformed cells," *The EMBO Journal* 20:6969-6978, 2001.
Green et al., "A matter of life and death," *Cancer Cell* 1:19-30, 2002.
Green et al., "The Pathophysiology of Mitochondrial Cell Death," *Science* 305:626-629, 2004.
Green, "Life, Death, BH3 Profiles, and the Salmon Mousse," *Cancer Cell* 12:97-99, 2007.

(56) References Cited

OTHER PUBLICATIONS

Griffiths et al., "Cell Damage-induced Conformational Changes of the Pro-Apoptotic Protein Bak in Vivo Precede the Onset of Apoptosis," *J. Cell. B+G186iol.* 144(5):903-914, 1999.

Gross et al., "Enforced dimerization of BAX results in its translocation, mitochondrial dysfunction and apoptosis," *EMBO J* 17(14):3878-3885, 1998.

Gruber et al., "Efficient Tumor Cell Lysis Mediated by a Bispecific Single Chain Antibody Expressed in *Escherichia coli*," *J. Immunol* 152:5368-5374, 1994.

Guha, "Cyclin-dependent kinase inhibitors move into Phase III," *Nature Reviews Drug Discovery* 11:892-894, 2012.

Gul et al., "Apoptotic blocks and chemotherapy resistance: strategies to identify Bcl-2 protein signatures," *Briefings in Functional Genomics and Proteomics* 7(1):27-34, 2008.

Hanahan et al., "Heritable formation of pancreatic β-cell tumours in transgenic mice expressing recombinant insulin/simian virus 40 oncogenes," *Nature* 315:115-122, 1985.

Hanahan et al., "The Hallmarks of Cancer," *Cell* 100:57-70, 2000.

Hans et al., "β-Carbolines induce apoptosis in cultured cerebellar granule neurons via the mitochondrial pathway," *Neuropharmacology* 48:105-117, 2005.

Harada et al., "Survival factor-induced extracellular signal-regulated kinase phosphorylates BIM, inhibiting its association with BAX and proapoptotic activity," *Proc. Natl. Acad. Sci. USA* 101(43):15313-15317, 2004.

Harada et al., "Discovery of potent and orally bioavailable 17β-hydroxysteroid dehydrogenase type 3 inhibitors," *Bioorganic & Medicinal Chemistry* 20:3242-3254, 2012.

Haws et al., "E881: By an MCL-1-Dependent Mechanism, Alvocidib Potentiates the Activity of Cytarabine and Mitoxantrone When Administered in a Time Sequential Regimen in AML," Hematologica 102(Suppl. 2):362, 2017, (1 page).

Haws et al., "E1204: Alvocidib Synergizes With Venetoclax in Preclinical Models of Multiple Myeloma," *Hematologica* 102(Suppl. 2):495, 2017, (1 page).

Hemann et al., "Evasion of the p53 tumour surveillance network by tumour-derived MYC mutants," *Nature* 436:807-811, 2005.

Hemann et al., "Suppression of tumorigenesis by the p53 target PUMA," *Proc. Natl. Acad. Sci. USA* 101(25):9333-9338, 2004.

Hengartner et al., "C. elegans Cell Survival Gene ced-9 Encodes a functional Homolog of the Mammalian Proto-Oncogene bcl-2," *Cell* 76:665-676, 1994.

Hirst et al., "Application of Non-Parametric Regression to Quantitative Structure-Activity Relationships," *Bioorganic & Medicinal Chemistry* 10:1037-1041, 2002.

Hnisz et al., "Super-Enhancers in the Control of Cell Identity and Disease," *Cell* 155:934-947, 2013.

Holinger et al., "Bak BH3 Peptides Antagonize Bcl-$x_L$ Function and Induce Apoptosis through Cytochrome c-independent Activation of Caspases," *J Biol. Chem.* 274(19):13298-13304, 1999.

Holliger et al., "Diabodies: Small bivalent and bispecific antibody fragments," *Proc. Natl. Acad. Sci. USA* 90:6444-6448, 1993.

Hoogenboom et al., "By-passing Immunisation. Human Antibodies from Synthetic Repertoires of Germline $V_H$ Gene Segments rearranged in Vitro," *J. Mol. Biol.* 227:381-388, 1992.

Hopp et al., "Prediction of protein antigenic determinants from amino acid sequences," *Proc. Natl. Acad. Sci. USA* 78:3824-3828, 1981.

Hoppel et al., "The action of digitonin on rat liver mitochondria. The effects on enzyme content," *Biochem J.* 107(3):367-375, 1968.

Hsu et al., "Nonionic Detergents Induce Dimerization among Members of the Bcl-2 Family," *J. Biol. Chem* 272(21):13829-13834, 1997.

Huang et al., "BH3-Only Proteins—Essential Initiators of Apoptotic Cell Death," *Cell* 103:839-842, 2000.

Huber et al., "Profile of venetoclax and its potential in the context of treatment of relapsed or refractory chronic lymphocytic leukemia," *Onco. Targets Ther.* 10:645-656, 2017.

Hunter, T., "Braking the cycle," *Cell* 75:839-841, 1993.

Hunter, T., "Protein kinases and phosphatases: The yin and yang of protein phosphorylation and signaling," *Cell* 80:225-236, 1995.

Huse et al., "Generation of a large Combinatorial Library of the Immunoglobulin Repertoire in Phage Lambda," *Science* 246:1275-1281, 1989.

Innocenti et al., "Flavopiridol Metabolism in Cancer Patients Is Associated with the Occurrence of Diarrhea," *Clinical Cancer Research* 6:3400-3405, 2000.

Inohara et al., "harakiri, a novel regulator of cell death, encodes a protein that activates apoptosis and interacts selectively with survival-promoting proteins Bcl-2 and Bcl-$X_L$," *EMBO J* 16(1):1686-1694, 1997.

Ishizawa et al., "Mitochondrial Profiling of Acute Myeloid Leukemia in the Assessment of Response to Apoptosis Modulating Drugs," *PLoS One* 10:e0138377, 2015, 16 pages.

Jackson et al., "Heat shock induces the release of fibroblast growth factor 1 from NIH 3T3 cells," *Proc. Natl. Acad. Sci. USA* 89:10691-10695, 1992.

Jameson et al., "A rationally designed CD4 analogue inhibits experimental allergic encephalomyelitis," *Nature* 368:744-746, 1994.

Jones et al., "Replacing the complementarity-determining regions in a human antibody with those from a mouse," *Nature* 321:522-525, 1986.

Jonkers et al., "Oncogene addiction: Sometimes a temporary slavery," *Cancer Cell* 6:535-538, 2004.

Karp et al., "Phase I and pharmacokinetic study of flavopiridol followed by 1-β-D-arabinofuranosylcytosine and mitoxantrone in relapsed and refractory adult acute leukemias," *Clin. Cancer Res.* 11(23):8403-8412, 2005.

Karp et al., "Sequential flavopiridol, cytosine arabinoside, and mitoxantrone: a phase II trial in adults with poor-risk acute myelogenous leukemia," *Clin. Cancer Res.* 13(15 Pt. 1):4467-4473, 2007.

Kasper et al., "Targeting MCL-1 sensitizes FLT3-ITD-positive leukemias to cytotoxic therapies," *Blood Cancer J* 2, 10 pages, 2012.

Kearney et al., "Histopathology of in-stent restenosis in patients with peripheral artery disease," *Circulation* 95:1998-2002, 1997.

Keating et al., "Results of First Salvage Therapy for Patients Refractory to a Fludarabine Regimen in Chronic Lymphocytic Leukemia," *Leuk. Lymph.* 43:1175-1762, 2002.

Keating et al., "Therapeutic role of alemtuzumab (Campath-1H) in patients who have failed fludarabine: results of a large international study," *Blood* 99:3554-3561, 2002.

Kelekar et al., "Bad is a BH3 Domain-Containing Protein that Forms an Inactivating Dimer with Bcl-$x_L$," *Mol. Cell. Biol.* 17(12):7040-7046, 1997.

Kelekar et al., "Bcl-2-family proteins: the role of the BH3 domain in apoptosis," *Trends in Cell Biol* 8:324-330, 1998.

KG-1a, ATCC® CCC-246.1™ ATCC Product Sheet, 3 pages, May 31, 2013.

Kim et al., "Abstract 3728: Targeting MCL-1 expression, through the inhibition of CDK9 and super enhancer driven transcription, offers multiple opportunities for rational drug combinations," *Cancer Research* 76(14 Suppl.):3728, 2016.

Kim et al., "Alvocidib Synergizes With Cytarabine and Daunorubicin (7+3) in Preclinical Models of Acute Myeloid Leukemia," EHA Learning Center, May 18, 2017, retrieved from https://learningcenter.ehaweb.org/eha/2017/22nd/180678, 3 pages.

Kitada et al., "Protein kinase inhibitors flavopiridol and 7-hydroxy-staurosporine down-regulate antiapoptosis proteins in B-cell chronic lymphocytic leukemia," *Blood* 96:393-391, 2000.

Kohler et al., "Continuous cultures of fused cells secreting antibody of predefined specificity," *Nature* 256:495-497, 1975.

König et al., "The Novel Cyclin-Dependent Kinase Inhibitor Flavopiridol Downregulates Bcl-2 and Induces Growth Arrest and Apoptosis in Chronic B-Cell Leukemia Lines," *Blood* 90:4307-4312, 1997.

Korsmeyer et al., "Pro-apoptotic cascade activates BID, which oligomerizes BAK or BAX into pores that result in the release of cytochrome c," *Cell Death Differ* 7(12):1166-1173, 2000.

Kozbor et al., "The production of monoclonal antibodies from human lymphocytes," *Immunol Today* 4:72-79, 1983.

Kryštof et al., "Cyclin-Dependent Kinase Inhibitors as Anticancer Drugs," *Current Drug Targets* 11:291-302, 2010.

(56) References Cited

OTHER PUBLICATIONS

Kuwana et al., "BH3 Domains of BH3-Only Proteins Differentially Regulate Bax-Mediated Mitochondrial Membrane Permeabilization Both Directly and Indirectly," *Mol. Cell.* 17:525-535, 2005.

Kuwana et al., "Bid, Bax, and Lipids Cooperate to Form Supramolecular Openings in the Outer Mitochondrial Membrane," *Cell* 111:331-342, 2002.

Kyte et al., "A Simple Method for displaying the Hydropathic Character of a protein," *J. Mol. Biol.* 157:105-132, 1982.

La Vieira et al., "Cell permeable BH3-peptides overcome the cytoprotective effect of Bcl-2 and Bcl-$X_L$," *Oncogene* 21:1963-1977, 2002.

Labi et al., "Targeting the Bcl-2-regulated apoptosis pathway by BH3 mimetics: a breakthrough in anticancer therapy?" *Cell Death and Differentiation* 15:977-987, 2008.

Lemke et al., "Immunobiology of the TAM Receptors," *Nature Reviews Immunology* 8:327-336, 2008.

Leo et al., "Characterization of the Antiapoptotic Bcl-2 Family Member Myeloid Cell Leukemia-1 (Mcl-1) and the Stimulation of Its Message by Gonadotropins in the Rat Ovary," *Endocrinol* 140:5469-5411, 1999.

Letai et al., "Antiapoptotic BCL-2 is required for maintenance of a model leukemia," *Cancer Cell* 6:241-249, 2004.

Letai et al., "Distinct BH3 domains either sensitize or activate mitochondrial apoptosis, serving as prototype cancer therapeutics," *Cancer Cell* 2:183-192, 2002.

Letai, "Perturbing cancer cell mitochondria to learn how to kill cancer with BH3 profiling," Broad Institute, Seminar Series on Cell Circuits and Epigenomics, Jul. 28, 2014, Presentation, 47 pages.

Letai, "The BCL-2 network: Mechanistic insights and therapeutic potential," *Drug Disc. Today: Disease Mechanisms* 2(2): 145-151, 2005.

Letai, "BH3 domains as BCL-2 inhibitors: prototype cancer therapeutics," *Expert Opin. Biol. Ther.* 3:293-304, 2003.

Li et al., "Cleavage of BID by Caspase 8 Mediates the Mitochondrial Damage in the Fas Pathway of Apoptosis," *Cell* 94(4):491-501, 1998.

Li et al., "Endonuclease G is an apoptotic DNase when released from mitochondria," *Nature* 412:95-99, 2001.

Li et al., "tsg101: A Novel tumor susceptibility gene isolated by controlled Homozygous functional knockout of Allelic Loci in Mammalian Cells," *Cell* 85:319-329, 1996.

Lin et al., "Flavopiridol given as a 30-min intravenous (IV) bolus followed by 4-hr continuous IV infusion (CIVI) results in clinical activity and tumor lysis in refractory chronic lymphocytic leukemia (CLL)," *Journal of Clinical Oncology, 2004 ASCO Annual Meeting Proceedings (Post-Meeting Edition)* 22(14S):6564, 2004, (1 page).

Lin et al., "Seventy-Two Hour Continuous Infusion Flavopiridol in Relapsed and Refractory Mantle Cell Lymphoma," *Leukemia & Lymphoma* 43:793-797, 2002.

Lin et al., "Targeting MCL-1/BCL-$X_L$ Forestalls the Acquisition of Resistance to ABT-199 in Acute Myeloid Leukemia," *Scientific Reports* 6(1): 1-10, 2016.

Liu et al., "Bax conformational change is a crucial step for PUMA-mediated apoptosis in human leukemia," *BioChem. Biophys. Res. Commun.* 310(3):956-962, 2003.

Liu et al., "BH3-based Fusion Artificial Peptide Induces Apoptosis and Targets Human Colon Cancer," *Molecular Therapy* 17:1509-1516, 2009.

Liu et al., "CDKI-71, a novel CDK9 inhibitor, is preferentially cytotoxic to cancer cells compared to flavopiridol," *Int. J. Cancer* 130:1216-1226, 2012.

Lonberg et al., "Antigen-specific human antibodies from mice comprising four distinct genetic modifications," *Nature* 368:856-859, 1994.

Long et al., "Optimization and validation of mitochondria-based functional assay as a useful tool to identify BH3-like molecules selectively targeting anti-apoptotic Bcl-2 proteins," *BMC Biotechnol* 13:45, 2013, 10 pages.

Lovén et al., "Selective Inhibition of Tumor Oncogenes by Disruption of Super-Enhancers," *Cell* 153:320-334, 2013, (27 pages).

Lozanski et al., "Alemtuzumab is an effective therapy for chronic lymphocytic leukemia with p53 mutations and deletions," *Blood* 103:3278-3281, 2004.

Lu et al., "Compensatory Induction of MYC Expression by Sustained CDK9 Inhibition via a BRD4-dependent Mechanism," *eLife*, 2015. (26 pages).

Luo et al., "Bid, a Bcl2 interacting protein, mediates cytochrome c release from mitochondria in response to activation of cell surface death receptors," *Cell* 94(4):481-490, 1998.

Lutter et al., "The pro-apoptotic Bcl-2 family member tBid localizes to mitochondrial contact sites," *BMC Cell Biology* 2:22, 2001, 9 pages.

Mann et al., "Cell cycle inhibition preserves endothelial function in genetically engineered rabbit vein grafts," *J. Clin. Invest.* 99(6):1295-1301, 1997.

Marani et al., "Identification of Novel Isoforms of the BH3 Domain Protein Bim which Directly Activate Bax to Trigger Apoptosis," *Mol. Cell. Biol.* 22(11):3577-3589, 2002.

Marks et al., "By-passing Immunization. Human Antibodies from v-gene libraries displayed on phage," *J. Mol. Biol.* 222:581-597, 1991.

Marks et al., "By-passing Immunization: building high affinity human antibodies by chain shuffling," *Bio/Technology* 10:719-783, 1992.

Martin, "Opening the Cellular Poison Cabinet," *Science* 330:1330-1331, 2010.

Mason et al., "The Hypogonadal mouse: reproductive functions restored by gene therapy," *Science* 234:1372-1378, 1986.

Matsushita et al., "A high-efficiency protein transduction system demonstrating the role of PKA in long-lasting long-term potentiation," *J. Neuroscience* 21:6000-6007, 2001.

Matsuzaki, "Why and how are peptide-lipid interactions utilized for self-defence?" *Biochem. Soc. Transactions* 29:598-601, 2001.

McDonnell et al., "bcl-2-Immunoglobulin Transgenic Mice Demonstrate Extended B Cell Survival and Follicular Lymphoproliferation," *Cell* 57:79-88, 1989.

Means et al., "Modifications to change properties," in *Chemical Modification of Protein*, Chapter 3, pp. 35-54, Holden-Day (1974).

Miller et al., "Therapeutic Strategies to Enhance the Anticancer Efficacy of Histone Deacetylase Inhibitors," *J. Biomed. Biotechnol.* 2011:17 pages, 2011.

Milstein et al., "Hybrid hybridomas and their use in immunohistochemistry," *Nature* 305:537-539, 1983.

Molassiotis et al., "Use of complementary and alternative medicine in cancer patients: A European survey," *Annals of Oncology* 16:655-663, 2005.

Montero et al., "Drug-induced death signaling strategy rapidly predicts cancer response to chemotherapy," *Cell* 160(5):977-989, 2015.

Moore et al., "Chronic lymphocytic leukemia requires BCL2 to sequester prodeath BIM, explaining sensitivity to BCL2 antagonist ABT-737," *J. Clin. Invest.* 117(1):112-121, 2007.

Moore et al., "BH3 profiling—measuring integrated function of the mitochondrial apoptotic pathway to predict cell fate decisions," *Cancer Lett* 332:202-205, 2013. (10 pages).

Morishita et al., "A gene therapy strategy using a transcription factor decoy of the E2F binding site inhibits smooth muscle proliferation in vivo," *Proc. Natl. Acad. Sci. USA* 92:5855-5859, 1995.

Morrison et al., "Success in specification," *Nature* 368:812-813, 1994.

Motwani et al., "Sequential Dependent Enhancement of Caspase Activation and Apoptosis by Flavopiridol on Paclitaxel-Treated Human Gastric and Breast Cancer Cells," *Clinical Cancer Research* 5(7):1876-1883, 1999.

Muchmore et al., "X-ray and NMR structure of human Bcl-$x_L$, an inhibitor of programmed cell death," *Nature* 381:335-341, 1996.

Munson et al., "Ligand: A Versatile Computerized Approach for Characterization of Ligand-Binding Systems," *Analytical Biochemistry* 107:220-239, 1980.

(56) References Cited

OTHER PUBLICATIONS

Murthi et al., "Structure-Activity Relationship Studies of Flavopiridol Analogues," *Bioorganic & Medicinal Chemistry Letters* 10:1037-1041, 2000.
Nagai et al., "Studies on Psychotropic Agents. VI.[1)] Synthesis of 1'-Methylspiro[6-fluoroindan-1, 3'-pyrrolidine]-3-one and Related Compounds," *Chem. Pharm. Bull.* 28(5):1381-1393, 1980.
Naik et al., "An Antiinflammatory Cum Immunomodulatory Piperidinylbenzopyranone From *Dysoxylum Binectariferum*: Isolation, Structure and Total Synthesis," *Tetrahedron* 44:2081-2086, 1988.
Nakano et al., "PUMA, a Novel Proapoptotic Gene, Is Induced by p53," *Molecular Cell* 7:683-694, 2001.
Narita et al., "Bax interacts with the permeability transition pore to induce permeability transition and cytochrome c release in isolated mitochondria," *Proc. Natl. Acad. Sci. USA* 95:14681-14686, 1998.
Neuberger et al., "Generating high-avidity human Mabs in mice," *Nature Biotechnology* 14:826, 1996.
Nguyen et al., "Azacitidine and decitabine have different mechanisms of action in non-small cell lung cancer cell lines," *Lung Cancer: Targets and Therapy* 1:119-140, 2010.
Noel et al., "Abstract C244: Development of the BET bromodomain inhibitor OTX015," *Molecular Cancer Therapeutics* 12(11): Supplement, 2013.
O'Brien et al., "Phase I to II Multicenter Study of Oblimersen Sodium, a Bcl-2 Antisense Oligonucleotide, in Patients With Advanced Chronic Lymphocytic Leukemia," *J. Clin. Oncol.* 23(30):7697-7702, 2005.
O'Brien et al., "Proliferation in primary and restenotic coronary atherectomy tissue: implications for antiproliferative therapy," *Circ. Res.* 73(2):223-231, 1993.
O'Connor et al., "Bim: a novel member of the Bcl-2 family that promotes apoptosis," *EMBO J* 17(2):384-395, 1998.
Oda et al., "Noxa, a BH3-Only Member of the Bcl-2 Family and Candidate Mediator of p53-Induced Apoptosis," *Science* 288:1053-1058, 2000.
Odore et al., "Abstract LB-231: A phase I pharmacokinetic study of OTX015 for the treatment of patients with hematologic malignancies," *Cancer Research* 74(Supplement 19), 2014. (4 pages) (Abstract Only).
Oh et al., "Conformational Changes in BID, a Pro-apoptotic BCL-2 Family Member, upon Membrane Binding," *J. Biol. Chem.* 280(1):753-767, 2005.
Okamoto et al., "Increased antitumor potential of the raloxifene prodrug, raloxifene diphosphate," *Int. J. Cancer* 122:2142-2147, 2008.
Oltersdorf et al., "An inhibitor of Bcl-2 family proteins induces regression of solid tumours," *Nature* 435:677-681, 2005.
Opferman et al., "Development and maintenance of B and T lymphocytes requires antiapoptotic MCL-1," *Nature* 426:671-676, 2003.
Oppermann et al., "High-content screening identifies kinase inhibitors that overcome venetoclax resistance in activated CLL cells," *Blood* 128(1):934-947, 2016.
Oscier et al., "Multivariate analysis of prognostic factors in CLL: clinical stage, IGVH gene mutational status, and loss or mutation of the p53 gene are independent prognostic factors," *Blood* 100:1177-1184, 2002.
Otsuka et al., "Effect of Polymorphic Forms of Bulk Powders on Pharmaceutical Properties of Carbamazepine Granules," *Chem. Pharm. Bull.* 47(6):852-856, 1999.
Paoluzzi et al., "The BH3-only mimetic ABT-737 synergizes the antineoplastic activity of proteasome inhibitors in lymphoid malignancies," *Blood* 112:2906-2916, 2008.
Paquin et al., "Design and syntheis of 4-[(s-triazin-2-ylamino)methyl]-N-(2-aminophenyl)-benzamides and their analogues as a novel class of histone deacetylase inhibitors," *Bioorganic & Medicinal Chemistry Letters* 18:1067-1071, 2008.

Park et al., "Inhibitors of cyclin-dependent kinases promote survival of post-mitotic neuronally differentiated PC12 cells and sympathetic neurons," *J. Biol. Chem.* 277(14):8161-8169, 1996.
Parker et al., "Early Induction of Apoptosis in Hematopoietic Cell Lines After Exposure to Flavopiridol," *Blood* 91:458-465, 1998.
Parry et al., "Dinaciclib (SCH 727965), a Novel and Potent Cyclin-Dependent Kinase Inhibitor," *Molecular Cell Therapy* 9:2344-2353, 2010.
Paruch et al., "Discovery of Dinaciclib (SCH 727965): A Potent and Selective Inhibitor of Cyclin-Dependent Kinases," *ACS Medicinal Chemistry Letters* 1:204-208, 2010.
Payne et al., "Identification of the regulatory phosphorylation sites in pp42/mitogen-activated protein kinase (MAP kinase)," *The EMBO Journal* 10(4):885-892, 1991.
Pepper et al., "Flavopiridol circumvents Bcl-2 family mediated inhibition of apoptosis and drug resistance in B-cell chronic lymphocytic leukaemia," *Br. J. Haematol* 114(1):70-77, 2001.
Perkins et al., "Frequency and Type of Serious Infections in Fludarabine-Refractory B-Cell Chronic Lymphocytic Leukemia and Small Lymphocytic Lymphoma," *Cancer* 94:2033-2039, 2002.
Phillips et al., "Loss in MCL-1 function sensitizes non-Hodgkin's lymphoma cell lines to the BCL-2-selective inhibitor venetoclax (ABT-199)," *Blood Cancer J.* 5:e368, 2015. (8 pages).
Picaud et al., "PFI-1, a Highly Selective Protein Interaction Inhibitor Targeting BET Bromodomains," *Cancer Research* 73:3336-3346, 2013.
Piekarz et al., "Inhibitor of histone deacetylation, depsipeptide (FR901228), in the treatment of peripheral and cutaneous T-cell lymphoma: a case report," *Blood* 98:2865-2868, 2001.
Pierceall et al., "BH3 Profiling Discriminates Response to Cytarabine-Based Treatment of Acute Myelogenous Leukemia," *Mol. Cancer. Ther.* 72(12):2940-2949, 2013.
Pierceall et al., "Mcl-1 Dependence Predicts Response to Vorinostat and Gemtuzumab Ozogamicin in Acute Myeloid Leukemia," *Leuk Res* 38:564-568, 2014. (13 pages).
Pierceall et al., "Mitochondrial Priming of Chronic Lymphocytic Leukemia Patients Associates Bcl-$x_L$ Dependence with Alvocidib Response," *Leukemia* 28:2251-2254, 2014. (7 pages).
Pinckert et al., "An albumin enhancer located 10 kb upstream functions along with its promoter to direct efficient, liver-specific expression in transgenic mice," *Genes and Dev* 1:268-276, 1987.
Plumb et al., "Pharmacodynamic Response and Inhibition of Growth of Human Tumor Xenografts by the Novel Histone Deacetylase Inhibitor PXD101," *Molecular Cancer Therapeutics* 2:721-728, 2003.
Pode-Shakked et al., "Developmental tumourigenesis: NCAM as a putative marker for the malignant renal stem/progenitor cell population," *J. Cell. Mol. Med.* 13(8b):1792-1808, 2009.
Polster et al., "BH3 Death Domain Peptide Induces Cell Type-selective Mitochondrial Outer Membrane Permeability," *The Journal of Biological Chemistry* 276:37887-37894, 2001.
Presta, "Antibody engineering," *Curr. Op. Struct. Biol.* 2:593-596, 1992.
Pritzker, "Cancer Biomarkers: Easier Said Than Done," *Clinical Chemistry* 48:1147-1150, 2002.
Putcha et al., "Induction of BIM, a Proapoptotic BH3-Only BCL-2 Family Member, is Critical for Neuronal Apoptosis," *Neuron* 29(3):615-628, 2001.
Puthalakath et al., "Bmf: A Proapoptotic BH3-Only Protein Regulated by Interaction with the Myosin V Actin Motor Complex, Activated by Anoikis," *Science* 293:1829-1832, 2001.
Puthalakath et al., "Keeping killers on a tight leash: transcriptional and post-translational control of the pro-apoptotic activity of BH3-only proteins," *Cell Death Differ.* 9:505-512, 2002.
Puthalakath et al., "The Proapoptotic Activity of the Bcl-2 Family Member Bim is Regulated by Interaction with the Dynein Motor Complex," *Mol. Cell.* 3:287-296, 1999.
Quinsay et al., "Abstract 1783: Proapoptotic Bnip3 Mediates Permeabilization of Mitochondria and Release of Cytochrome c via a Novel Mechanism," *Circulation* 118(18): Supply 2, S388, 2008—Abstract.
Raff, "Social controls on cell survival and cell death," *Nature* 356:397-400, 1992.

(56) References Cited

OTHER PUBLICATIONS

Rassenti et al., "ZAP-70 Compared with Immunoglobulin Heavy-Chain Gene Mutation Status as a Predictor of Disease Progression in Chronic Lymphocytic Leukemia," *N. Engl. J. Med.* 351:893-901, 2004.
Ravandi et al., "Evaluating measurable residual disease in acute myeloid leukemia," *Blood Adv.* 2(11):1356-1366, 2018, (23 pages).
Ray et al., "BNIP3 Heterodimerizes with Bcl-2/Bcl-$x_L$ and Induces Cell Death Independent of a Bcl-2 Homology 3 (BH3) Domain at Both Mitochondrial and Nonmitochondrial Sites," *J. Biol. Chem.* 275(2):1439-1448, 2000.
Raychaudhuri, "Low probability Bid-Bax reaction generates heterogeneity in apoptosis resistance of cancer and cancer stem cells," arXiv:1108.2091 [q-bio.MN], 2011.
Ren et al., "BID, BIM, and PUMA Are Essential for Activation of the BAX- and BAK-Dependent Cell Death Program," *Science* 330:1390-1393, 2010.
Rezaei et al., "Leukemia markers expression of peripheral blood vs. bone marrow blasts using flow cytometry," *Med Sci. Monit* 9:CR359-CR362, 2003.
Richon et al., "A class of hybrid polar inducers of transformed cell differentiation inhibits histone deacetylases," *Proc. Natl. Acad. Sci. USA* 95:3003-3007, 1998.
Riechmann et al., "Reshaping human antibodies for therapy," *Nature* 332:323-327, 1988.
Rollins-Raval et al., "The value of immunohistochemistry for CD14, CD123, CD33, myeloperoxidase and CD68R in the diagnosis of acute and chronic myelomonocytic leukaemias," *Histopathology* 60:933-942, 2012.
Rothbard et al., "Conjugation of arginine oligomers to cyclosporine A facilitates topical delivery and inhibition of inflammation," *Nat. Med.* 6(11):1253-1257, 2000.
Rudek et al., "Clinical Pharmacology of Flavopiridol Following a 72-Hour Continuous Infusion," *Ann Pharmacother* 37:1369-1374, 2003.
Ruef et al., "Flavopiridol Inhibits Smooth Muscle Cell Proliferation in Vitro and Neointimal Formation in Vivo After Carotid Injury in the Rat," *Circulation* 100(6):659-665, 1999.
Ruef et al., "Induction of vascular endothelial growth factor in balloon-injured baboon arteries," *Circ. Res.* 81:24-33, 1997.
Ruef et al., "Induction of rat aortic smooth muscle cell growth by the lipid peroxidation product 4-hydroxy-2-nonenal," *Circulation* 97:1071-1078, 1998.
Ryan et al., "Heightened mitochondrial priming is the basis for apoptotic hypersensitivity of CD4$^+$CD8$^+$thymocytes," *Proc. Natl. Acad. Sci USA* 107(29):12895-12900, 2010.
Ryan et al., "BH3 Profiling in Whole Cells by Fluorimeter or FACS," *Methods* 61:156-164, 2013. (22 pages).
Saito et al., "A synthetic inhibitor of histone deacetylase, MS-27-275, with marked in vivo antitumor activity against human tumors," *Proc. Natl. Acad. Sci. USA* 96:4592-4597, 1999.
Samson et al., "A 35 amino acid fragment of leptin inhibits feeding in the rat," *Endocrinology* 137:5182-5185, 1996.
Sata et al., "Fas ligand gene transfer to the vessel wall inhibits neointima formation and overrides the adenovirus-mediated T cell response," *Proc. Natl. Acad. Sci. USA* 95:1213-1217, 1998.
Sattler et al., "Structure of Bcl-$x_L$-Bak Peptide Complex: Recognition Between Regulators of Apoptosis," *Science* 275:983-986, 1997.
Sausville et al., "Inhibition of CDKs as a Therapeutic Modality," *Ann NY Acad of Sci* 910:207-222, 2000.
Schimmer et al., "The BH3 domain of BAD fused to the Antennapedia peptide induces apoptosis via its alpha helical structure and independent of Bcl-2," *Cell Death and Differentiation* 8:725-733, 2001.
Schwartz et al., "Phase II Study of the Cyclin-Dependent Kinase Inhibitor Flavopiridol Administered to Patients With Advanced Gastric Carcinoma," *J. Clin. Onc.* 19:1985-1992, 2001.
Schwartz et al., "The intima: soil for atherosclerosis and restenosis," *Circ. Res.* 77:445-465, 1995.

Seal et al., "Identification of a novel series of BET family bromodomain inhibitors: binding mode and profile of I-BET151 (GSK1210151A)," *Bioorg. Med. Chem. Lett* 22:2968-2972, 2012.
Sedlacek et al., "Flavopiridol (L86 8275; NSC 649890), a new kinase inhibitor for tumor therapy," *International Journal of Oncology* 9:1143-1168, 1996.
Sen et al., "Artemisinin triggers induction of cell-cycle arrest and apoptosis in *Leishmania donovani* promastigotes," *J Med Microbiol* 56(Pt. 9):1213-1218, 2007.
Senderowicz et al., "Phase I Trial of Continuous Infusion Flavopiridol, a Novel Cyclin-Dependent Kinase Inhibitor, in Patients with Refractory Neoplasms," *J. Clin Onc* 16:2986-2999, 1998.
Senderowicz et al., "Preclinical and Clinical Development of Cyclin-Dependent Kinase Modulators," *J Natl Cancer Inst* 92:376-387, 2000.
Senderowicz, "Flavopiridol: the first cyclin-dependent kinase inhibitor in human clinical trials," *Investigational New Drugs* 17:313-320, 1999.
Score, "Search Results Details for U.S. Appl. No. 11/789,557 and Search Result 20091106_104627_ . . . ," dated Nov. 24, 2009, URL=http://es/ScoreAccessWeb/GetItem.action?AppId=11789557&seqId=09323b6780cf451a&ItemN . . . , 4 pages.
Shalaby et al., "Development of humanized bispecific antibodies reactive with cytotoxic lymphocytes and tumor cells overexpressing the HER2 protooncogene," *J Exp. Med.* 175:217-225, 1992.
Shangary et al., "Peptides derived from BH3 domains of Bcl-2 family members: a comparative analysis of inhibition of Bcl-2, Bcl-$x_L$ and Bax oligomerization, induction of cytochrome c release, and activation of cell death," *Biochemistry* 47:9485-9495, 2002.
Shapiro et al., "A Phase II Trial of the Cyclin-dependent Kinase Inhibitor Flavopiridol in Patients with Previously Untreated Stage IV Non-Small Cell Lung Cancer," *Clinical Cancer Research* 7:1590-1599, 2001.
Shibue et al., "Differential contribution of Puma and Noxa in dual regulation of p53-mediated apoptotic pathways," *The EMBO Journal* 25:4952-4962, 2006.
Shimizu et al., "Proapoptotic BH3-only Bcl-2 family members induce cytochrome c release, but not mitochondrial membrane potential loss, and do not directly modulate voltage-dependent anion channel activity," *PAAS* 97:577-582, 2000.
Shopes, "A genetically engineered human IgG mutant with enhanced cytolytic activity," *J. Immunol* 148:2918-2922, 1992.
Sinicrope et al., "Proapoptotic Bad and Bid Protein Expression Predict Survival in Stages II and III Colon Cancers," *Clin. Canc. Res.* 14(13):4128-4133, 2008.
Sinicrope et al., "Prognostic Impact of Bim, Puma, and Noxa Expression in Human Colon Carcinomas," *Clin. Canc. Res.* 14(18):5810-5818, 2008.
Sirois et al., "Antisense oligonucleotide inhibition of PDGFR-beta receptor subunit expression directs suppression of intimal thickening," *Circulation* 95:669-676, 1997.
Smith et al., "An alvocidib-containing regimen is highly effective in AML patients through a mechanism dependent on MCL1 expression and function," *2015 ASCO Annual Meeting*, Abstract No. 7062, 2015. (3 pages).
Smith et al., "Enhancer biology and enhanceropathies," *Nature Structural & Molecular Biology* 21:210-219, 2014.
Soltow et al., "Overexpression of CuZnSOD or MnSOD protects satellite cells from doxorubicin-induced apoptosis," *FASEB J* 21:A449, 2007—Abstract.
Song et al., "Carbon monoxide promotes Fas/CD95-induced apoptosis in Jurkat cells," *J. Biol Chem* 279(43):44327-44334, 2004. Erratum in: *J Biol Chem* 280(23):22555-22556, 2005.
Song et al., "Carbon Monoxide Promotes Fas/CD95-Induced Apoptosis in Jurkat Cells," *J. Biol Chem* 279(43):44327-44334, 2004—"Additions and Corrections," *J. Biol Chem* 280(23):22555-22556, 2005.
Stevenson et al., "A chimeric antibody with dual Fc regions (bisFabFc) prepared by manipulations at IgG hinge," *Anti-Cancer Drug Design* 3:219-230, 1989.
Stewart et al., "The MCL-1 BH3 Helix is an Exclusive MCL-1 inhibitor and Apoptosis Sensitizer," *Nat. Chem. Biol.* 6(8):595-601, 2010.

(56) References Cited

OTHER PUBLICATIONS

Sturm et al., "Mutation of p53 and consecutive selective drug resistance in B-CLL occurs as a consequence of prior DNA-damaging chemotherapy," Cell Death and Differentiation 10:477-484, 2003.
Sugiyama et al., "Activation of mitochondrial voltage-dependent anion channel by a pro-apoptotic BH3-only protein Bim," Oncogene 21(32):4944-4956, 2002.
Suzuki et al., "Possible Existence of Common Internalization Mechanisms among Arginine-rich Peptides," J. Biol Chem 277:2437-2443, 2002.
Tahir et al., "Potential mechanisms of resistance to venetoclax and strategies to circumvent it," BMC Cancer 17:399, 2017. (10 pages).
Tan et al., "Phase I Clinical and Pharmacokinetic Study of Flavopiridol Administered as a Daily 1-Hour Infusion in Patients with Advanced Neoplasms," J Clin Oncol 20:4074-4082, 2002.
Taussig et al., "Anti-CD38 antibody-mediated clearance of human repopulating cells masks the heterogeneity of leukemia-initiating cells," Blood 112(3):568-575, 2008.
Terradillos et al., "Direct addition of BimL to mitochondria does not lead to cytochrome c release," FEBS Lett 522(1-3):29-34, 2002.
Theisen et al., "Reversible inhibition of lysine specific demethylase 1 is a novel anti-tumor strategy for poorly differentiated endometrial carcinoma," BMC Cancer 14:752, 2014, 12 pages.
Thomenius et al., "Using BH3 Profiling as a Predictive Indicater for Myeloma Patient Response to Bortezomib," Blood 118(21): Abstract No. 3952, 2011.
Thornton et al., "Characterisation of TP53 abnormalities in chronic lymphocytic leukaemia," The Hematology Journal 5:47-54, 2004.
Thornton et al., "High dose methylprednisolone can induce remissions in CLL patients with p53 abnormalities," Ann Hematol 82:759-765, 2003.
Tolero Pharmaceuticals, "Jefferies 2016 Heathcare Conference," 2016, 31 pages.
Toogood et al., "Discovery of a Potent and Selective Inhibitor of Cyclin-Dependent Kinase 4/6," J. Med. Chem. 48:2388-2406, 2005.
Touzeau et al., "BH3-profiling identifies heterogeneous dependency on Bcl-2 family members in multiple myeloma and predicts sensitivity to BH3 mimetics," Leukemia 30:761-764, 2016.
Traunecker et al., "Bispecific single chain molecules (Janusins) target cytotoxic lymphocytes on HIV infected cells," EMBO J 10:3655-3659, 1991.
Tsao et al., "Concomitant inhibition of DNA methyltransferase and BCL-2 protein function synergistically induce mitochondrial apoptosis in acute myelogenous leukemia cells," Ann Hematol 91(12):1861-1870, 2012.
Tutt et al., "Trispecific F(ab')$_3$ derivatives that use cooperative signaling via the TCR/CD3 complex and CD2 to activate and redirect resting cytotoxic T cells," J. Immunol 147:60-69, 1991.
U.S. National Library of Medicine, "Flavopiridol in Treating Patients With Previously Treated Chronic Lymphocytic Leukemia or Lymphocytic Lymphoma," Apr. 9, 2003, URL=https://www.clinicaltrials.gov/ct2/show/NCT00058240?term=alvocidib&rank=16, retrieved Dec. 11, 2018, 9 pages.
U.S. National Library of Medicine, "Flavopiridol in Treating Patients With Relapsed or Refractory Lymphoma or Multiple Myeloma," Jun. 3, 2005, URL=https://www.clinicaltrials.gov/ct2/show/record/NCT00112723?term=alvocidib&rank=8, retrieved Dec. 11, 2018, 13 pages.
Valencia et al., "A new reliable fluorescence in situ hybridization method for identifying multiple specific cytogenetic abnormalities in acute myeloid leukemia," Leukemia & Lymphoma 51(4):680-685, 2010.
Vaquero et al., "Extracellular matrix proteins protect pancreatic cancer cells from death via mitochondrial and nonmitochondrial pathways," Gastroenterology 125(4):1188-1202, 2003.
Vaux et al., "Bcl-2 gene promotes haemopoietic cell survival and cooperates with c-myc to immortalize pre-B cells," Nature 335(6189):440-442, 1988.
Venkat, "Flavopiridol: A Drug that May Save Lives," 2004, retrieved from https://web.archive.org/web/20060615112217/http://clltopics.org/Chemo/flavopiridol.htm, 7 pages.
Venugopal et al., "A Phase I Study of Quisinostat (JNJ-26481585), an Oral Hydroxamate Histone Deacetylase Inhibitor with Evidence of Target Modulation and Antitumor Activity, in Patients with Advanced Solid Tumors," Clinical Cancer Research 19:4262-4272, 2013.
Verhoeyen et al., "Reshaping Human Antibodies: Grafting an Antilysozyme Activity," Science 239:1534-1536, 1988.
Ververis et al., "Histone deacetylase inhibitors (HDACIs): multitargeted anticancer agents," Biologies: Targets and Therapy 7:47-60, 2013.
Villela et al., "Acute Myeloid Leukaemia: Optimal Management and Recent Developments," Drugs 71(12):1537-1550, 2011.
Vitetta et al., "Redesigning Nature's Poisons to Create Anti-Tumor Reagents," Science 238:1098-1104, 1987.
Vives et al., "A Truncated HIV-1 Tat Protein Basic Domain Rapidly Translocates through the Plasma Membrane and Accumulates in the Cell Nucleus," J. Biol. Chem. 272(25):16010-16017, 1997.
Vo et al., "Relative Mitochondrial Priming of Myeloblasts and Normal HSCs Determines Chemotherapeutic Success in AML," Cell 151:344-355, 2012.
Vo, "Mitochondrial Priming Determines Chemotherapeutic Response in Acute Myeloid Leukemia," Dissertation, Harvard University, 119 pages, Apr. 5, 2012.
Wang et al., "Bid: A Novel BH3 Domain-Only Death Agonist," Genes & Development 10(22):2859-2869, 1996.
Wang et al., "Cell Permeable Bcl-2 binding peptides: A Chemical Approach to Apoptosis Induction in Tumor Cells," Cancer Res. 60:1498-1502, 2000.
Wang et al., "Structure based discovery of an organic compound that binds Bcl-2 protein and induces apoptosis of tumor cells," PNAS 97:7124-7129, 2000.
Wang et al., "Synthesis of pochoxime prodrugs as potent HSP90 inhibitors," Bioorganic & Medicinal Chemistry Letters 19:3836-3840, 2009.
Wang, "The Expanding Role of Mitochondria in Apoptosis," Genes Dev 15:2922-2933, 2001.
Wei et al., "Proapoptotic BAX and BAK: A Requisite Gateway to Mitochondrial Dysfunction and Death," Science 292(5517):727-730, 2001.
Wei et al., "tBID, a membrane-targeted death ligand, oligomerizes BAK to release cytochrome c," Genes & Development 14:2060-2071, 2000.
Wei et al., "Temporally and spatially coordinated expression of cell cycle regulatory factors after angioplasty," Circ. Res. 80:418-426, 1997.
Weinstein et al., "Addiction to Oncogenes—the Achilles Heal to Cancer," Science 297:63-64, 2002.
Weniger et al., "Treatment-Induced Oxidative Stress and Cellular Antioxidant Capacity Determine Reponse to Bortezomib in Mantle Cell Lymphoma," Clin. Cancer Res. 17(15):5101-5112, 2011.
Werner et al., "Bcl-2 Family Member Bfl-1/A1 Sequesters Truncated Bid to Inhibit its Collaboration With Pro-Apoptotic Bak or Bax," J. Biol. Chem 277(25):22781-22788, 2002.
Westerhoff et al., "Magainins and the distruption of membrane-linked free-energy transduction," Proc. Natl. Acad. Sci USA #86(17):6597-6601, 1989.
U.S. National Library of Medicine, "Ph I Study of Alvocidib and Cytarabine/Daunorubicin (7+3) in Patients With Newly Diagnosed Acute Myeloid Leukemia (AML)," ClinicalTrials.gov Identifier: NCT03298984, First Posted Oct. 2, 2017, Last Update Posted Mar. 14, 2019, retrieved from https://clinicaltrials.gov/ct2/show/study/NCT03298984, 8 pages.
Whatcott et al., "Alvocidib Potentiates the Activity of Venetoclax in Preclinical Models of Acute Myeloid Leukemia," Blood 128(22):1652, 2016.
Wilkinson, "Immunochemical techniques inspire development of new antibody purification methods," The Scientist 14(8):25-28, 2000.
Willis et al., "Apoptosis Initiated When BH3 Ligands Engage Multiple Bcl-2 Homologs, not Bax or Bak," Science 315:856-859, 2007.

(56) References Cited

OTHER PUBLICATIONS

Willis et al., "Proapoptotic Bak is sequestered by Mcl-1 and Bcl-xL, but not Bcl-2, until displaced by BH3-only proteins," *Genes Dev.* 19:1294-1305, 2005.
Wolff et al., "Monoclonal antibody homodimers: Enhanced antitumor activity in Nude Mice," *Cancer Research* 53:2560-2565, 1993.
Wolter et al., "Movement of Bax from the Cytosol to Mitochondria during Apoptosis," *J. Cell. Biol* 139(5):1281-1292, 1997.
Worland et al., "Alteration of the Phosphorylation State of p34cdc2 Kinase by the Flavone L86-8275 in Breast Carcinoma Cells: Correlation with Decreased H1 Kinase Activity," *Biochem. Pharmacol* 46:1831-1840, 1993.
Woyach et al., "Targeted therapies in CLL: mechanisms of resistance and strategies for management," *Blood* 126:471-477, 2015.
Wyatt et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crysallography and Structure Based Drug Design," *J. Med. Chem.* 51:4986-4999, 2008.
Yamaguchi et al., "Bcl-XL Protects BimEL-induced Bax Conformational Change and Cytochrome c Release Independent of Interacting with Bax or BimEL," *J. Biol. Chem* 277(44):41604-41612, 2002.
Yamauchi, "Incorporation of novel agents into the treatment for acute myeloid leukemia," *Rinsho Ketsueki* 59(10):1988-1996, 2018, (1 page) (English Abstract Only).
Yang et al., "Bad, a Heterodimeric Partner for Bcl-XL and Bcl-2, Displaces Bax Promotes Cell Death," *Cell* 80:285-291, 1995.
Yang et al., "Calculation of Protein Conformation from Circular Dichroism," *Methods Enzymol* 130:208-269, 1986.
Yang et al., "A novel liposomal formulation of flavopiridol," *International Journal of Pharmaceutics* 365:170-174, 2009.
Yang et al., "Bone marrow stroma-mediated resistance to FLT3 inhibitors in FLT3-ITD AML is mediated by persistent activation of extracellular regulated kinase," *British Journal of Haematology* 164:61-72, 2014.
Yasuda et al., "BNIP3α: aHuman Homolog of Mitochondrial Proapoptotic protein BNIP3," *Cancer Res.* 59:533-537, 1999.
Yeh et al., "Up-regulation of CDK9 kinase activity and Mcl-1 stability contributes to the acquired resistance to cyclin-dependent kinase inhibitors in leukemia," *Oncotarget* 6(5):2667-2679, 2014.
Yi et al., "Inhibition of Bid-induced apoptosis by Bcl-2. tBid insertion, Bax translocation, and Bax/Bak oligomerization suppressed," *J. Biol. Chem.* 278(19):16992-16999, 2003.
Yu et al., "Catalytic Site Remodelling of the DOT1L Methyltransferase by Selective Inhibitors," *Nat Commun* 3:1288, 2012.
Zeidner et al., "Randomized multicenter phase II study of flavopiridol (alvocidib), cytarabine, and mitoxantrone (FLAM) versus cytarabine/ daunorubicin (7+3) in newly diagnosed acute myeloid leukemia," *Haematologica* 100(9):1172-1179, 2015.
Zeng et al., "Targeting the leukemia microenvironment by CXCR4 inhibition overcomes resistance to kinase inhibitors and chemotherapy in AML," *Blood* 113:6215-6224, 2009.
Zha et al., "BH3 Domain of BAD is Required for Heterodimerization with Bcl-XL and Pro-apoptotic Activity," *J Biol. Chem.* 272(39):24101-24104, 1997.
Zha et al., "Posttranslational N-Myristoylation of BID as a Molecular Switch for targeting Mitochondria and Apoptosis," *Science* 290(5497):1761-1765, 2000.
Zha et al., "Serine Phosphorylation of Death Agonist BAD in Response to Survival Factor Results in Binding to 14-3-3 Not BCL-XL," *Cell* 87:619-628, 1996.
Zhai et al., "Clinical pharmacology and pharmacogenetics of flavopiridol 1-h i.v. infusion in patients with refractory neoplasms," *Anti-Cancer Drugs* 14:125-135, 2003.
Zhang et al., "Bcl-2 family proteins are essential for platelet survival," *Cell Death Differ.* 14(5):943-951, 2007.
Zhao et al., "The Making of I-BET762, a BET Bromodomain Inhibitor Now in Clinical Development," *Journal of Medicinal Chemistry* 56:7498-7500, 2013.

Zhou et al., "Flavopiridol enhances ABT-199 sensitivity in unfavourable-risk multiple myeloma cells in vitro and in vivo," *Br. J. Cancer* 118(3):388-397, 2018.
Zhou et al., "Novel mutant-selective EGFR kinase inhibitors against EGFR T790M," *Nature* 462(7276):1070-1074, 2009.
Zhu et al., "Development of venetoclax for therapy of lymphoid malignancies," *Drug Des. Devel. Ther.* 11:685-694, 2017.
Zong et al., "BH3-only prteins that bind pro-survival Bcl-2 family members fail to induce apoptosis in the absence of Bax and Bak," *Genes & Development* 15:1481-1486, 2001.
Belikov, "Pharmaceutical chemistry," *High School*, 1:43-47, Moscow, 1993 (English translation attached) (14 pages).
Besbes et al. "First MCL-1-selective BH3 mimetics as potential therapeutics for targeted treatment of cancer," *Cell Death and Disease* 6(7), 2015. (2 pages).
Chan et al., "Belinostat and panobinostat (HDACI): in vitro and in vivo studies in thyroid cancer," *J Cancer Res Clin Oncol* 139:1507-1514, 2013.
Chou et al., "Quantitative Analysis of Dose-Effect Relationships: The Combined Effects of Multiple Drugs or Enzyme Inhibitors," *Advances in Enzyme Regulation* 22:27-40, 1984.
Clinical Study, "Alvocidib, followed by cytarabine + mitoxantrone, makes impact in AML", *Inpharma Wkly* 1606:8, 2007. (Abstract).
Dawson, et al. "Inhibition of BET recruitment to chromatin as an effective treatment for MLL-fusion leukaemia" *Nature* 478:529-533, 2011.
Harkevich, "Pharmacology," *Medicine, Third Edition*:51-55, Moscow, 1987 (English translation attached) (10 pages).
Hewings et al., "Optimization of 3,5-Dimethylisoxazole Derivatives as Potent Bromodomain Ligands" *J. Med. Chem.*, 56:3217-3227, 2013.
Hollenbach et al., "A Comparison of Azacitidine and Decitabine Activities in Acute Myeloid Leukemia Cell Lines," *PLoS One* 5(2):e9001, 2010.
Itzykson et al., "Predicting the outcome of patients with higher-risk myelodysplastic syndrome treated with hypomethylating agents," *Leukemia & Lymphoma* 53(5):760-762, 2012.
Ji et al., "A Pharmacokinetic/Pharmacodynamic Model of Tumor Lysis Syndrome in Chronic Lymphocytic Leukemia Patients Treated with Flavopiridol," *Clinical Cancer Resarch* 19(5): 1269-1280, 2013.
Karp et al., "Randomized phase II study of two schedules of flavopiridol given as timed sequential therapy with cytosine arabinoside and mitoxantrone for adults with newly diagnosed, poor-risk acute myelogenous leukemia," *Haematologica* 97(11):1736-1742, 2012.
Kim et al., "The CDK9 Inhibitor, Alvocidib, Potentiates the Non-Clinical Activity of Azacytidine or Decitabine in an MCL-1-Dependent Fashion, Supporting Clinical Exploration of a Decitabine and Alvocidib Combination," Blood 132(Suppl. 1):4355, 2018, 6 pages.
Kim et al., "TP-1287, an oral prodrug of the cyclin-dependent kinase-9 inhibitor alvocidib", EHA Learning Center, Jun. 9, 2016, retrieved from https://library.ehaweb.org/eha/2016/21st/132440/clifford.whatcott.tp-1287.an.oral.prodrug.of.the.103cyclin-dependent.kinase-9.html, 2 pages.
Kimura, et al. "Antiproliferative and Antitumor Effects of Azacitidine Against Human Myelodysplastic Syndrome Cell Line SKM-1", Anticancer Research, 32:795-798 (2012).
Qi et al., "Abstract 2016: A subset of small cell lung cancer (SCLC) cell lines is Mcl-1-dependent and responds to cyclin-dependent kinase (cdk)9 inhibition in vitro and in vivo", *Cancer Research* 72:8 Suppl. 1, Abstract 2016, 2012. (4 pages).
Smith et al., "Abstract P047: Real-World Outcomes Among AML Patients Treated With Decitabine or Azachidine," *Haematologica* 98(Suppl 1):19, 2013.
Song et al., "Application of Flavopiridol, Novel Small Molecule Cyclin-Dependent Kinase Inhibitor, in Tumor Therapy" *National Medical Journal of China* 85(12): 862-864, 2005. (With English Translation) (10 Pages).
Stephens et. al., "Cyclophosphamide, alvocidib (flavopiridol), and rituximab, a novel feasible chemoimmunotherapy regimen for patients with high-risk chronic lymphocytic leukemia", *Leukemia Research* 37:1195-1199, 2013.

(56) References Cited

OTHER PUBLICATIONS

Tan et al., "The DNA methyltransferase inhibitor zebularine induces mitochondria-mediated apoptosis in gastric cancer cells in vitro and in vivo" *Biochemical and Biophysical Research Communications* 430:250-255, 2013.

Thomas et al., "Phase I Clinical and Pharmocokinetic Trial of Flavopiridol," *Proc of Annual Meeting of Amer Assoc* 38:Abstract 1496, 222, 1997.

U.S. National Library of Medicine, "Alvocidib, Cytarabine, and Mitoxantrone in Treating Patients With Newly Diagnosed Acute Myeloid Leukemia" Nov. 21, 2008, URL=https://clinicaltrials.gov/ct2/show/NCT00795002, retrieved Jan. 28, 2020, 11 pages.

U.S. National Library of Medicine, "History of Changes for Study: NCT01949883 A Phase 1 Study Evaluating CP1-0610 in Patients With Progressive Lymphoma" ClinicalTrials.gov Identifier: NCT01949883, First Posted Sep. 13, 2013, Last Update Posted Sep. 25, 2019, retrieved from https://clinicaltrials.gov/ct2/history/NCT01949883?A=2&B=2&C=merged#StudyPageTop, 7 pages.

Zeidner, et al., "Randomized Phase II Trial of Timed-Sequential Therapy (TST) with Flavopiridol (Alvocidib), Ara-C and Mitoxantrone (FLAM) Versus "7+3" for Adults Ages 70 Years and Under with Newly Diagnosed Acute Myeloid Leukemia (AML)," *Blood* 120:21, Abstract 47, 3 pages, 2012.

"Alvocidib Biomarker-driven Phase 2 AML Study," Sumitomo Dainippon Pharma Oncology, ClinicalTrials.gov identifier: NTC02520011, URL:https://www.clinicaltrials.gov/ct2/show/NCT02520011, Accessed: Dec. 31, 2020, 8 pages.

Akgul, C., "Mcl-1 is a Potential Therapeutic Target in Multiple Types of Cancer", Cell. Mol. Life Sci., 66:1326-1336 (2009).

Al-Mawali, "Leukemic Stem Cells Shows the Way for Novel Target of Acute Myeloid Leukemia Therapy", J Stem Cell Res Ther, 3(4):1-8 (2013).

Alvocidib, definition of alvocidib, NCI Dictionary of Cancer Terms—National Cancer Institute, retrieved from URL: https://www.cancer.gov/publications/dictionaries/cancer-terms/def/alvocidib on Jan. 7, 2021, 1 page.

Araki et al., "Allogeneic Hematopoietic Cell Transplantation for Acute Myeloid Leukemia: Time to Move Toward a Minimal Residual Disease-Based Definition of Complete Remission?" J Clin Oncol 34(4):329-336, 2016.

Attal, M., et al. , "Lenalidomide Maintenance after Stem-Cell Transplantation for Multiple Myeloma," The New England Journal of Medicine, 366:1782-1791 (2012).

Awan, F. T., et al., "A Phase I Clinical Trial of Flavopiridol Consolidation in Chronic Lymphocytic Leukemia Patients Following Chemoimmunotherapy", Ann Hematol, 95:1137-1143 (2016).

Belmar, J. and Fesik, S.W., "Small Molecule Mcl-1 Inhibitors for the Treatment of Cancer", Pharmacol Ther., 145:76-84 (2015).

Benyon, B., "FDA Grants Venclexta an Accelerated Approval for AML Treatment", Nov. 21, 2018, 2 pages, URL: https://www.curetoday.com/articles/fda-grants-venclexta-an-accelerated-approval-for-aml-treatment.

Berge, et al., "Pharmaceutical Salts", Journal of Pharmaceutical Sciences 66(1):1-19 (1997).

Billard, C., "BH3 Mimetics: Status of the Field and New Developments", Mol Cancer Ther, 12(9):1671-1700 (2013).

Blum, W., et al., "Phase 1 Clinical and Pharmacokinetic Study of a Novel Schedule of Flavopiridol in Relapsed and Refractory Acute Leukemias", Haematologica, 95(7):1098-1105 (2010).

Boffo et al., "CDK9 Inhibitors in Acute Myeloid Leukemia," Journal of Experimental & Clinical Cancer Research, 37(36):1-10, 2018.

Bradbury, et al., "Optimisation of a Series of Bivalent Triazolopyridazine Base Bromodomain and Exterminal Inhibitors: The Discovery of (3R)-4-[2-[4-[1-(3-methoxy-[1,2,4]triazolo[4,3-b]pyridazin-6-yl)-4-piperidyl]phenoxy]ethyl]-1,3-dimethyl-piperzin-2-one (AZD5153)", Journal of Medicinal Chemistry, 59(17):7801-7817 (2016).

Brüsselbach, et al., "Cell Cycle-Independent Induction of Apoptosis by the Anti-Tumor Drug Flavopiridol in Endothelial Cells", Int. J. Cancer, 77:146-152 (1998).

Burrer et al., "Selective Peptide Inhibitors of Antiapoptotic Cellular and Viral Bcl-2 Proteins Lead to Cytochrome C Release During Latent Kaposi's Sarcoma-Associated Herpesvirus Infection," Virus Res. 211:86-88, 2016. (Author's manuscript).

Byrd, et al., "Pretreatment cytogenetic abnormalities are predictive of induction success, cumulative incidence of relapse, and overall survival in adult patients with de novo acute myeloid leukemia: results from Cancer and Leukemia Group B (CALGB 8461)" Blood, 100(13): 4325-4336 (2002).

CAS Registry No. 951209-71-5, "IRX 2" Entered STN Oct. 23, 2007, 1 page.

Chen, C., et al., "Lenalidomide in Multiple Myeloma—a Practice Guideline", Curr Oncol, 20(2):e136-e149 (2013).

Chen, et al., "Androgen Receptor Serine 81 Phosphorylation Mediates Chromatin Binding and Transcriptional Activation", Journal of Biological Chemistry, 287(11):8571-8583 (2012).

Christian, B. A., et al., "Flavopiridol in Chronic Lymphocytic Leukemia: A Concise Review," Clinical Lymphoma & Myeloma, 9(Suppl 3):S179-S185 (2009).

Common Terminology Criteria for Adverse Events (CTCAE) Version 5.0 Publichsed: Nov. 7, 2017 U.S. Department of Health and Human Services, National Institutes of Health, National Cancer Institute, URL=https://ctep.cancer.gov/protocoldevelopment/electronic_applications/docs/CTCAE_v5_Quick Reference Accessed: Dec. 31, 2020, 147 pages.

Corbett, et al., "Evaluation of Single Agents and Combinations of Chemotherapeutic Agents in Mouse Colon Carcinomas", Cancer 40:2660-2680 (1987).

Corbett, et al., "Response to Transplantable Tumors of Mice to Antracenedione Derivatives Alone and in Combination with Clinically Useful Agents", Cancer Treatment Reports 66:1187-1200 (1982).

Dang, "MYC on the Path to Cancer," Cell 149(1):22-35, 2012. (28 pages).

De Haas et al., "Initial Diagnostic Work-up of Acute Leukemia: ASCO Clinical Practice Guideline Endorsement of the College of American Pathologists and American Society of Hematology Guideline," J Clin Oncol 37(3):239-253, 2018.

Dehm, et al., "Alternatively Spliced Androgen Receptor Variants", Endocrine—Related Cancer, 18(5):R183-R196 (2011).

Dillman, R.O., et al., "A Comparative Study of Two Different Doses of Cytarabine for Acute Myeloid Leukemia: A Phase III Trial of Cancer and Leukemia Group B", Blood, 78(10):2520-2526 (1991).

Dimopoulos et al., "Multiple Myeloma: EAH-ESMO Clinical Practice Guidelines for Diagnosis, Treatment and Follow-up," Annals of Oncology 32(3):309-322, 2021.

DiNardo, C.D., et al., "Venetoclax Combined with Decitabine or Azacitidine in Treatment-Naïve, Elderly Pations With Acute Myeloid Leukemia", Blood, 133:7-17 (2019).

Dittmann, et al., "The Commonly Used P13-Kinase Probe LY294002 is an Inhibitor of BET Bromodomains", ACS Chem. Biol., 9(2):495-502 (2014).

Döhner et al., "Diagnosis and Management of AML in Adults: 2017 ELN Recommendations From an International Expert Panel," Blood 129(4):424-447, 2017.

Döhner, H., et al., "Acute Myeloid Leukemia", The New England Journal of Medicine, 373(12), 1136-1152 (2015).

Eichhorst et al., "Chronic Lymphocytic Leukaemia: ESMO Clinical Practice Guidelines for diagnosis, treatment and follow up," Annals of Oncology 32(1):23-33, 2020.

Evans, "Clathrate Compouns" in an Introduction to Crystal Chemistry, (London:Cambridge University Press), pp. 393-397 (1964).

Fenaux et al., "Myelodysplastic syndromes: ESMO Clinical Practice Guidelines for diagnosis, treatment and follow-up," Annals of Oncology 25(Supplement 3):iii57-iii69, 2014.

Ferrara, et al., "Consensus-Based Definition of Unfitness to Intensive and Nonintensive Chemotherapy in Acute Myeloid Leukemia: a Project of SIE, SIES and GITMO Group on a New Tool for Therapy Decision Making", Leukemia, 27:997-999 (2013).

Freeman et al., "Measurable Residual Disease at Induction Redefines Partial Response in Acute Myeloid Leukemia and Stratifies Outcomes in Patients at Standard Risk Without NPM1 Mutations," J Clin Oncol 36(15):1486-1497, 2018, (24 pages).

(56) References Cited

OTHER PUBLICATIONS

Freeman et al., "Prognostic Relevance of Treatment Response Measured by Flow Cytometric Residual Disease Detection in Older Patients with Acute Myeloid Leukemia," J Clin Oncol 31(32):4123-4131, 2013.
Gambella et al., "Minimal Residual Disease by Flow Cytometry and Allelic-Specific Oligonucleotide Real-Time Quantitative Polymerase Chain Reaction in Patients With Myeloma Receiving Lenalidomide Maintenance: A Pooled Analysis," Cancer 125:750-760, 2019.
Gao et al., "Multiple Myeloma Cancer Stem Cells," Oncotarget 7(23):35466-35477, 2016.
George, B., et al., "A Phase I, First-in-Human, Open-Label, Dose-Escalation, Safety, Pharmacokinetic, and Pharmacodynamic Study of Oral TP-1287 Administered Daily to Patients with Advanced Solid Tumors", Journal of Clinical Oncology, 38(15) Abstract 3611—3 pages (2020).
Gerber, et al., A Clinically Relevant Population of Leukemic CD34+ CD38—Cells in Acute Myeloid Leukemia, Blood, 119(15):3571-3577 (2012).
Hamid, et al., "Safety and Tumor Responses with Lambrolizumab (Anti-PD-1) in Melanoma", The New England Journal of Medicine, 369(2):134-144 (2013).
"Hematologic Malignancies: Regulatory Considerations for Use of Minimal Residual Disease in Development of Drug and Biological Products for Treatment, Guidance for Industry," U.S. Department of Health and Human Services, Food and Drug Administration, Oncology Center of Excellence (OCE), Center for Drug Evaluation and Research (CDER), Center for Biologies Evaluation and Research (CBER), Jan. 2020, available from https://www.fda.gov/media/134605/download. 21 pages.
Heuser et al., "Acute Myeloid Leukaemia in Adult Patients: ESMO Clinical Practice Guidelines for diagnosis, treatment and follow-up," Annals of Oncology 31(6):697-712, 2020.
Hillengass et al., "Minimal Residual Disease in Multiple Myeloma: Use of Magnetic Resonance Imaging," *Seminars in Hematology* 55(1):19-21, 2018. (Abstract Only).
Hoelzer et al., "Acute Lymphoblastic Leukaemia in adult patients: ESMO Clinical Practice Guidelines for diagnosis, treatment, and follow-up" Annals of Oncology 27(Supplement 5):v69-v82, 2016.
Hourigan, et al., "Development of Therapeutic Agents for Older Patients with Acute Myelogenous Leukemia", Current Opinion in Investigational Drugs, 11(6):669-677 (2010).
Ivey et al., "Assessment of Minimal Residual Disease in Standard-Risk AML," The New England Journal of Medicine, 374(5):422-433, 2016.
Jongen-Lavrencic et al., "Molecular Minimal Residual Disease in Acute Myeloid Leukemia," The New England Journal of Medicine, 378(13):1189-1199, 2018.
Karp, et al., Phase I and Pharmacokinetic Study of Bolus-Infusion Flavopiridol Followed by Cytosine arabinoside and mitoxantrone for Acute Leukemias:, Blood, 117(12):3302-3310 (2011).
Kaur, et al., "Growth Inhibition with Reversible Cell Cycle Arrest of Carcinoma Cells by Flavone L86-8275,", JNCI, 22(84):1736-1740 (1992).
Kelland, L.R., "Flavopiridol, The First Cyclin-Dependent Kinase Inhibitor to Enter the Clinic: Current Status", Expert Opinion on Investigational Drugs, 9(12):2903-2911 (2000).
Kern et al., "Determination of Relapse Risk Based on Assessment of Minimal Residual Disease during Complete Remission by Multiparameter Flow Cytometry in Unselected Patients with Acute Myeloid Leukemia," Blood 104(10):3078-3085, 2004.
Kim et al., "Alvocidib Potentiates the Activity of Cytarabine and Mitoxantrone through the Targeting of MCL-1 When Administered in a Time Sequential Regimen in AML," Blood 126(23), 3799, 2015. (Abstract Only).
Kim, W., et al., "Alvocidib Potentiates the Activity of Azacytidine in an MCL-1-Dependent Fashion", Blood, 126(23):Abstract 1343, 3 pages (2015).

Klaeger, et al., "The Target Landscape of Clinical Kinase Drugs", Science, 358:1148-1164 (2017).
Knutson, et al., "Synergistic Anti-Tumor Activity of EZH2 Inhibitors and Glucocorticoid Receptor Agonists in Models of Germinal Center Non-Hodgkin Lymphomas", PLoS One, 9(12):e111840 (2014).
Konopleva et al., "BCL-2 Inhibition in AML: An Unexpected Bonus?" Blood 132(10):1007-1012, 2018.
Kumar, S., et al., "International Myeloma Working Group Consensus Criteria for Response and Minimal Residual Disease Assesment in Multiple Myeloma," Lancet Oncology, 17:e328-e346 (2016).
Landgren et al., "MRD Testing in Multiple Myeloma: The Main Future Driver for Modern Tailored Treatment," Seminars in Hematology 55(1):44-50, 2018. (Abstract Only).
Landgren, "MRD Testing in Multiple Myeloma: From a Surrogate Marker of Clinical Outcomes to an Every-Day Clinical Tool," Seminars in Hematology 55(1):1-3, 2018. (Abstract Only).
Lin, T.S., et al., "Phase II Study of Flavopiridol in Relapsed Chronic Lymphocytic Leukemia Demonstrating High Response Rates in Genetically High-Risk Disease", Journal of Clinical Oncology, 27(35):6012-6018 (2009).
Lindsley, R.C., et al., "Acute Myeloid Leukemia Ontogeny is Defined by Distinct Somatic Mutations", Blood, 125(9):1367-1376 (2015).
Londoño, et al., "A Reliable Method for Quantification of Splice Variants Using RT-qPCR", BMC Mol. Biol., 17(8):1-12 (2016).
Malcovati et al., "Diagnosis and Treatment of Primary Myelodysplastic Syndromes in Adults: Recommendations From the European LeukemiaNet," Blood 122(17):2943-2964, 2013.
Malumbres, "Cyclin-Dependent Kinases", Genome Biol., 15(122):1-10 (2014).
Matsumura, Y., et al., "1959-CDK9 Inhibition Combined with Hypomethylating Agents Target MCL-1 Dependency in MDS and AML", AACR Annual Meeting 2021—Virtual—Poster to be presented during Session PO.MCB06.01-Cell Cycle on Apr. 10, 2021, downloaded from AACR website, URL: https://www.abstractsonline.com/pp8/#!/9325/presentation/3238 on Mar. 30, 2021, 2 pages.
Mayer, "Induction of apoptosis by flavopiridol unrelated to cell cycle arrest in germ cell tumour derived cell lines," Invest New Drugs 23(3):205-211, 2005.
Mian, S.A., et al., "Splicesome Mutations Exhibit Specific Associations with Epigenetic Modifiers and Proto-Oncogenes Mutated in Myelodysplastic Syndrome", Haematologica, 98(7):1058-1066 (2013).
Mikhael et al., "Treatment of Multiple Myeloma: ASCO and CCO Joint Clinical Practice Guideline," J Clin Oncol 37(14):1228-1264, 2019. (40 pages).
Mintz G.S., "Arterial remodeling after coronary angioplasty: a serial intravascular ultrasound study", Circulation,; 94:35-43 (1996).
Mintz G.S., "In-stent restenosis: the Washington Hospital Center experience", Am. J. Cardiol., 81:7E-13E (1998).
Mirguet, O., et al., "Discovery of Epigenetic Regulator I-BET762: Lease Optimization to Afford a Clinical Candidate Inhibitor of the BET Bromodomains", Journal of Medicinal Chemistry, 56:7501-7515 (2013).
Montesinos, et al., "Tumor Lysis Syndrome in Patients with Acute Myeloid Leukemia: Identification of Risk Factors and Development of a Predictive Model", Haematologica, 93:67-74 (2008).
Moros, et al., "Synergistic Antitumor Activity of Lenalidomide with the BET Bromodomain Inhibitor CPI203 in Bortezomib-Resistant Mantle Cell Lymphoma", Leukemia, 28(10):2049-2059 (2015).
Motwani, M., et al., "Docetaxel and Navelbine Induced Apoptosis is Enhanced by Flavopiridol (Flavo) in Breast Cancer Cells and is Sequence Dependent", Proceedings of the American Association for Cancer Research, 41, p. 143, Abstract #912 (2000).
National Comprehensive Cancer Network® clinical practice guidelines for Acute Myeloid Leukemia version 2.2014 (2014).
NICE guidelines, "Myeloma: Diagnosis and Management," National Institute for Health and Care Excellence: 1-27, 2016.
Oken, et al., "Toxicity and Response Criteria of the Eastern Cooperative Oncology Group", Am. J. Clin. Oncol., 5(6):649-655 (1982).
Opferman, et al., "Obligate Role of Anti-Apoptotic MCL-1 in the Survival of Hematopoietic Stem Cells", Science, 307:1101-1104 (2005).

(56) References Cited

OTHER PUBLICATIONS

Pandit-Taskar, "Functional Imaging Methods for Assessment of Minimal Residual Disease in Multiple Myeloma: Current Status and Novel ImmunoPET Based Methods," Seminars in Hematology, 55(1):22-32, 2018 (Abstract Only).
Papaemmanuil et al., "Genomic Classification and Prognosis in Acute Myeloid Leukemia," The New England Journal of Medicine 374(23):2209-2221, 2016.
Parovichnikova, E., et al., "The MRD-Negativity Rate Measured by Flow Cytometry After the 1st and 2nd Induction Course Among CR AML Patients from Different Cytogenetic Subgroups Does Not Differ Though the Morphological CR Achievement Does", Blood, 132(Suppl1:1495, 6 pages (2018).
Perrot et al., "Minimal Residual Disease Negativity Using Deep Sequencing is a Major Prognostic Factor in Multiple Myeloma," Blood 132(23):2456-2464, 2018.
Phelps, et al., "Clinical Response and Pharmacokinetics from a Phase I Study of an Active Dosing Schedule of Flavopiridol in Relapsed Chronic Lymphocytic Leukemia", Blood, 113(12):2637-2645 (2009).
Picaud, et al., "RVX-208, an Inhibitor of BET Transcriptional Regulators with Selectivity for the Second Bromodomain", PNAS, 110(49):19754-19759 (2013).
Pugh, "Circulating Tumour DNA for Detecting Minimal Residual Disease in Multiple Myeloma," Seminars in Hematology 55:38-40, 2018.
Ramsey, H.E., et al., "A Novel MCL1 Inhibitor Combined with Venetoclax Rescues Venetoclax-Resistant Acute Myelogenous Leukemia", Cancer Discov, 8(12):1566-1581 (2018).
Richard, D., et al.,"Hydroxyquinoline-derived compounds and analoguing of selective Mcl-1 inhibitors using a functional biomarker" Bioorg Med Chem. 21(21):6642-9, 2013.
Rosenblatt, et al., "PD-1 Blockade by CT-011, Anti PD-1 Antibody, Enhances Ex-Vivo T Cell Responses to Autologous Dendritic/Myeloma Fusion Vaccine", J. Immunother, 34(5):409-418 (2011).
Roshal, "Minimal Residual Disease Detection by Flow Cytometry in Multiple Myeloma: Why and How?" Seminars in Hematology 55(1):4-12, 2018 (Abstract Only).
Salomon, C.J., et al., "Recent Developments in Chemical Deprotection of Ester Functional Groups", Tetrahedron, 49(18):3691-3748 (1993).
San Miguel et al., "Early Immunophenotypical Evaluation of Minimal Residual Disease in Acute Myeloid Leukemia Identifies Different Patient Risk Groups and May Contribute to Postinduction Treatment Stratification," Blood 98(6):1746-1751, 2001.
Schuurhuis, et al., "Minimal/Measurable Residual Disease in AML: A Consensus Document from the Duropean LeukemiaNet MRD Working Party", Blood, 131(12):1275-1291 (2018).
Schwartz, G.K., et al., "Phase I Study of the cyclin-dependent kinase inhibitor flavopiridol in combination with paclitaxel in patients with advanced solid tumors", J. Clin. Oncol. Apr. 15, 2002; 20(8): 2157-21770.
Schwartz, G.K., et al., "Phase I Trial of Sequential Paclitaxel and Cisplatin in Combination with the Cyclin Dependent Kinase Inhibitor Flavopiridol (Flavo) in Patients with Advances Solid Tumors", Clinical Cancer Research, 5, p. 3754s, Abstract #122 (1999).
Szabo, C., "Understanding What Causes Relapse in Patients with Acute Myeloid Leukemia", Sep. 8, 2015, 3 pages. URL: https://www.pharmacytimes.com/ajax/understanding-what-cause-relpase-in-ptients-with-acute-myeloid-leukemia.
Tanaka, et al., "Design and Characterization of Bivalent BET Inhibitors", Nat. Chem. Biol., 12(12):1089-1096 (2016).
Terwijn et al., "High Prognostic Impact of Flow Cytometric Minimal Residual Disease Detection in Acute Myeloid Leukemia: Data From the HOVON/SAKK AML 42A Study," J Clin Oncol 31(31):3889-3897, 2013.
Thoren, "Mass Spectrometry Methods for Detecting Monoclonal Immunoglobulins in Multiple Myeloma Minimal Residual Disease," Seminars in Hematology 55(1):41-43, 2018 (Abstract Only).
Waldschmidt et al., "Comprehensive Characterization of Circulating and Bone Marrow-Derived Multiple Myeloma Cells at Minimal Residual Disease," Seminars in Hematology 55(1):33-37, 2018 (Abstract Only).
Xiang et al., "Mcl1 haploinsufficiency protects mice from Myc-induced Acute Myeloid Leukemia," J Clin Invest., 120(6):2109-2118, 2010.
Yanagisawa, et al., "Translating Leukemia Stem Cells into the Clinical Setting: Harmonizing the Heterogeneity", Experimental Hematology, 44(12):1130-1137 (2016).
Yoshimoto, et al., "FLT3-ITD up-Regulates MCL-1 to Promote Survival of Stem Cells in Acute Myeloid Leukemia via FLT3-ITD-Specific STAT5 Activation", Blood, 114(24):5034-5043 (2009).
Zeidener, J.F. and Karp, J.E., "Clinical Activity of Alvocidib (Flavopiridol) in Acute Myeloid Leukemia", Leukemia Research, 39:1312-1318 (2015).
Zeidner, J.F., et al., "Final Results of a Randomized Multicenter Phase II Study of Alvocidib, Cytarabine, and Mitoxantrone Versus Cytarabine and Daunorubicin (7+3) in Newly Diagnosed High-Risk Acute Myeloid Leukemia (AML)", Leukemia Research, 72:92-95 (2018).
Zeidner, J.F., et al., "Phase I Study of Alvocidib Followed by 7+3 (Cytarabine + Daunorubicin) in Newly Diagnosed Acute Myeloid Leukemia", Clin Cancer Res, 27:60-69 (2021).
Zeidner, J.F., et al., "Phase II Study Incorporating a Novel BH3-Profiling Biomarker Approach of Alvocidib Followed by Cytarabine and Mitoxantrone in Relapsed/Refractory Acute Myeloid Leukemia (AML)", Abstract PF243, 23rd European Hematology Association Congress, Stockholm Sweden Jun. 14-17, 2018.
Zeidner, J.F., et al., "Zella201: A Biomarker-Guided Phase II Study of Alvocidib Followed by Cytarabine and Mitoxantrone in MCL-1 Dependent Relapsed/Refractory Acute Myeloid Leukemia (AML)", Blood, 132(Suppl 1):6 pages (2018).
Zhao, et al., "BCL2 Amplicon Loss and Transcriptional Remodeling Drives ABT-199 Resistance in B Cell Lymphoma Models", Cancer Cell, 35:752-766 (2019).
Litzow, M.R., et al., "A randomized trial of three novel regimens for recurrent acute myeloid leukemia deomonstrates the continuing challenge of treating this difficult disease", Am. J. of Hematol, 94(1), 111-117, Jan. 2019.
Sommakia, S., et al., "Alvocidib Synergizes with BRD4 Inhibitors to Improve Cytotoxity in an AML Cell Line" Poster P255 presented at AACR-NCI-EORTC Virtual International Conference on Molecular Targets and Cancer Therapeutics, Oct. 7-10, 2021.
Yancey, D. et al., "BAD Dephosphorylation and Decreased Expression of MCL-1 Induce Rapid Apoptosis in Prostate Cancer Cells," PLOS, vol. 8; No. 9; e74561 (11 pages), Sep. 2013.

\* cited by examiner

ALVOCIDIB PRODRUGS AND THEIR USE AS PROTEIN KINASE INHIBITORS

This application is the U.S. National Stage of International Application No. PCT/US2017/062408, filed Nov. 17, 2017, which designates the U.S., published in English, and claims the benefit of U.S. Provisional Application No. 62/424,255, filed Nov. 18, 2016.

BACKGROUND

Technical Field

Embodiments of the present invention are generally directed to novel compounds having utility as prodrugs of alvocidib, and use of the same for inhibition of protein kinases, for example as a treatment for cancer.

Description of the Related Art

Cyclin-dependent kinases (CDKs) are important regulators that control the timing and coordination of the cell cycle. CDKs form reversible complexes with their obligate cyclin partners to control transition through key junctures in the cell cycle. For example, the activated CDK4-cyclin D1 complex controls progression through the G1 phase of the cell cycle, while the CDK1-cyclin B1 complex controls entry into the mitotic phase of the cell cycle. Endogenous cyclin dependent kinase inhibitory proteins (CDKIs) are known to bind either the CDK or cyclin component and inhibit the kinase activity of the complex. In many tumors such as melanomas, pancreatic and esophageal cancers, these natural CDKIs are either absent or mutated. Thus, selective CDK inhibitors may prove to be effective chemotherapeutic agents.

Alvocidib (also known as Flavopiridol) is a synthetic flavone having the following structure:

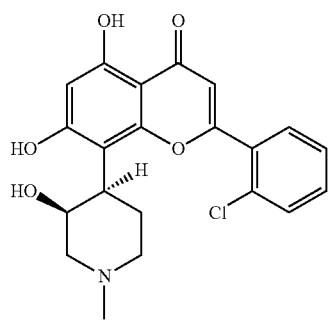 [SMILES: CN1CC[C@H](c2c(O)cc(O)c3c(=O)cc(-c4ccccc4Cl)oc23)[C@H](O)C1]

Alvocidib is a potent and selective inhibitor of the CDKs and has antitumor activity against various tumor cells lines, such as human lung carcinoma and breast carcinoma and also inhibits tumor growth in xenograft models. Alvocidib has been shown to induce arrest in both the G1 and G2 phases of the cell cycle and also inhibit polymerase II driven transcription by inhibiting CDK9. By inhibiting CDK9, which forms part of the complex known as the positive transcription elongation factor or P-TEFb, alvocidib treatment reduces the expression of key oncogenes such MYC and key anti-apoptotic proteins such as MCL1. Accordingly, alvocidib is an attractive therapeutic agent for cancer and is currently undergoing clinical trials in relapsed/refractory AML patients.

Oral administration of alvocidib has been limited by gastrointestinal toxicity and limited oral bioavailability. Further, preclinical studies suggest that prolonged exposure may be important for maximizing alvocidib's activity. Accordingly, continuous intravenous infusion schedules have been extensively explored in human trials. Alternative hybrid dosing, including an intravenous bolus dose followed by a slow infusion have also been explored, but to date there have been no reports of orally delivering a therapeutically effective amount of alvocidib.

While progress has been made, there remains a need in the art for increasing the oral bioavailability of alvocidib. The present invention fulfills this need and provides related advantages.

BRIEF SUMMARY

In brief, embodiments of the present invention provide compounds having utility as prodrugs of alvocidib. Accordingly, in one embodiment is provided a compound having the following structure (I):

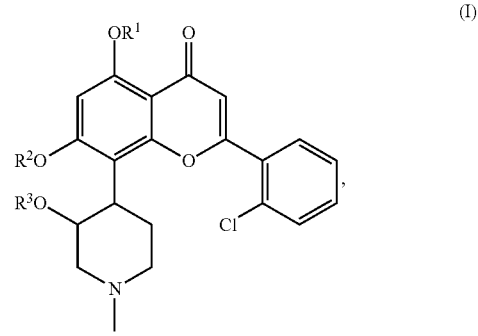

or a stereoisomer, tautomer or pharmaceutically acceptable salt thereof, wherein $R^1$, $R^2$ and $R^3$ are as defined herein, and at least one of $R^1$, $R^2$ and $R^3$ is not H.

Other embodiments are directed to a pharmaceutical composition comprising a pharmaceutically acceptable carrier or excipient and a compound of structure (I). Methods for use of the compound of structure (I), and pharmaceutical compositions comprising the same, for treatment of a disease associated with overexpression of a cyclin-dependent kinase (CDK) in a mammal in need thereof are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements may be enlarged and positioned to improve figure legibility.

Further, the particular shapes of the elements as drawn are not intended to convey any information regarding the actual shape of the particular elements, and have been solely selected for ease of recognition in the figures.

DETAILED DESCRIPTION

Figure 1A:
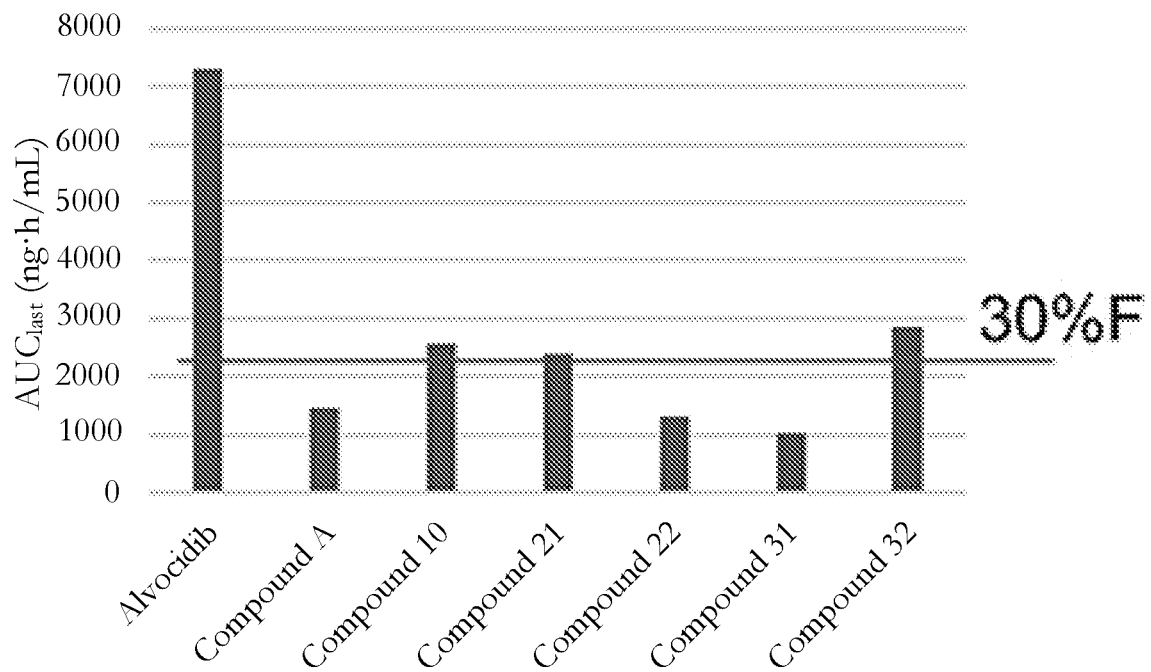
FIGS. 1A and B show alvocidib and parent prodrug exposure data for Compounds A, 10, 21, 22, 31, and 32, respectively FIGS. 2A and B show alvocidib and parent prodrug exposure data for Compounds 23-26, respectively FIGS. 3A and 3B alvocidib and parent prodrug exposure data for Compounds 27, 28 and 30, respectively

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Embodiments of the present invention include prodrugs of alvocidib. "Prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

A "compound of the invention" refers to a compound of structure (I), and its substructures, as defined herein.

Embodiments of the invention disclosed herein are also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Embodiments of the invention disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, embodiments of the invention include compounds produced by a process comprising administering a compound of this invention to a mammal for a period of time sufficient to yield a metabolic product thereof. Such products are typically identified by administering a radiolabeled compound of the invention in a detectable dose to an animal, such as rat, mouse, guinea pig, monkey, or to human, allowing sufficient time for metabolism to occur, and isolating its conversion products from the urine, blood or other biological samples.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, embodiments of the compounds of the present invention may exist as a hydrate, including a monohydrate, dihydrate, hemihydrate, sesquihydrate, trihydrate, tetrahydrate and the like, as well as the corresponding solvated forms. Embodiments of the compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Mammal" includes humans and both domestic animals such as laboratory animals and household pets (e.g., cats, dogs, swine, cattle, sheep, goats, horses, rabbits), and non-domestic animals such as wildlife and the like.

"Effective amount" or "therapeutically effective amount" refers to that amount of a compound of the invention which, when administered to a mammal, preferably a human, is sufficient to effect treatment, as defined below, of a disease associated with overexpression of a cyclin-dependent kinase (CDK) in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

"Alkyl" refers to a straight or branched hydrocarbon chain group consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless specifically stated otherwise, an alkyl group is optionally substituted.

"Aryl" refers to a hydrocarbon ring system group comprising hydrogen, 6 to 18 carbon atoms and at least one aromatic ring. For purposes of this invention, the aryl group may be a monocyclic, bicyclic, tricyclic or tetracyclic ring system, which may include fused or bridged ring systems. Aryl groups include, but are not limited to, aryl groups derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl groups that are optionally substituted.

"Amino" refers to the —$NH_2$ substituent.

"Alkoxy" refers to a radical of the formula —$OR_a$ where $R_a$ is an alkyl radical as defined above containing one to twelve carbon atoms or one to six carbon atoms. Unless stated otherwise specifically in the specification, an alkoxy group is optionally substituted.

"Alkylaminyl" refers to a radical of the formula —$N(R_a)(R_b)$ where $R_a$ is an alkyl radical as defined above containing one to twelve carbon atoms or one to six carbon atoms, and $R_b$ is H or an alkyl radical as defined above containing one to twelve carbon atoms or one to six carbon atoms. Unless stated otherwise specifically in the specification, an alkylaminyl group is optionally substituted.

"Alkyloxycarbonyl" refers to a radical of the formula —$C(=O)OR_a$ where $R_a$ is an alkyl radical as defined above containing one to twelve carbon atoms or one to six carbon atoms. Unless stated otherwise specifically in the specification, an alkyloxycarbonyl group is optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain is optionally substituted.

"Halo" refers to F, Cl, Br or I.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen, phosphorus and sulfur. Unless stated otherwise specifically in the specification, the heterocyclyl radical may be a monocyclic, bicyclic, tricyclic or tetracyclic ring system, which may include fused or bridged ring systems; and the nitrogen, carbon, phosphorus or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 5,5-dimethyl-1,3,2-dioxaphosphinane 2-oxidyl and 1,1-dioxo-thiomorpholinyl. Unless stated otherwise specifically in the specification, a heterocyclyl group may be optionally substituted.

"Hydroxyl" refers to the —OH radical.

"Phosphate" refers to the —OP(=O)(OH)$_2$ moiety. For ease of illustration the phosphate moieties herein are often depicted in the di-protonated form, but also exist in the mono-protonated (—OP(=O)(OH)(O$^-$)) and unprotonated forms (—OP(=O)(O$^-$)$_2$), depending on pH. The mono- and unprotonated forms will typically be associated with a counterion, such that the compounds are in the form of a pharmaceutically acceptable salt. Such mono- and unprotonated forms, and their pharmaceutically acceptable salts, are encompassed within the scope of the inventions, even if not specifically illustrated in the chemical structures.

"Polyalkyleneoxide" refers to a radical of the formula —O(R$_b$O)$_z$R$_a$ where R$_a$ is an alkyl radical as defined above containing one to twelve carbon atoms or one to six carbon atoms, R$_b$ is an alkylene chain as defined above, and z is an integer of 1 or more. Unless stated otherwise specifically in the specification, polyalkyleneoxide group is optionally substituted.

The term "substituted" used herein means any of the above groups (e.g., alkyl, alkoxy, alkylaminyl, alkoxycarbonyl, polyalkyleneoxide and/or aryl) wherein at least one hydrogen atom is replaced by a bond to a non-hydrogen atoms such as, but not limited to: a halogen atom such as F, Cl, Br, and I; a phosphate group such as the —OP(=O)(OH)$_2$; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, carbamates and nitriles. For example, "substituted" includes any of the above groups in which one or more hydrogen atoms are replaced with —NR$_x$R$_y$, —NR$_g$C(=O)R$_y$, —NR$_x$C(=O)NR$_x$R$_y$, —NR$_x$C(=O)OR$_y$, —NR$_x$SO$_2$R$_y$, —OC(=O)NR$_x$R$_y$, —OR$_x$, —SR$_y$, —SOR$_x$, —SO$_2$R$_x$, —OSO$_2$R$_x$, —O$_2$OR$_x$, =NSO$_2$R$_x$, —OP(=O)(OH)$_2$, —OP(=O)(OR$_x$)$_2$ and —SO$_2$NR$_x$R$_y$. "Substituted" also means any of the above groups in which one or more hydrogen atoms are replaced with —C(=O)R$_x$, —C(=O)OR$_x$, —C(=O)NR$_x$R$_y$, —CH$_2$SO$_2$R$_x$ or —CH$_2$SO$_2$NR$_x$R$_y$. In the foregoing, R$_x$ and R$_y$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The compounds of the invention, or their pharmaceutically acceptable salts may contain one or more stereocenters and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. Embodiments of the present invention contemplate various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. Embodiments of the present invention include tautomers of any said compounds.

I. Compounds

As noted above, embodiments of the present disclosure are directed to prodrugs of alvocidib. Expected advantages of the present compounds include increased bioavailability, increased solubility in typical pharmaceutical formulations, in water and in bodily fluids, decreased toxicity relative to the alvocidib parent compound when administered orally and/or improved pharmacokinetics.

Accordingly, in one embodiment, a compound having the following structure (I):

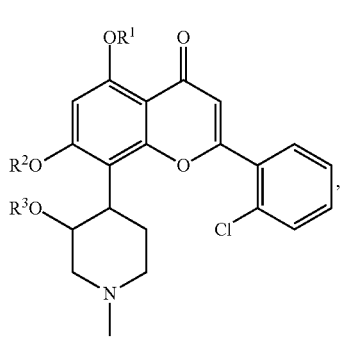

(I)

or a stereoisomer, tautomer or pharmaceutically acceptable salt thereof, wherein:

$R^1$, $R^2$ and $R^3$ are independently hydrogen, —C(=O)$R^a$, —C(=O)O$R^b$, —C(=O)NR$^c$R$^d$, —P(=O)(OR$^e$)(NR$^f$R$^g$), —P(=O)(OR$^h$)(OR$^i$), -(L$^1$)OP(=O)(OR$^h$)(OR$^i$), -(L$^1$)$_x$CH[P(=O)(OR$^h$)(OR$^i$)]$_2$, -(L$^1$)$_x$CH[P(=O)(OR$^j$)(NR$^k$R$^l$)]$_2$, —P(=O)(NR$^m$R$^n$)(NR$^o$R$^p$) or —P(=O)R$^q$R$^r$, provided at least one of $R^1$, $R^2$ and $R^3$ is not hydrogen;

$R^a$, $R^b$, $R^e$ and $R^j$ are, at each occurrence, independently hydrogen, optionally substituted $C_1$-$C_{12}$ alkyl or optionally substituted aryl, provided that $R^a$ is optionally substituted $C_2$-$C_{12}$ alkyl, substituted $C_1$-$C_{12}$ alkyl or optionally substituted aryl when both of $R^1$ and $R^2$ are hydrogen;

$R^c$ and $R^d$ are, at each occurrence, independently hydrogen, optionally substituted $C_1$-$C_{12}$ alkyl or optionally substituted aryl; or $R^c$ and $R^d$ are taken together to form an optionally substituted 3- to 12-membered heterocyclic ring;

$R^f$ and $R^g$ are, at each occurrence, independently hydrogen, optionally substituted $C_1$-$C_{12}$ alkyl or optionally substituted aryl; or $R^f$ and $R^g$ are taken together to form an optionally substituted 3- to 12-membered heterocyclic ring;

$R^h$ and $R^i$ are, at each occurrence, independently hydrogen, optionally substituted $C_1$-$C_{12}$ alkyl or optionally substituted aryl; or $R^h$ and $R^i$ are taken together to form an optionally substituted 3- to 12-membered heterocyclic ring;

$R^k$ and $R^l$ are, at each occurrence, independently hydrogen, optionally substituted $C_1$-$C_{12}$ alkyl or optionally substituted aryl; or $R^k$ and $R^l$ are taken together to form an optionally substituted 3- to 12-membered heterocyclic ring;

$R^m$ and $R^n$ are, at each occurrence, independently hydrogen, optionally substituted $C_1$-$C_{12}$ alkyl or optionally substituted aryl; or $R^m$ and $R^n$ are taken together to form an optionally substituted 3- to 12-membered heterocyclic ring;

$R^o$ and $R^p$ are, at each occurrence, independently hydrogen, optionally substituted $C_1$-$C_{12}$ alkyl or optionally substituted aryl; or $R^o$ and $R^p$ are taken together to form an optionally substituted 3- to 12-membered heterocyclic ring;

$R^q$ and $R^r$ are, at each occurrence, independently hydrogen, optionally substituted $C_1$-$C_{12}$ alkyl or optionally substituted aryl; or $R^q$ and $R^r$ are taken together to form an optionally substituted 3- to 12-membered heterocyclic ring;

$L^1$ is, at each occurrence, independently $C_1$-$C_6$ alkylene;

x is, at each occurrence, independently 0 or 1, provided that the compound is not a compound selected from Table 1.

In another embodiment of the compound of structure (I):

$R^1$, $R^2$ and $R^3$ are independently hydrogen, —C(=O)$R^a$, —C(=O)O$R^b$, —C(=O)NR$^c$R$^d$, —P(=O)(OR$^e$)NR$^f$R$^g$, —P(=O)(OR$^h$)$_2$, -(L$^1$)$_x$CH[P(=O)(OR$^i$)$_2$]$_2$ or -(L$^1$)$_x$CH[P(=O)(OR$^j$)NR$^k$R]$_2$, provided at least one of $R^1$, $R^2$ and $R^3$ is not hydrogen;

$R^a$, $R^b$, $R^c$, $R^d$, $R^e$, $R^f$, $R^g$, $R^h$, $R^i$, $R^j$, $R^k$ and $R^l$ are, at each occurrence, independently hydrogen, optionally substituted $C_1$-$C_{12}$ alkyl or optionally substituted aryl, provided that $R^a$ is optionally substituted $C_2$-$C_{12}$ alkyl or optionally substituted aryl when both of $R^1$ and $R^2$ are hydrogen;

$L^1$ is, at each occurrence, independently $C_1$-$C_6$ alkylene;

x is, at each occurrence, independently 0 or 1.

In some of the embodiments of the foregoing, each $C_1$-$C_{12}$ alkyl and aryl is independently optionally substituted with amino, halo, hydroxyl, $C_1$-$C_6$ alkoxy, $C_1$-$C_6$ alkylaminyl, $C_1$-$C_6$ alkoxycarbonyl or polyalkyleneoxide, or combinations thereof.

In certain embodiments, the compound has the following structure (I'):

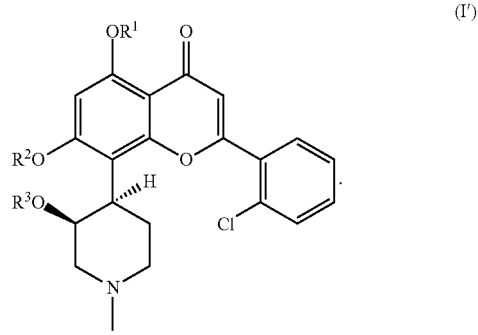

(I')

In some of the foregoing embodiments, $R^1$ is H. In other embodiments, $R^2$ is H. In different embodiment, $R^3$ is H. In more specific embodiments, $R^1$ and $R^2$ are both H, and in different embodiments $R^1$ and $R^3$ are both H. In another embodiment, $R^2$ and $R^3$ are both H.

In one specific embodiment, $R^1$—C(=O)$R^a$, —C(=O)O$R^b$, —C(=O)NR$^c$R$^d$, —P(=O)(OR$^e$)(NR$^f$R$^g$), —P(=O)(OR$^h$)(OR$^i$), -(L$^1$)OP(=O)(OR$^h$)(OR$^i$), -(L$^1$)$_x$CH[P(=O)(OR$^h$)(OR$^i$)]$_2$ or —P(=O)(NR$^m$R$^n$)(NR$^o$R$^p$). In certain other embodiments, $R^1$ is —C(=O)$R^a$, —C(=O)O$R^b$, —C(=O)NR$^c$R$^d$, —P(=O)(OR$^e$)NR$^f$R$^g$, —P(=O)(OR$^h$)$_2$ or -(L$^1$)$_x$CH[P(=O)(OR$^i$)$_2$]$_2$.

In some embodiments, $R^1$ is —C(=O)$R^a$. In more specific embodiments, $R^a$ is optionally substituted $C_1$-$C_{12}$ alkyl. In other embodiments, $R^1$ is —C(=O)O$R^b$. In some embodiments, $R^b$ is optionally substituted $C_1$-$C_{12}$ alkyl.

In one embodiment, $R^2$ is —C(=O)$R^a$, —C(=O)O$R^b$, —C(=O)NR$^c$R$^d$, —P(=O)(OR$^e$)(NR$^f$R$^g$), —P(=O)(OR$^h$)(OR$^i$), -(L$^1$)OP(=O)(OR$^h$)(OR$^i$), -(L$^1$)$_x$CH[P(=O)(OR$^h$)(OR$^i$)]$_2$ or —P(=O)(NR$^m$R$^n$)(NR$^o$R$^p$). In some different embodiments, $R^2$ is —C(=O)$R^a$, —C(=O)$R^b$, —C(=O)N$R^cR^d$, —P(=O)(O$R^e$)N$R^fR^g$, —P(=O)(O$R^h$)$_2$ or -(L$^1$)$_x$CH[P(=O)(O$R^i$)$_2$]$_2$.

In certain specific embodiments, $R^2$ is —C(=O)$R^a$. In some of these embodiments, $R^a$ is optionally substituted $C_1$-$C_{12}$ alkyl. In certain other embodiments, $R^a$ is optionally substituted $C_1$-$C_{12}$ alkyl or optionally substituted aryl. In more specific embodiments, each $C_1$-$C_{12}$ alkyl and aryl is independently substituted with amino, halo, hydroxyl, $C_1$-$C_6$ alkoxy or polyalkyleneoxide, or combinations thereof.

In other embodiments, $R^2$ is —C(=O)$R^b$. In some of these embodiments, $R^b$ is optionally substituted $C_1$-$C_{12}$ alkyl.

In some embodiments, $R^2$ is —C(=O)N$R^cR^d$. In more specific embodiments, $R^c$ is hydrogen and $R^d$ is optionally substituted $C_1$-$C_{12}$ alkyl.

In other embodiments, $R^2$ is —P(=O)(O$R^e$)N$R^fR^g$. In some embodiments, $R^2$ is —P(=O)(O$R^e$)(N$R^fR^g$). In some of those embodiments, $R^f$ is hydrogen and $R^e$ and $R^g$ are optionally substituted $C_1$-$C_{12}$ alkyl. In more specific embodiments, $R^g$ is substituted with $C_1$-$C_6$ alkyloxycarbonyl.

In some embodiments, $R^2$ is —P(=O)(O$R^h$)$_2$. In certain more specific embodiments, $R^h$ is, at each occurrence, independently H or $C_1$-$C_6$ alkyl. In certain embodiments, $R^2$ is -(L$^1$)OP(=O)(O$R^h$)(O$R^i$). In some embodiments, $R^h$ and $R^i$ are, independently H or optionally substituted $C_1$-$C_6$ alkyl.

In certain embodiments, $R^2$ is -(L$^1$)$_x$CH[P(=O)(O$R^i$)$_2$]$_2$. In some specific embodiments, $R^i$ is, at each occurrence, independently H or $C_1$-$C_6$ alkyl, $L^1$ is —CH$_2$— and x is 1. In certain embodiments, $R^2$ is -(L$^1$)$_x$CH[P(=O)(O$R^h$)(O$R^i$)]$_2$. In more specific embodiments, $R^h$ and $R^i$ are independently H or optionally substituted $C_1$-$C_6$ alkyl, $L^1$ is —CH$_2$— and x is 1.

In one embodiment, $R^2$ is —P(=O)(N$R^mR^n$)(N$R^oR^p$). In certain more specific embodiments, $R^m$, $R^n$, $R^o$ and $R^p$ are independently optionally substituted $C_1$-$C_{12}$ alkyl.

In some embodiments, $R^2$ is —P(=O)(O$R^h$)(O$R^i$). In some embodiments, $R^h$ and $R^i$ are independently optionally substituted $C_1$-$C_{12}$ alkyl. In other embodiments, $R^h$ and $R^i$ are taken together to form an optionally substituted 3- to 12-membered heterocyclic ring.

In other embodiments, $R^3$ is —C(=O)$R^a$, —C(=O)$R^b$, —C(=O)N$R^cR^d$, —P(=O)(O$R^e$)N$R^fR^g$, —P(=O)(O$R^h$)$_2$ or -(L$^1$)$_x$CH[P(=O)(O$R^i$)$_2$]$_2$. In another different embodiment, $R^3$—C(=O)$R^a$, —C(=O)$R^b$, —C(=O)N$R^cR^d$, —P(=O)(O$R^e$)(N$R^fR^g$), —P(=O)(O$R^h$)(O$R^i$), -(L$^1$)OP(=O)(O$R^h$)(O$R^i$), -(L$^1$)$_x$CH[P(=O)(O$R^h$)(O$R^i$)]$_2$ or —P(=O)(N$R^mR^n$)(N$R^oR^p$).

In some specific embodiments, $R^3$ is —C(=O)$R^a$. In some of these embodiment specific embodiments, $R^a$ is optionally substituted $C_1$-$C_{12}$ alkyl, provided that $R^a$ is optionally substituted $C_2$-$C_{12}$ alkyl when $R^1$ and $R^2$ are both H.

In certain embodiments, $R^3$ is —C(=O)$R^b$. In some of these embodiments, $R^b$ is optionally substituted $C_1$-$C_{12}$ alkyl. In more specific embodiments, the optionally substituted $C_1$-$C_{12}$ alkyl and optionally substituted aryl are independently substituted with amino, halo, hydroxyl, $C_1$-$C_6$ alkoxy, $C_1$-$C_6$ alkylaminyl, $C_1$-$C_6$ alkoxycarbonyl or polyalkyleneoxide, or combinations thereof.

In some embodiments, $R^3$ is —C(=O)N$R^cR^d$. In some of these embodiments, $R^c$ is hydrogen and $R^d$ is optionally substituted $C_1$-$C_{12}$ alkyl.

In some embodiments, $R^3$ is —P(=O)(O$R^e$)N$R^fR^g$. In some embodiments, $R^3$ is —P(=O)(O$R^e$)(N$R^fR^g$). In specific embodiments, $R^f$ is hydrogen and $R^e$ and $R^g$ are optionally substituted $C_1$-$C_{12}$ alkyl. In certain more specific embodiments, $R^g$ is substituted with $C_1$-$C_6$ alkyloxycarbonyl.

In some embodiments, $R^3$ is —P(=O)(O$R^h$)$_2$. In certain embodiments, $R^3$ is —P(=O)(O$R^h$)(O$R^i$). In some more specific embodiments, $R^h$ is, at each occurrence, independently H or $C_1$-$C_6$ alkyl. In other specific embodiments, $R^h$ and $R^i$ are independently H or optionally substituted $C_1$-$C_6$ alkyl. In some other embodiments, $R^h$ and $R^i$ join to form an optionally substituted 3- to 12-membered heterocyclic ring.

In certain embodiments, $R^3$ is -(L$^1$)$_x$CH[P(=O)(O$R^i$)$_2$]$_2$. In some of these embodiments, $R^i$ is, at each occurrence, independently H or $C_1$-$C_6$ alkyl, $L^1$ is —CH$_2$— and x is 1. In certain embodiments, $R^3$ is -(L$^1$)$_x$CH[P(=O)(O$R^h$)(O$R^i$)]$_2$. In more specific embodiments, $R^h$ and $R^i$ are independently H or optionally substituted $C_1$-$C_6$ alkyl, $L^1$ is —CH$_2$— and x is 1.

In some embodiments, $R^3$ is —P(=O)(N$R^mR^n$)(N$R^oR^p$). In certain more specific embodiments, $R^m$, $R^n$, $R^o$ and $R^p$ are independently optionally substituted $C_1$-$C_{12}$ alkyl.

In some embodiments, $R^1$, $R^2$ and $R^3$ are independently selected from H and one of the following structures:

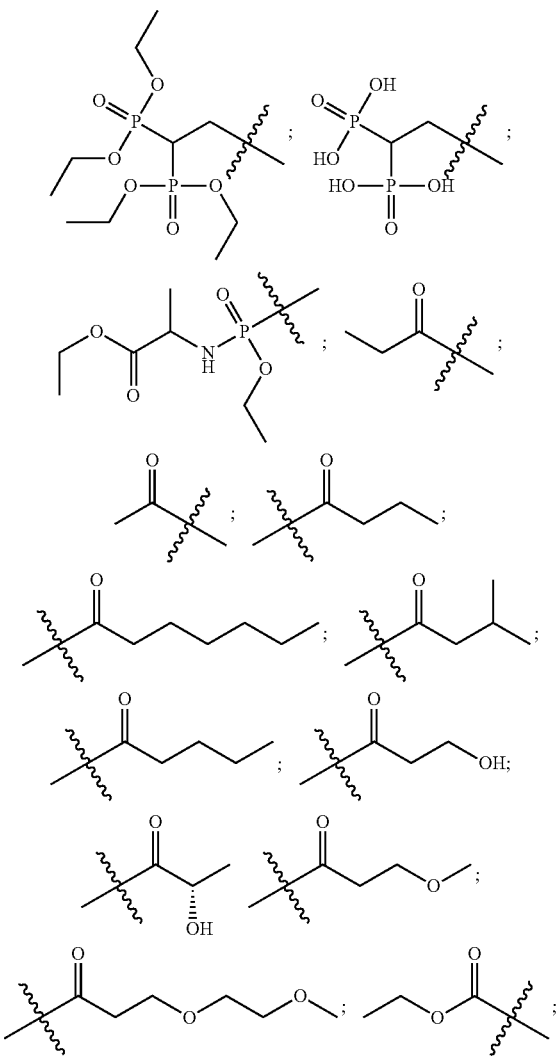

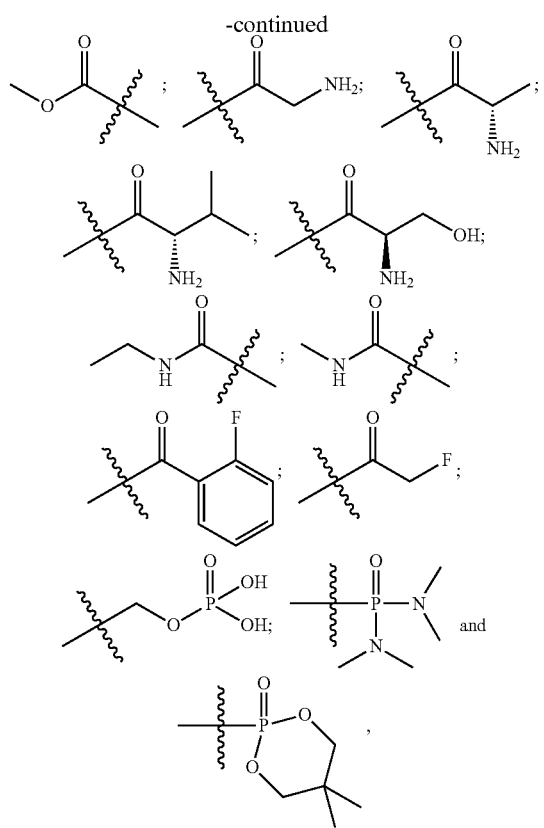

provided that at least one of $R^1$, $R^2$ and $R^3$ is not H, and $R^3$ is not —C(=O)CH$_3$ when both of $R^1$ and $R^2$ are H.

In some specific embodiments, $R^1$, $R^2$ and $R^3$ are independently selected from H and one of the following structures:

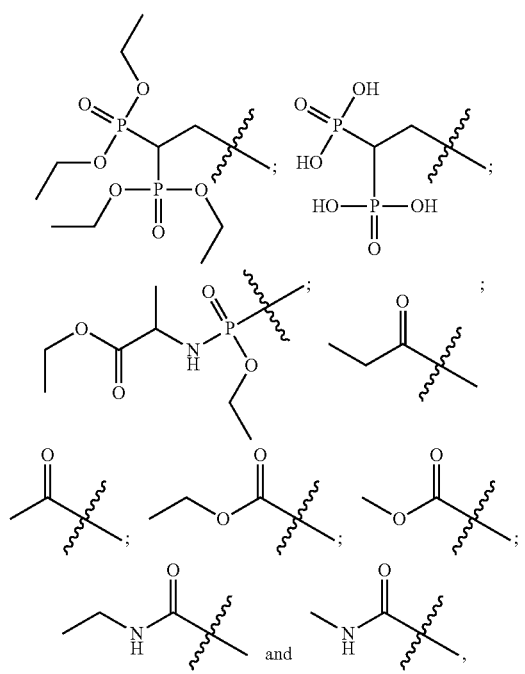

provided that at least one of $R^1$, $R^2$ and $R^3$ is not H, and $R^3$ is not —C(=O)CH$_3$, when both of $R^1$ and $R^3$ are H.

In certain embodiments, $R^1$ has one of the following structures:

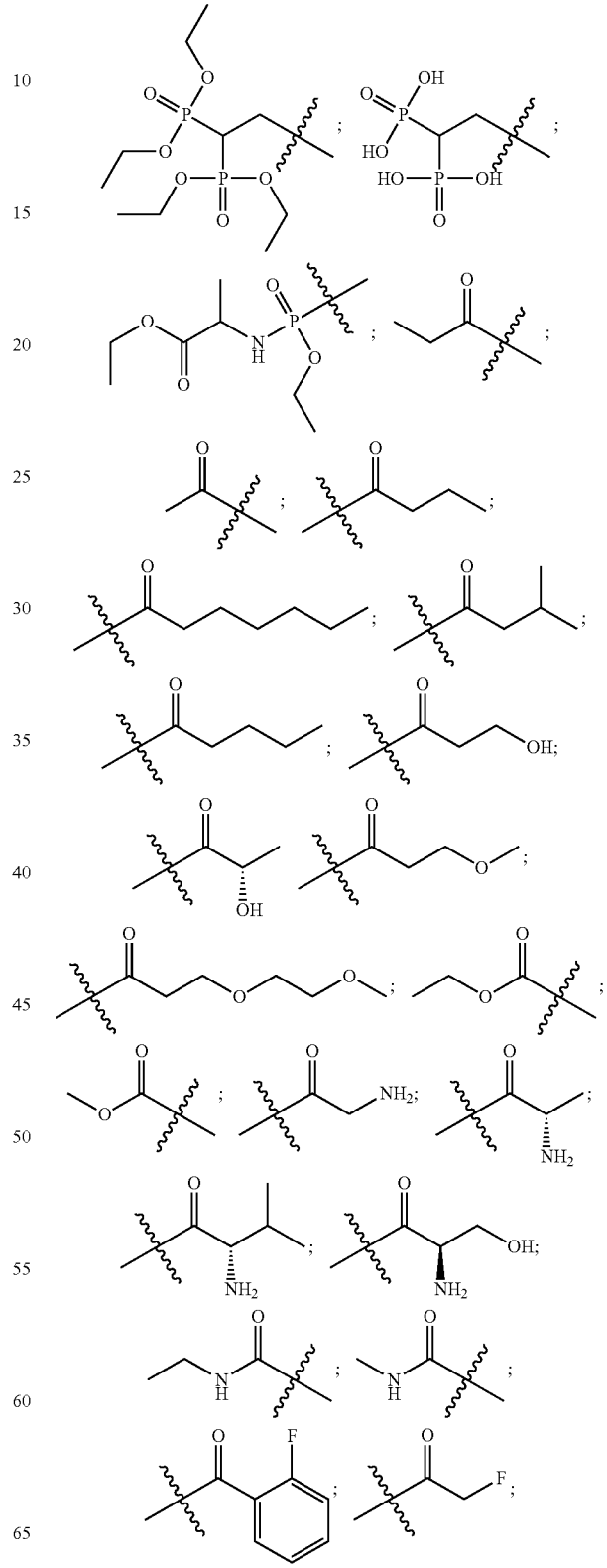

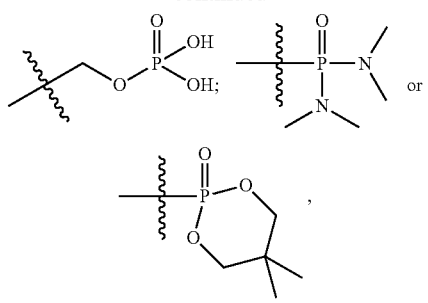
and R² and R³ are both H.
In certain embodiments, R² has one of the following structures:
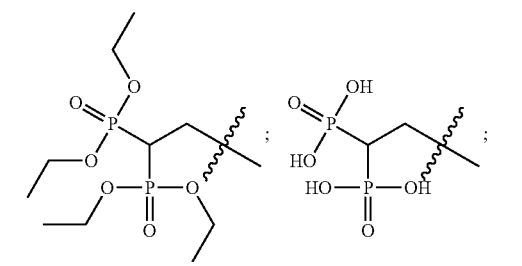
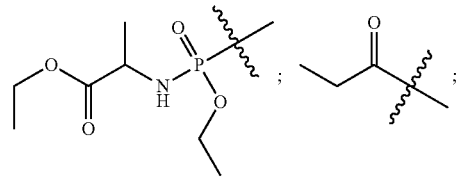
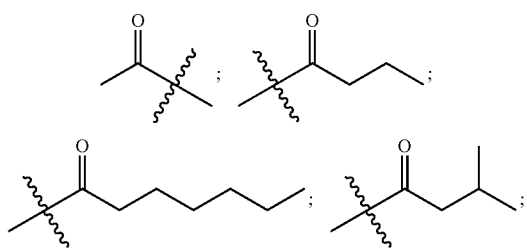
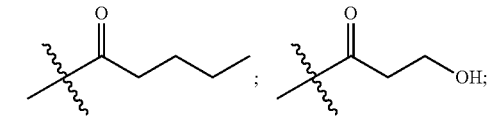
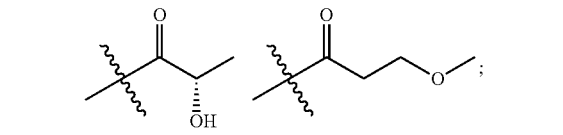
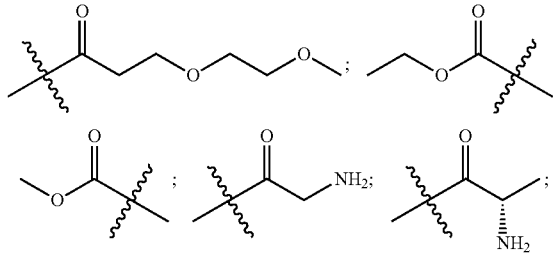
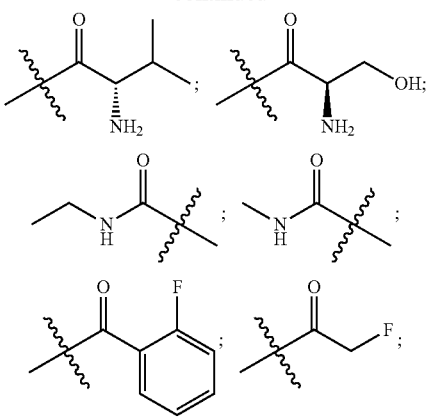
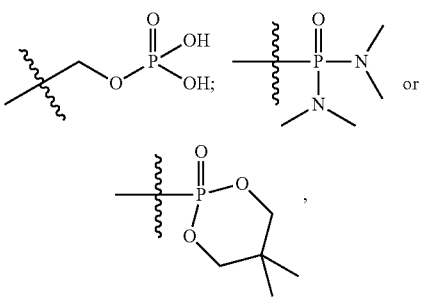
and R¹ and R³ are both H.
In some embodiments, R² has one of the following structures:
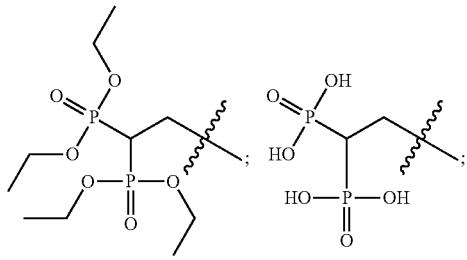
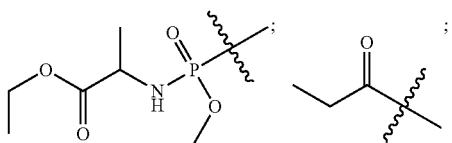
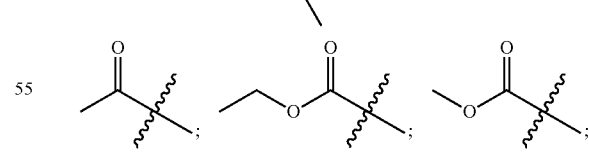
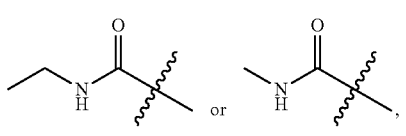
and R¹ and R³ are both H.
In some embodiments, R³ has one of the following structures:

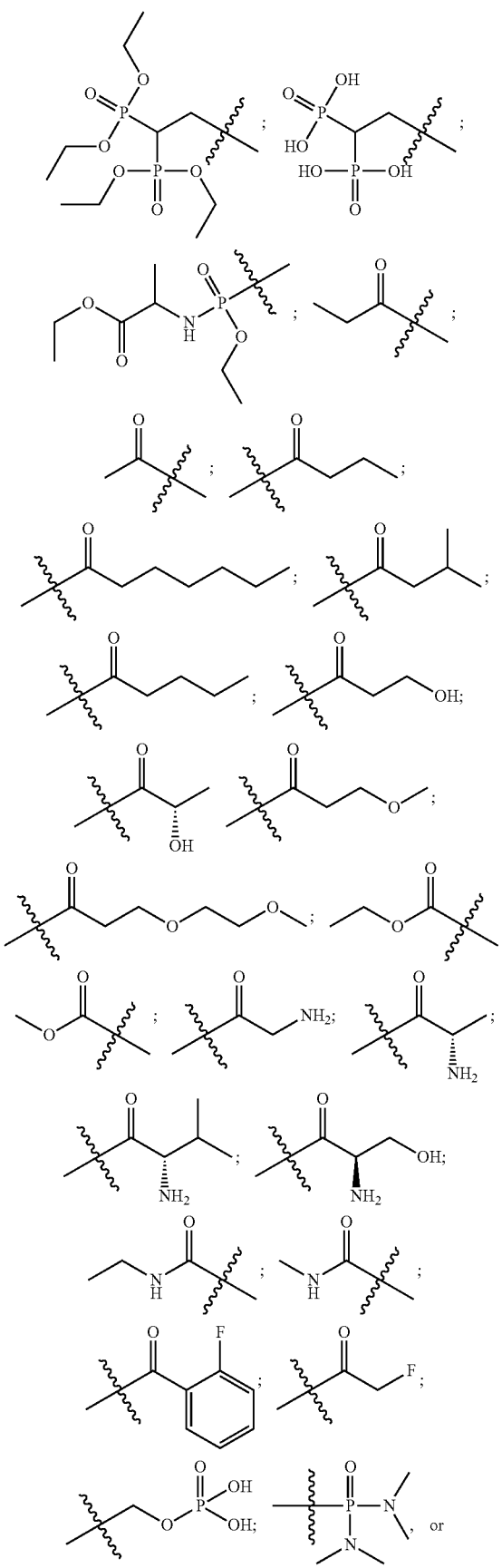
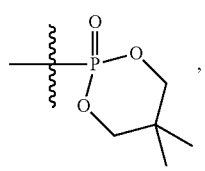 [SMILES: *P1(=O)OCC(C)(C)CO1]
and $R^1$ and $R^2$ are both H.
In certain embodiments, $R^3$ has one of the following structures:
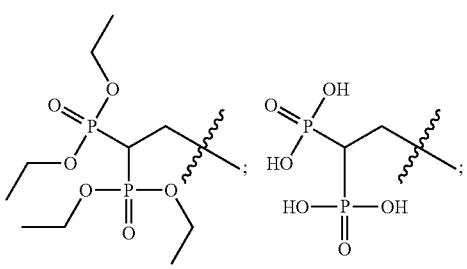
and $R^1$ and $R^2$ are both H.
In some of the foregoing embodiments, the compound has one of the following structures:
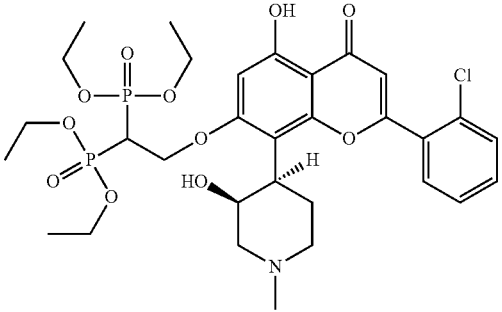

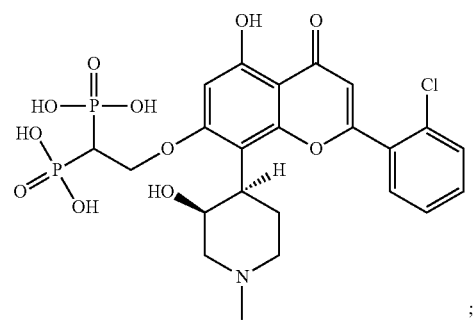
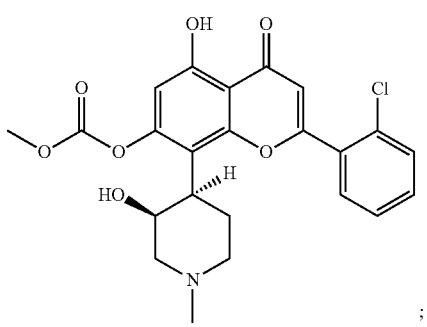
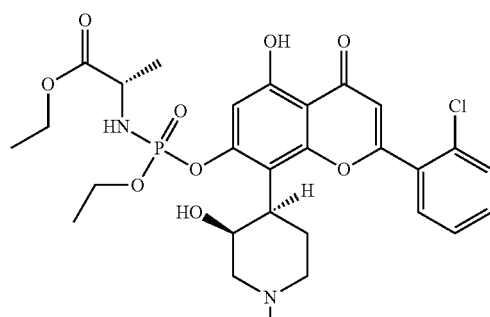
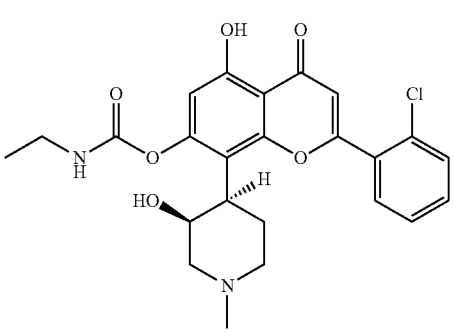
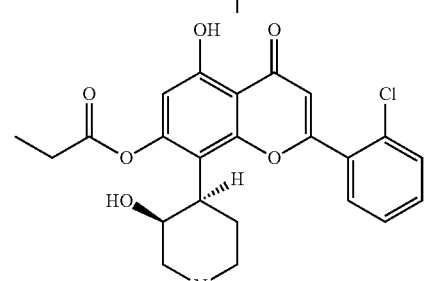
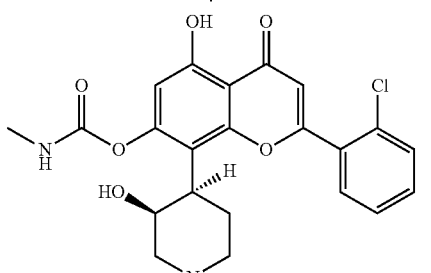
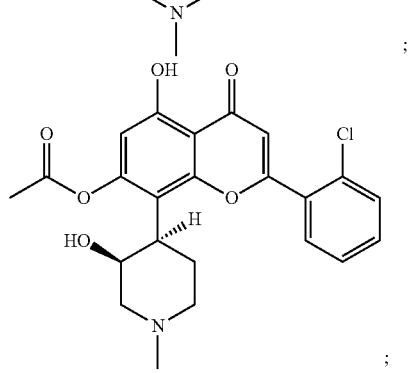
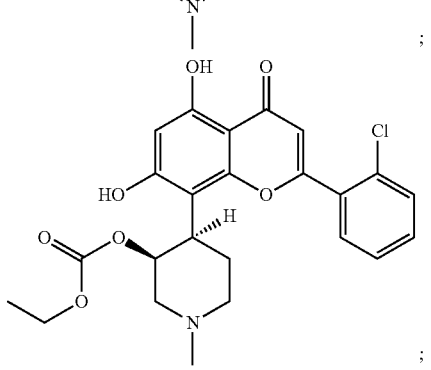

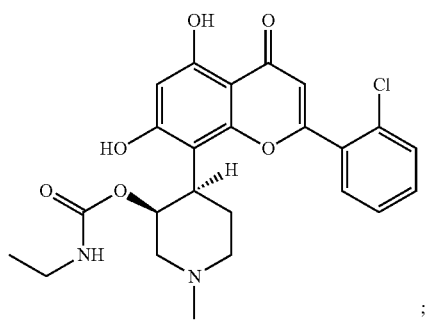
;
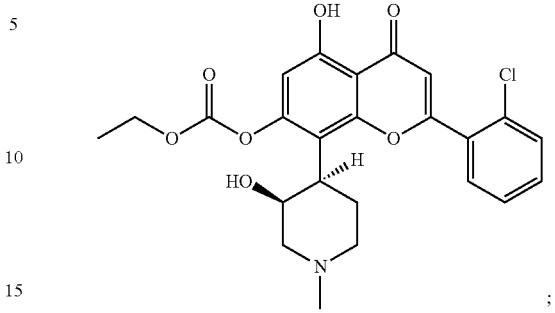
;
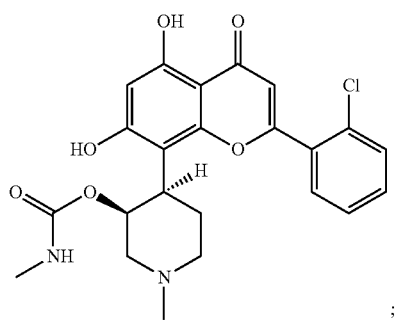
;
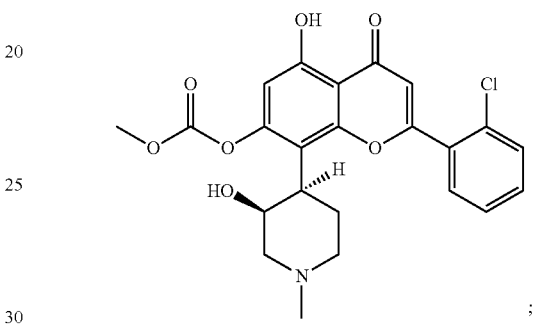
;
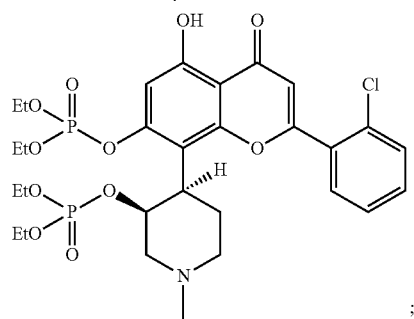
;
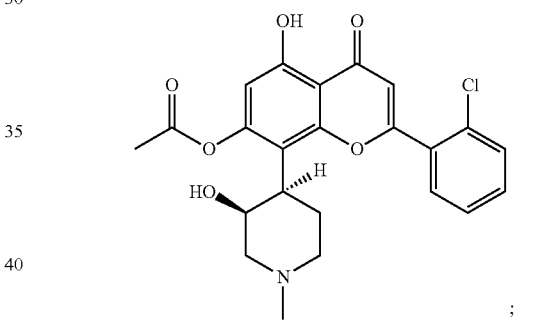
;
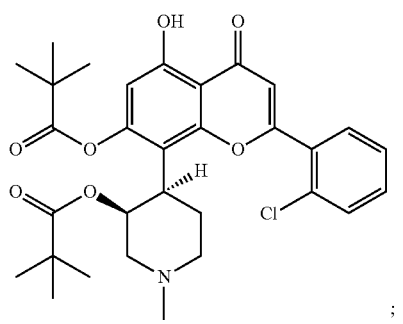
;
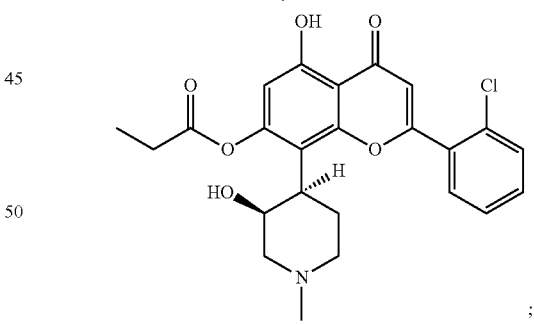
;
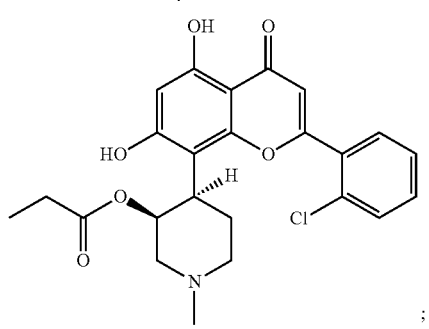
;
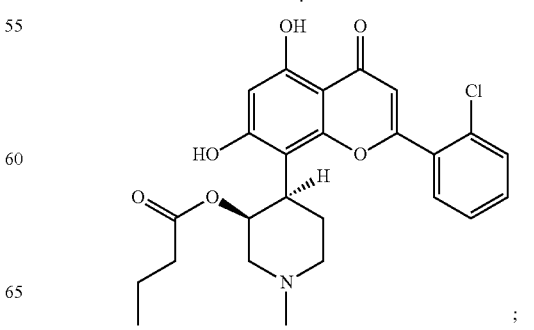
;

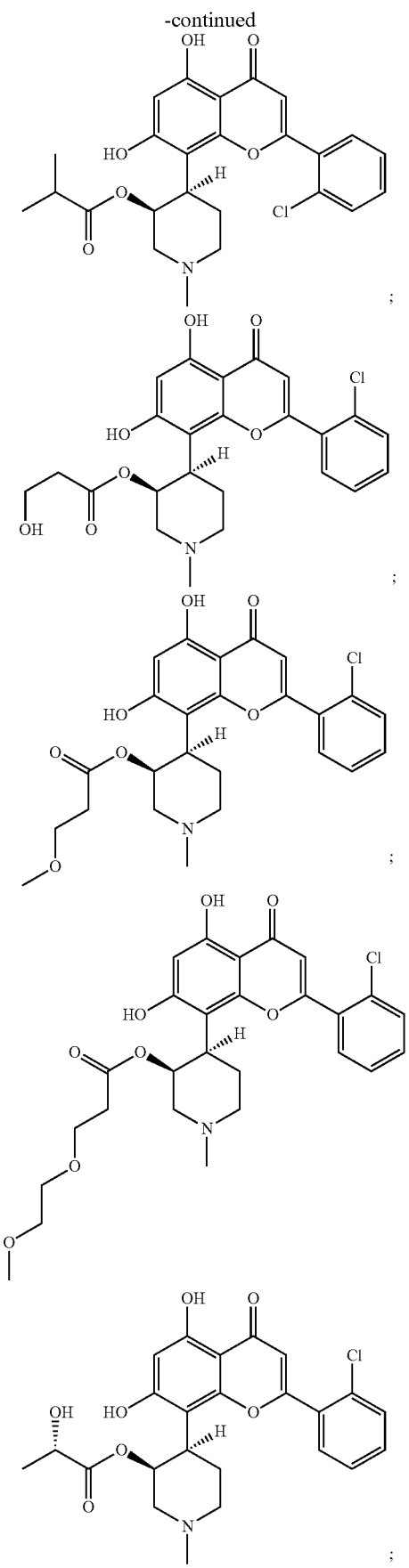
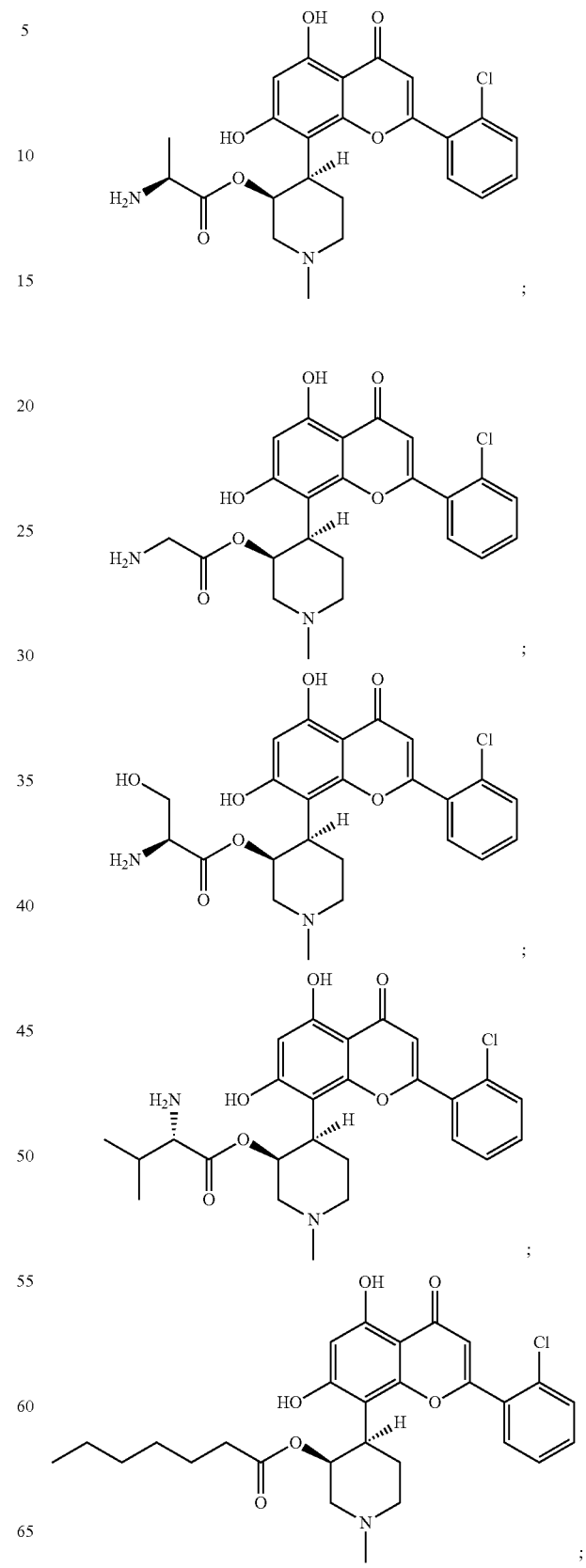

-continued
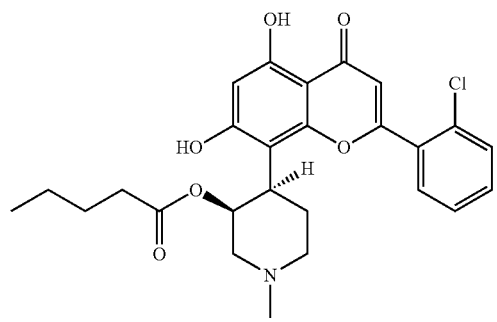
;
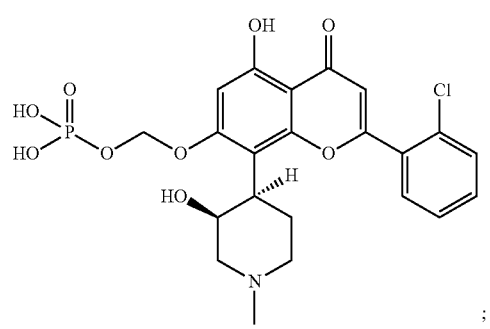
;
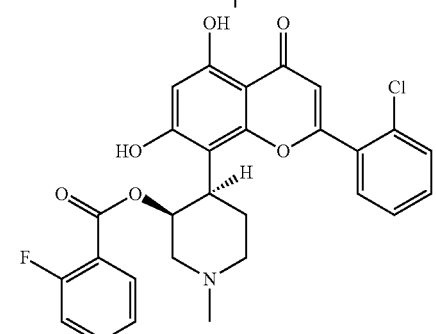
;
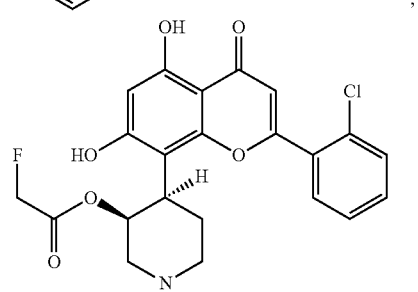
;
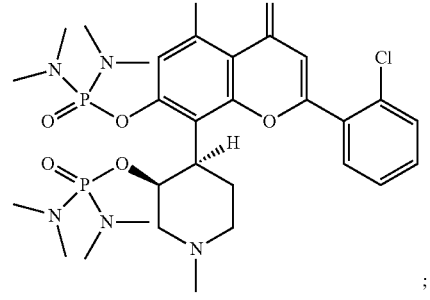
;
-continued
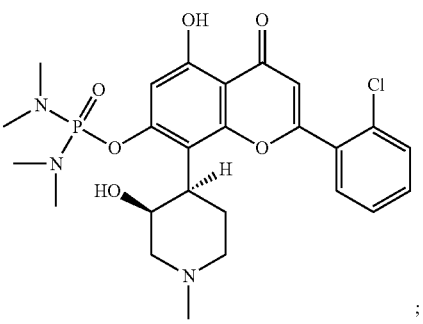
;
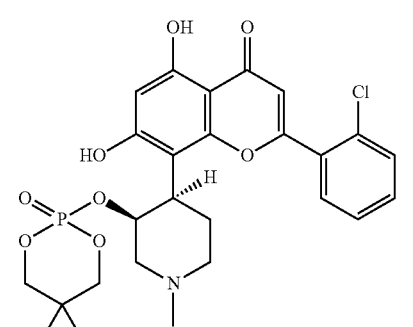
;
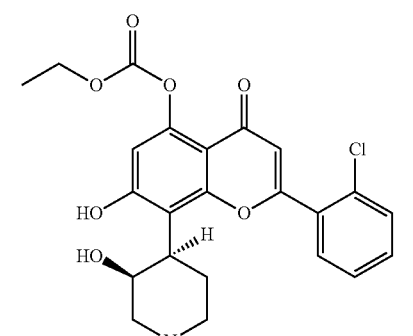
;
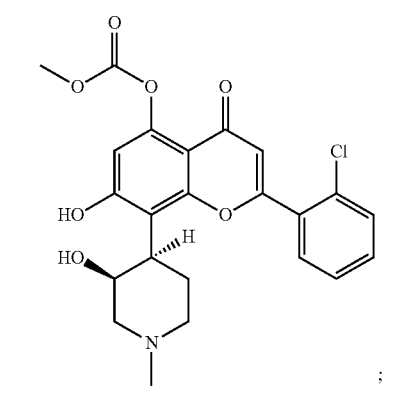
;

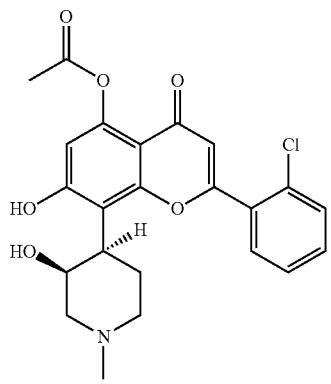
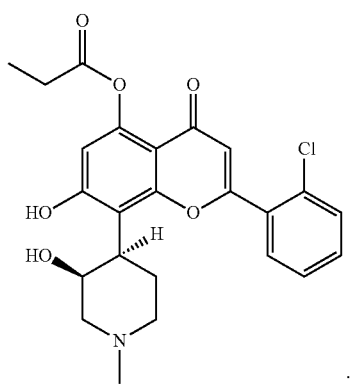
In some of the foregoing embodiments, the compound has one of the following structures:
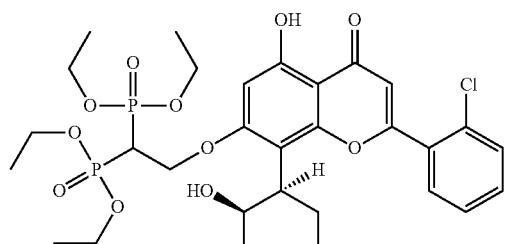
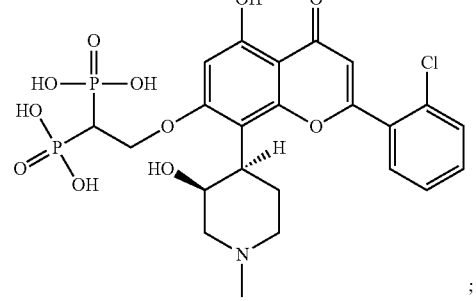
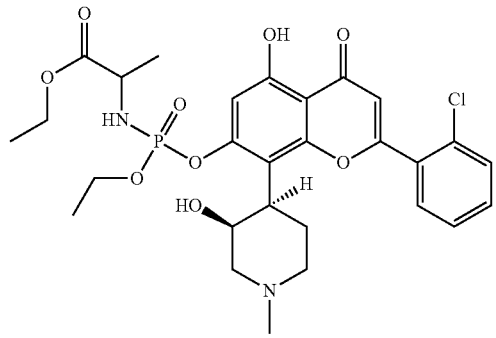
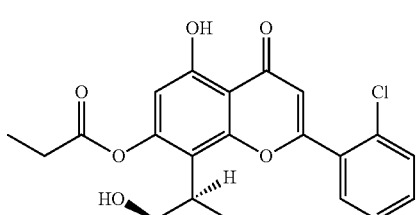
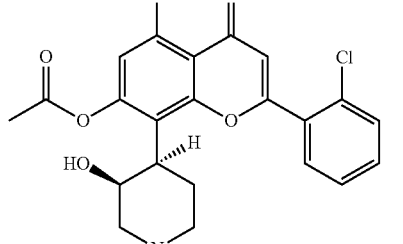
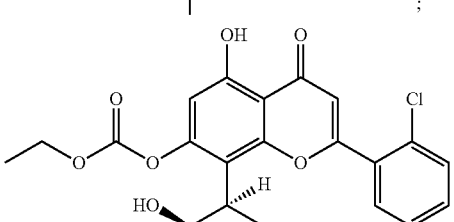
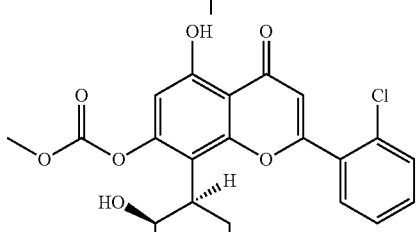

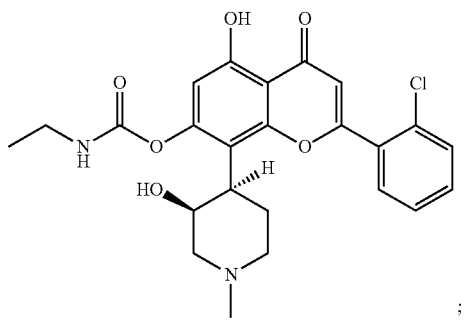
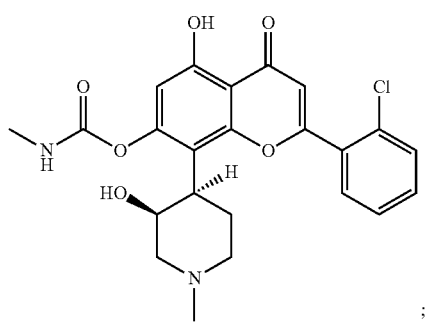
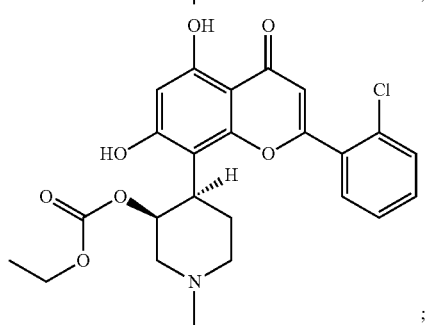
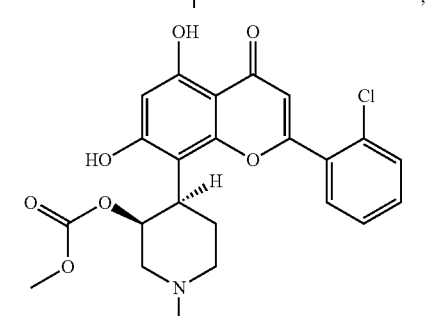
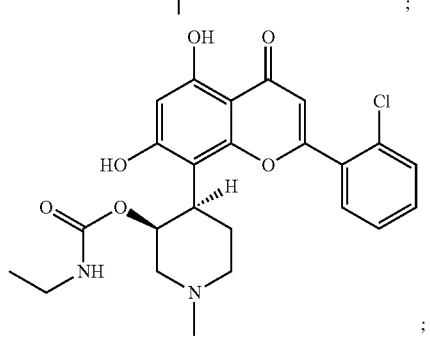
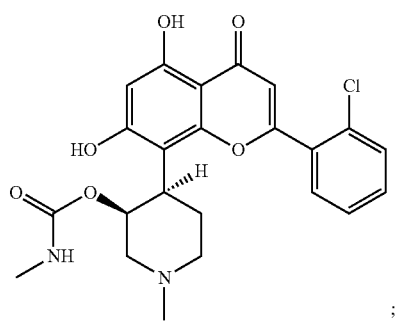
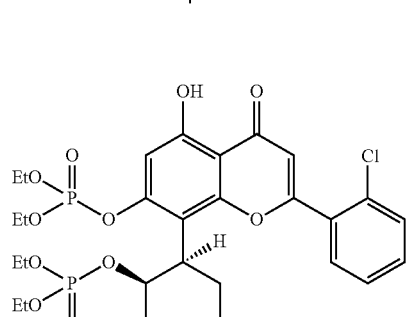
In some embodiments the compound is not a compound selected from Table 1:
TABLE 1
Excluded Compounds
Compound Structure
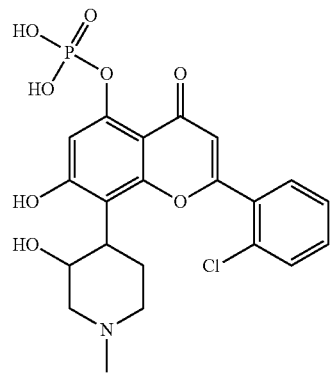 [SMILES: CN1CCC(c2c(O)cc(OP(=O)(O)O)c3c(=O)cc(-c4ccccc4Cl)oc23)C(O)C1]

TABLE 1-continued
Excluded Compounds
Compound Structure
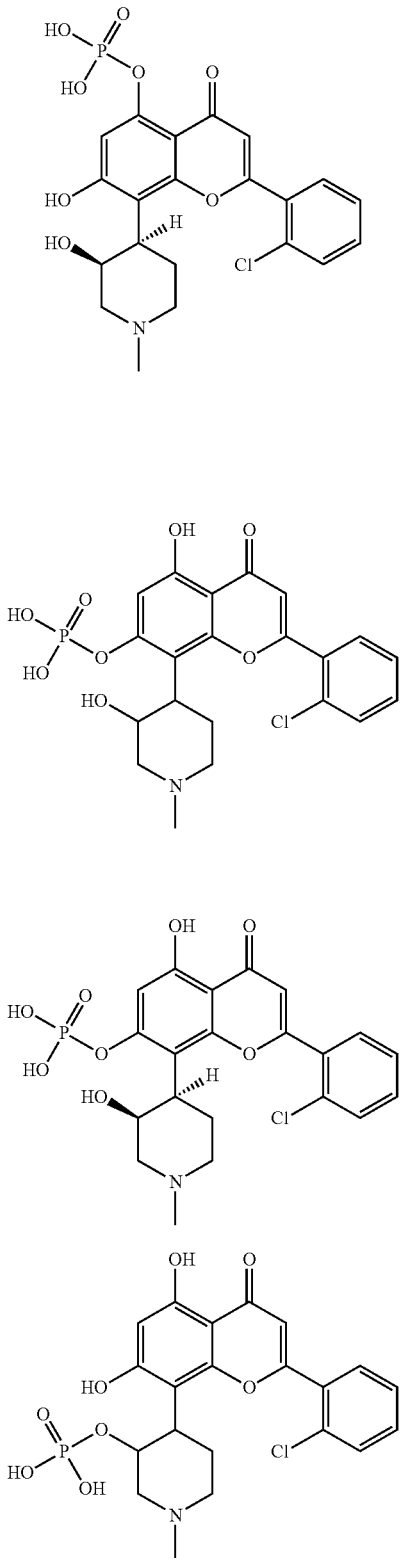

For clarity, some embodiments do not include any of the specific compounds disclosed in U.S. application Ser. No. 15/158,206, filed May 18, 2016.

In some embodiments, the compound is selected from Table 2:

TABLE 2

Example Compounds

| Compound Number | Compound Structure |
|---|---|
| 1 | 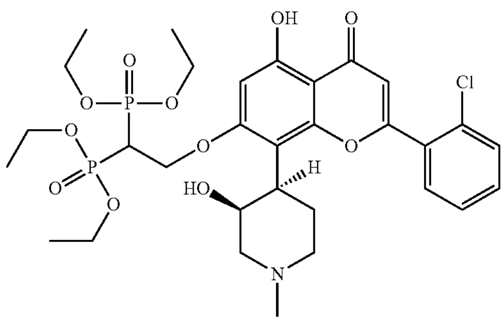 [SMILES: CCOP(=O)(OCC)C(COc1cc(O)c2c(=O)cc(-c3ccccc3Cl)oc2c1[C@H]1CCN(C)C[C@H]1O)P(=O)(OCC)OCC] |
| 2 | 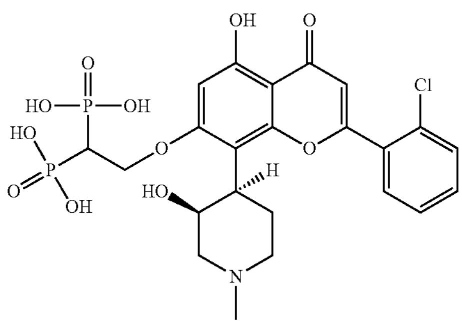 [SMILES: CN1CC[C@H](c2c(OCC(P(=O)(O)O)P(=O)(O)O)cc(O)c3c(=O)cc(-c4ccccc4Cl)oc23)[C@H](O)C1] |
| 3 | 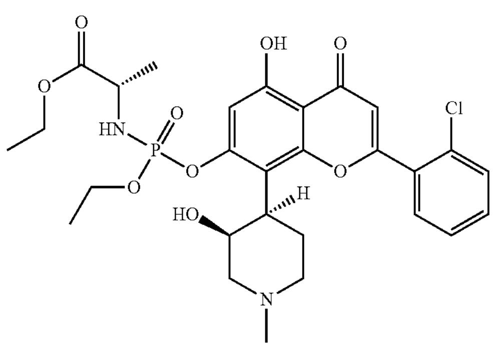 [SMILES: CCOC(=O)[C@H](C)NP(=O)(OCC)Oc1cc(O)c2c(=O)cc(-c3ccccc3Cl)oc2c1[C@H]1CCN(C)C[C@H]1O] |
| 4 | 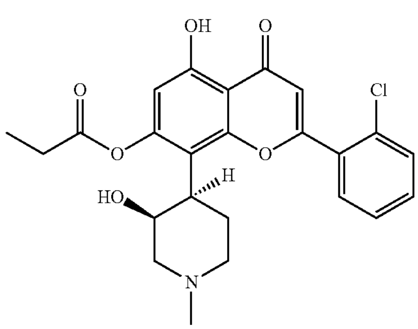 [SMILES: CCC(=O)Oc1cc(O)c2c(=O)cc(-c3ccccc3Cl)oc2c1[C@H]1CCN(C)C[C@H]1O] |

TABLE 2-continued

Example Compounds

| Compound Number | Compound Structure |
|---|---|
| 5 | 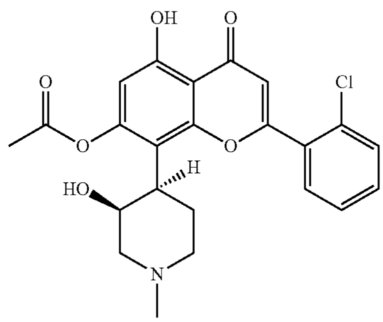 [SMILES: CC(=O)Oc1cc(O)c2c(=O)cc(-c3ccccc3Cl)oc2c1[C@H]1CCN(C)C[C@H]1O] |
| 6 | 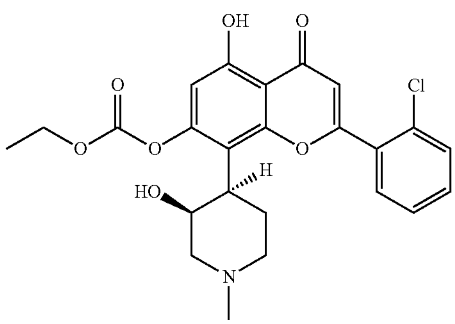 [SMILES: CCOC(=O)Oc1cc(O)c2c(=O)cc(-c3ccccc3Cl)oc2c1[C@H]1CCN(C)C[C@H]1O] |
| 7 | 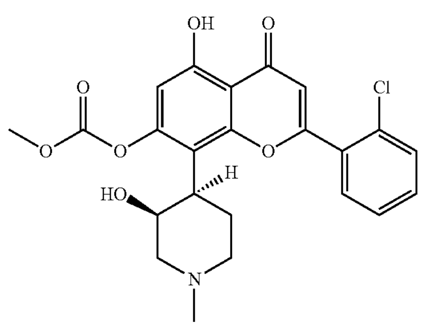 |
| 8 | 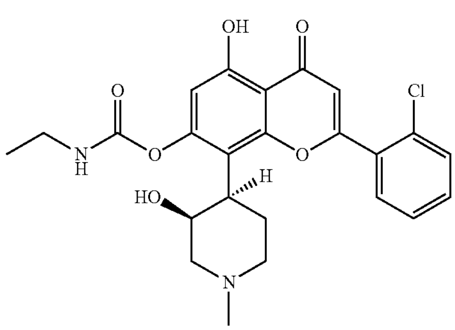 [SMILES: CCNC(=O)Oc1cc(O)c2c(=O)cc(-c3ccccc3Cl)oc2c1[C@H]1CCN(C)C[C@H]1O] |

TABLE 2-continued

Example Compounds

| Compound Number | Compound Structure |
|---|---|
| 9 | 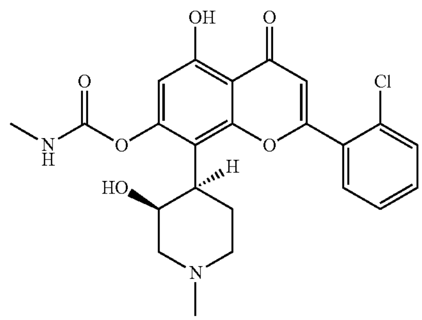 [SMILES: CNC(=O)Oc1cc(O)c2c(=O)cc(-c3ccccc3Cl)oc2c1[C@H]1CCN(C)C[C@H]1O] |
| 10 | 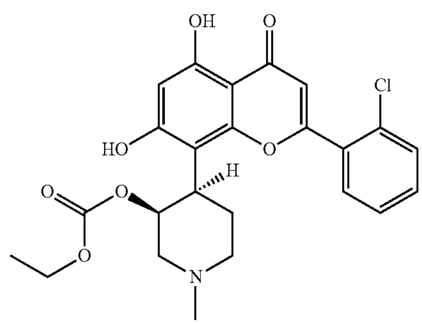 [SMILES: CCOC(=O)O[C@@H]1CN(C)CC[C@@H]1c1c(O)cc(O)c2c(=O)cc(-c3ccccc3Cl)oc12] |
| 11 | 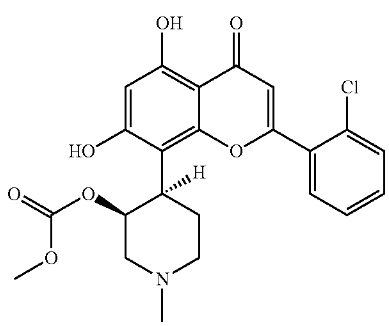 [SMILES: COC(=O)O[C@@H]1CN(C)CC[C@@H]1c1c(O)cc(O)c2c(=O)cc(-c3ccccc3Cl)oc12] |
| 12 | 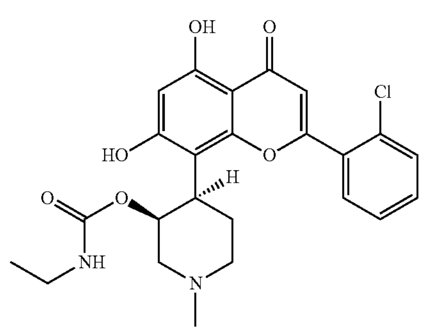 [SMILES: CCNC(=O)O[C@@H]1CN(C)CC[C@@H]1c1c(O)cc(O)c2c(=O)cc(-c3ccccc3Cl)oc12] |

TABLE 2-continued

Example Compounds

| Compound Number | Compound Structure |
|---|---|
| 13 | *(structure: 5,7-dihydroxy-2-(2-chlorophenyl)-4H-chromen-4-one with N-methylpiperidine bearing a methylcarbamate)* |
| 14 | *(structure: 5-hydroxy-2-(2-chlorophenyl)-4H-chromen-4-one with diethyl phosphate groups on the 7-position and on the N-methylpiperidine)* |
| 15 | *(structure: 5-hydroxy-2-(2-chlorophenyl)-4H-chromen-4-one with pivaloyl ester on the 7-position and on the N-methylpiperidine)* |
| 16 | *(structure: 5,7-dihydroxy-2-(2-chlorophenyl)-4H-chromen-4-one with propionate ester on the N-methylpiperidine)* |

TABLE 2-continued

Example Compounds

| Compound Number | Compound Structure |
|---|---|
| 17 | 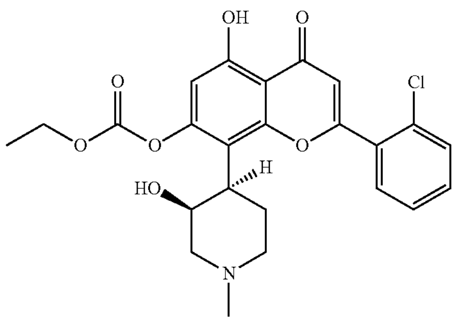 [SMILES: CCOC(=O)Oc1cc(O)c2c(=O)cc(-c3ccccc3Cl)oc2c1[C@H]1CCN(C)C[C@H]1O] |
| 18 | 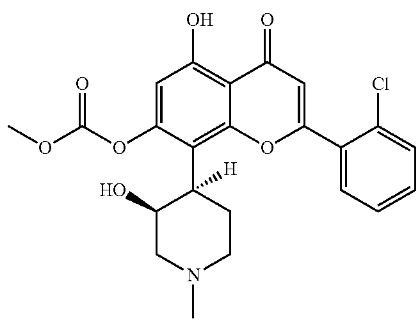 |
| 19 | 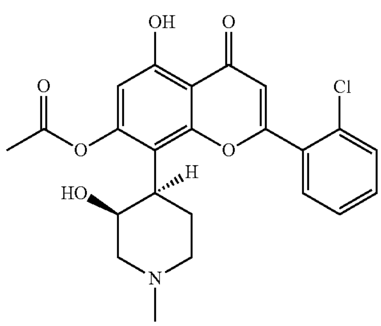 [SMILES: CC(=O)Oc1cc(O)c2c(=O)cc(-c3ccccc3Cl)oc2c1[C@H]1CCN(C)C[C@H]1O] |
| 20 | 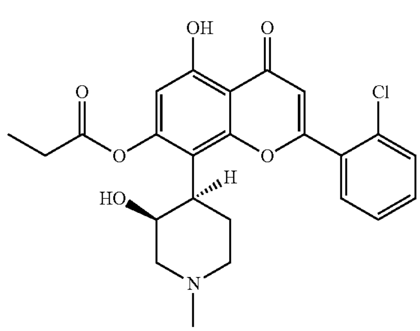 |

TABLE 2-continued

Example Compounds

| Compound Number | Compound Structure |
|---|---|
| 21 | 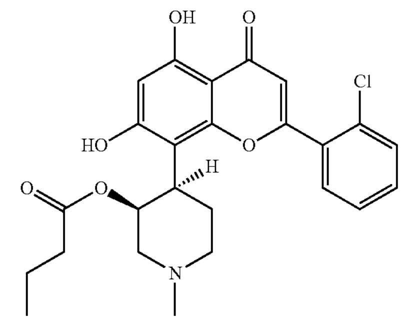 [SMILES: CCCC(=O)O[C@@H]1CN(C)CC[C@@H]1c1c(O)cc(O)c2c(=O)cc(-c3ccccc3Cl)oc12] |
| 22 | 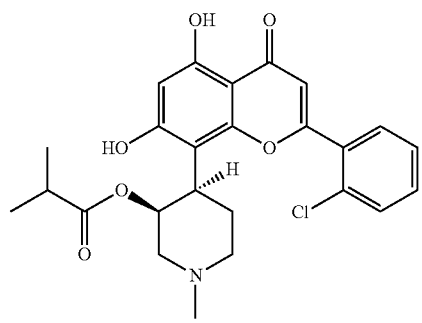 [SMILES: CC(C)C(=O)O[C@@H]1CN(C)CC[C@@H]1c1c(O)cc(O)c2c(=O)cc(-c3ccccc3Cl)oc12] |
| 23 | 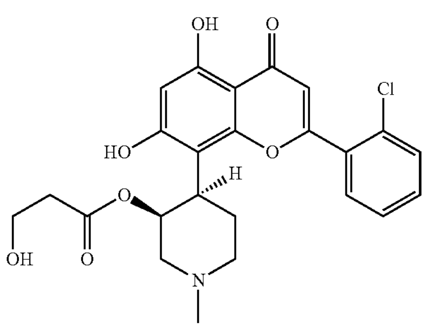 [SMILES: CN1CC[C@H](c2c(O)cc(O)c3c(=O)cc(-c4ccccc4Cl)oc23)[C@H](OC(=O)CCO)C1] |
| 24 | 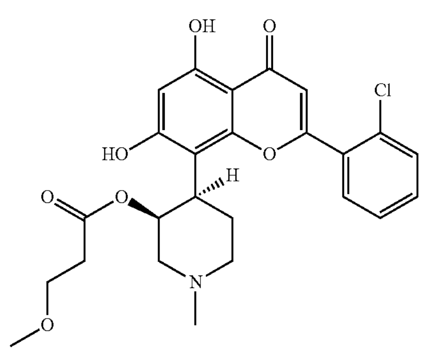 [SMILES: COCCC(=O)O[C@@H]1CN(C)CC[C@@H]1c1c(O)cc(O)c2c(=O)cc(-c3ccccc3Cl)oc12] |

TABLE 2-continued
Example Compounds
| Compound Number | Compound Structure |
|---|---|
| 25 | 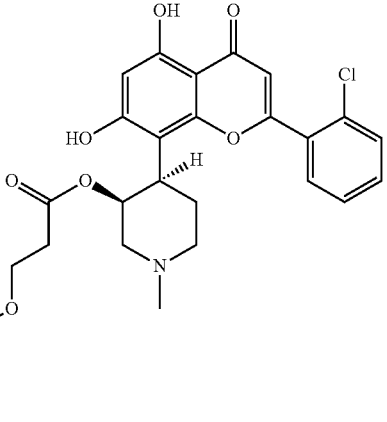 |
| 26 | 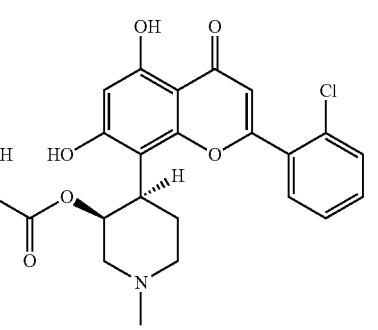 |
| 27 | 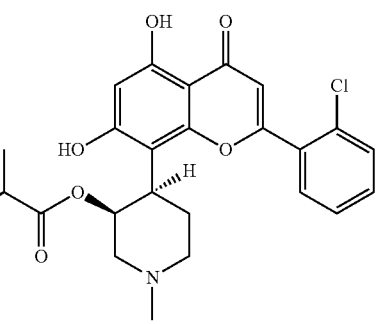 |
| 28 | 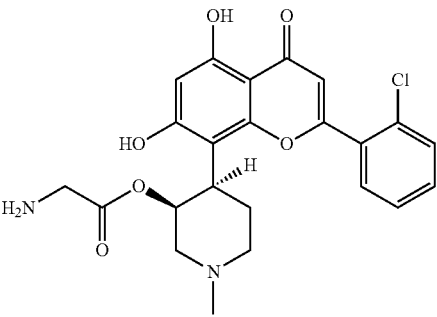 [SMILES: CN1CC[C@H](c2c(O)cc(O)c3c(=O)cc(-c4ccccc4Cl)oc23)[C@H](OC(=O)CN)C1] |

TABLE 2-continued

Example Compounds

| Compound Number | Compound Structure |
|---|---|
| 29 | 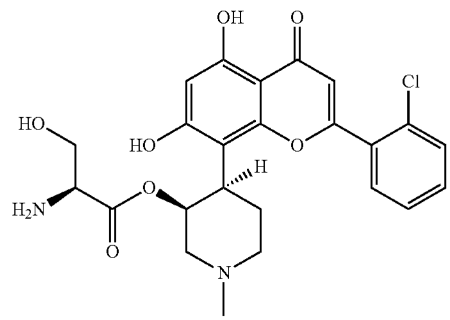 [SMILES: CN1CC[C@H](c2c(O)cc(O)c3c(=O)cc(-c4ccccc4Cl)oc23)[C@H](OC(=O)[C@@H](N)CO)C1] |
| 30 | 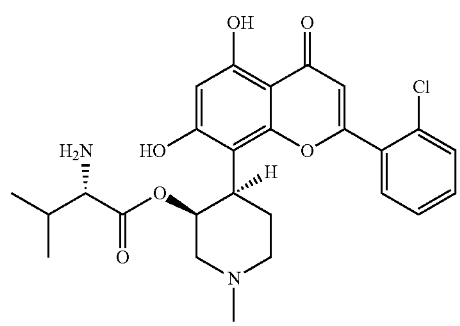 [SMILES: CC(C)[C@H](N)C(=O)O[C@@H]1CN(C)CC[C@@H]1c1c(O)cc(O)c2c(=O)cc(-c3ccccc3Cl)oc12] |
| 31 | 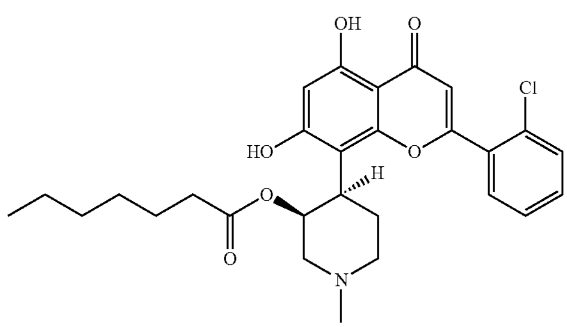 [SMILES: CCCCCCC(=O)O[C@@H]1CN(C)CC[C@@H]1c1c(O)cc(O)c2c(=O)cc(-c3ccccc3Cl)oc12] |
| 32 | 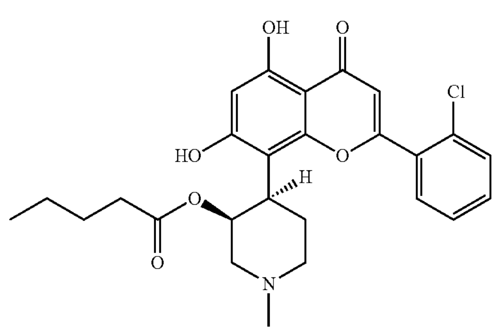 [SMILES: CCCCC(=O)O[C@@H]1CN(C)CC[C@@H]1c1c(O)cc(O)c2c(=O)cc(-c3ccccc3Cl)oc12] |

TABLE 2-continued

Example Compounds

| Compound Number | Compound Structure |
|---|---|
| 33 | 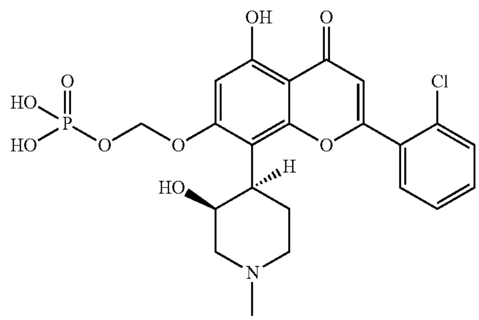 [SMILES: CN1CC[C@H](c2c(OCOP(=O)(O)O)cc(O)c3c(=O)cc(-c4ccccc4Cl)oc23)[C@H](O)C1] |
| 34 | 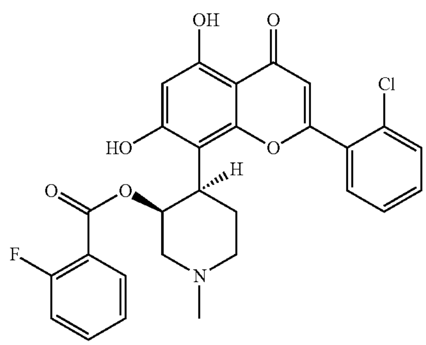 [SMILES: CN1CC[C@H](c2c(O)cc(O)c3c(=O)cc(-c4ccccc4Cl)oc23)[C@H](OC(=O)c2ccccc2F)C1] |
| 35 | 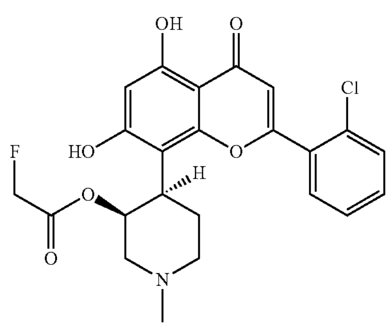 [SMILES: CN1CC[C@H](c2c(O)cc(O)c3c(=O)cc(-c4ccccc4Cl)oc23)[C@H](OC(=O)CF)C1] |
| 36 | 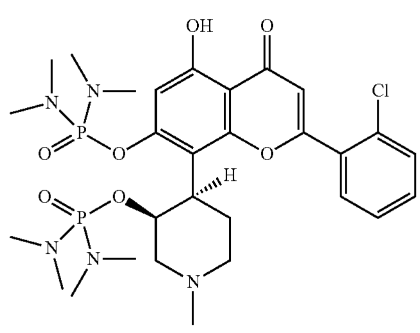 [SMILES: CN1CC[C@H](c2c(OP(=O)(N(C)C)N(C)C)cc(O)c3c(=O)cc(-c4ccccc4Cl)oc23)[C@H](OP(=O)(N(C)C)N(C)C)C1] |

TABLE 2-continued

Example Compounds

| Compound Number | Compound Structure |
|---|---|
| 37 | 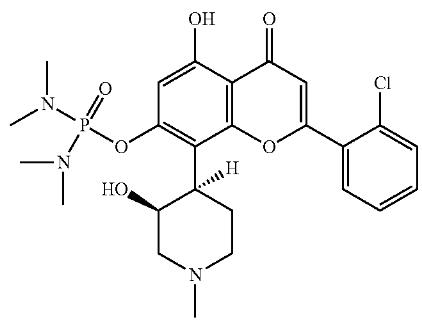 [SMILES: CN1CC[C@H](c2c(OP(=O)(N(C)C)N(C)C)cc(O)c3c(=O)cc(-c4ccccc4Cl)oc23)[C@H](O)C1] |
| 38 | 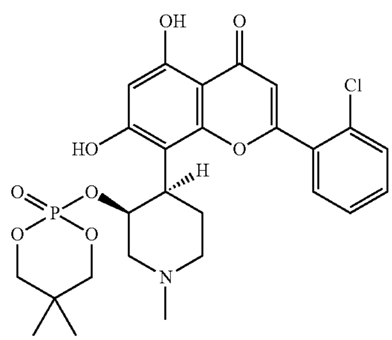 [SMILES: CN1CC[C@H](c2c(O)cc(O)c3c(=O)cc(-c4ccccc4Cl)oc23)[C@H](OP2(=O)OCC(C)(C)CO2)C1] |
| 39 | 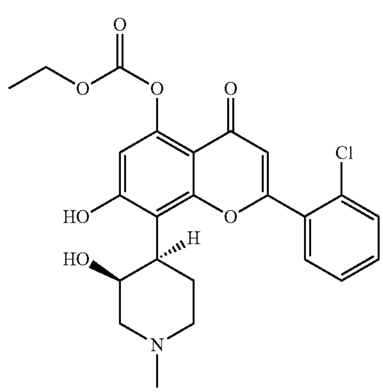 [SMILES: CCOC(=O)Oc1cc(O)c([C@H]2CCN(C)C[C@H]2O)c2oc(-c3ccccc3Cl)cc(=O)c12] |
| 40 | 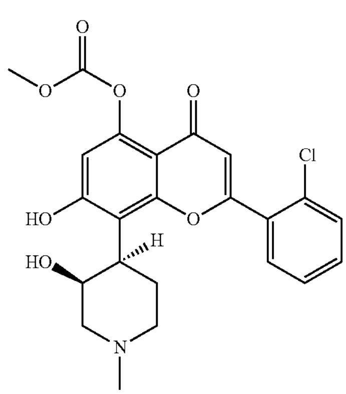 [SMILES: COC(=O)Oc1cc(O)c([C@H]2CCN(C)C[C@H]2O)c2oc(-c3ccccc3Cl)cc(=O)c12] |

TABLE 2-continued

Example Compounds

| Compound Number | Compound Structure |
|---|---|
| 41 | 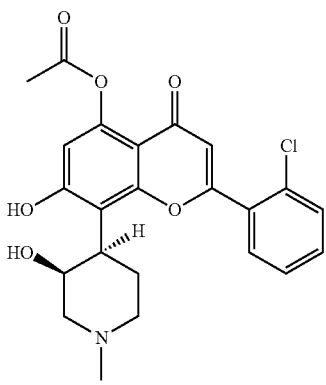 [SMILES: CC(=O)Oc1cc(O)c([C@H]2CCN(C)C[C@H]2O)c2oc(-c3ccccc3Cl)cc(=O)c12] |
| 42 | 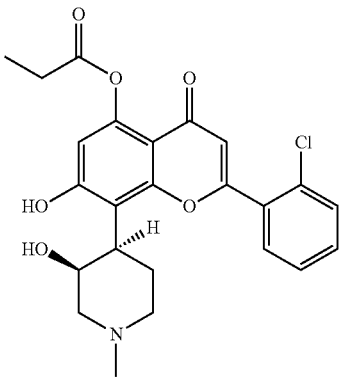 |

In some embodiments, any of the foregoing compounds are in the form of a pharmaceutically acceptable salt. The salt may be an acid addition salt or a base addition salt. For example, the salt may be an amine salt formed by protonation of the N-methyl piperazine moiety (e.g., HCl salt and the like) or a sodium salt. In other embodiments, the salt is formed at a phosphate, and the compounds are in the form of mono- or di-salts of the phosphate group (e.g., mono- or disodium phosphate salt and the like). All pharmaceutically acceptable salts of the foregoing compounds are included in the scope of the invention.

Also provided are pharmaceutical compositions comprising a pharmaceutically acceptable carrier or excipient and any of the foregoing compounds (e.g., a compound of structure (I) or (I')). Advantageously, the presently disclosed compounds have increased bioavailability relative to the alvocidib parent compound, and thus certain embodiments are directed to the foregoing pharmaceutical compositions formulated for oral delivery. Any of the carriers and/or excipients known in the art for oral formulation may be used in these embodiments, in addition to other carriers and/or excipients derivable by one of ordinary skill in the art.

For the purposes of administration, the compounds of the present invention may be administered as a raw chemical or may be formulated as pharmaceutical compositions. Embodiments of the pharmaceutical compositions of the present invention comprise a compound of structure (I) and a pharmaceutically acceptable carrier, diluent or excipient. The compound of structure (I) is present in the composition in an amount which is effective to treat a particular disease or condition of interest—that is, typically in an amount sufficient to treat a disease associated with overexpression of a cyclin-dependent kinase (CDK), and preferably with acceptable toxicity to the patient. Bioavailability of compounds of structure (I) can be determined by one skilled in the art, for example, by plasma concentration at various time intervals. Appropriate concentrations and dosages can be readily determined by one skilled in the art.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of embodiments of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of some embodiments of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of some embodiments of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of certain embodiments of the invention intended for either parenteral or oral administration should contain an amount of a compound of the invention such that a suitable dosage will be obtained.

In some embodiments, the pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of various embodiments of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

Embodiments of the pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of some embodiments of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of other embodiments of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, sub-containers, and the like, which together may form a kit. One skilled in the art, without undue experimentation may determine preferred aerosols.

In some embodiments, the pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In some embodiments, the concentration of the compound of structure (I) provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of the compound of structure (I) provided in the pharmaceutical compositions of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of the compound of structure (I) provided in the pharmaceutical compositions of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of the compound of structure (I) provided in the pharmaceutical compositions of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount the compound of structure (I) provided in the pharmaceutical compositions of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the compound of structure (I) provided in the pharmaceutical compositions of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of the compound of structure (I) provided in the pharmaceutical compositions of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

It will also be appreciated by those skilled in the art that, in the processes for preparing compounds of structure (I) described herein, the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

Compounds of structure (I) can be prepared by addition of an appropriate substituent to one or more of the three free hydroxyls of alvocidib. The alvocidib parent compound (and salts and solvates thereof) can be purchased from commercial sources or prepared according to methods known in the art, for example as described in U.S. Pat. Nos. 6,136,981; 6,225,473; 6,406,912; 6,576,647; and 6,821,990; the full disclosures of which are herein incorporated by reference in their entireties.

The following General Reaction Scheme illustrates a method of making compounds of this invention, i.e., compound of structure (I):

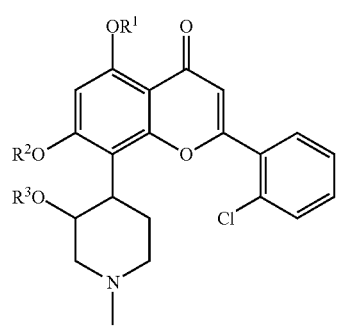

(I)

or a stereoisomer, tautomer or pharmaceutically acceptable salt thereof, wherein $R^1$, $R^2$ and $R^3$ are as defined above. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

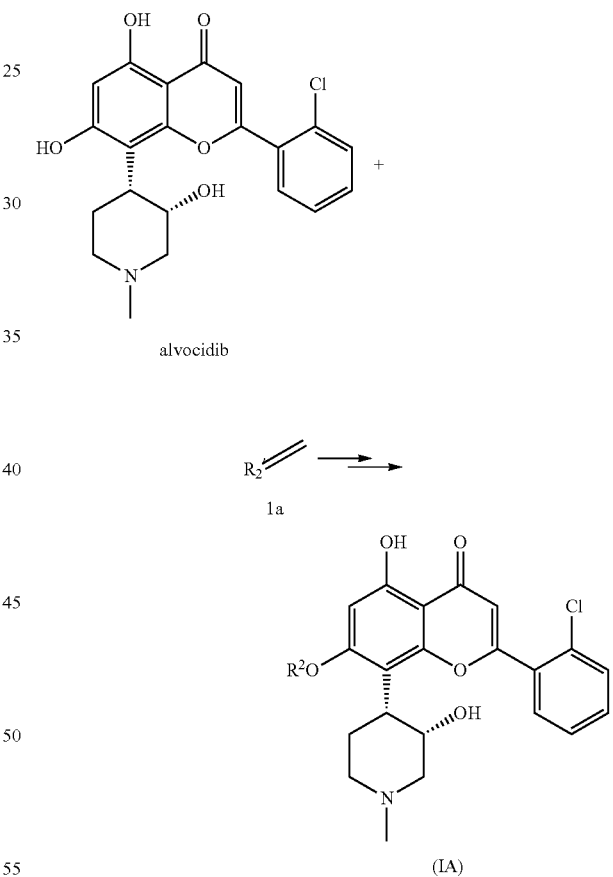

General Reaction Scheme 1 provides an exemplary method for preparation of compounds of structure (IA). $R^2$ in General Reaction Scheme 1 is defined herein, and $R^{2'}$ refers to a one-carbon shorter homologue of $R^2$. As shown, alvocidib can be reacted with a protected alkenyl 1a under appropriate coupling conditions (e.g., NaOEt in ethanol). The resultant product can then be de-protected under suitable conditions (e.g., TMSBr) to yield the desired compound of structure (IA) in two reaction steps.

General Reaction Scheme 2

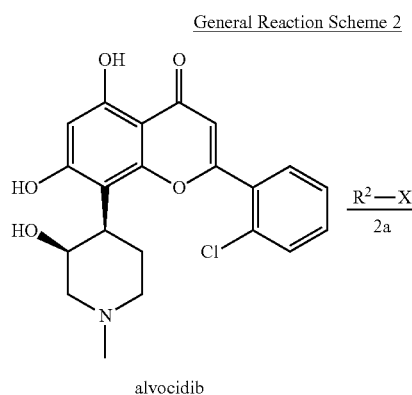

alvocidib

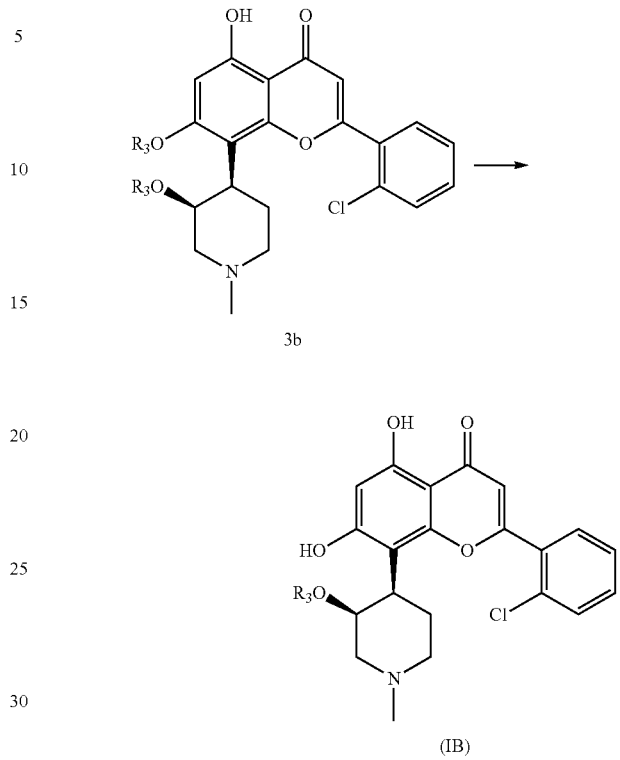

General Reaction Scheme 2, provides another exemplary method for preparation of compounds of structure (IA). $R^2$ in General Reaction Scheme 2 is defined herein, and X is a halide (e.g., Cl). Alvocidib can be reacted with a suitable halo-phosphoryl reagent 2a (e.g., ethyl (chloro(ethoxy)phosphoryl)-L-alaninate) under appropriate conditions (e.g., N-methyl pyridine and $Et_3N$) to yield the desired compound of structure (IA).

Alternatively, alvocidib can be reacted with a suitable halide reagent including for example, an acid chloride, a carbonochloridate, or a carbamic chloride under suitable reaction conditions (e.g., N-methyl pyridine and $Et_3N$). Each halide reagent can be selected to yield a desired ester, carbonate or carbamate, respectively, of compound of structure (IA) in one reaction step.

General Reaction Scheme 3

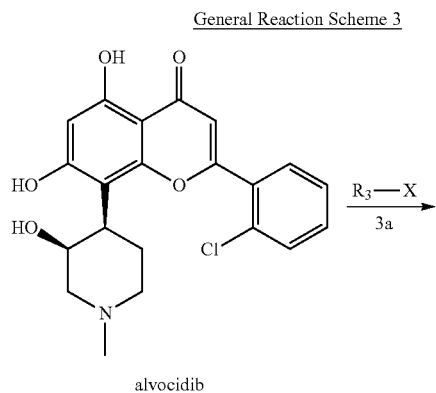

alvocidib

General Reaction Scheme 3, provides an exemplary method for preparation of compounds of structure (IB). $R^3$ in General Reaction Scheme 3 is defined herein, and X is a halide (e.g., Cl). In a first step, alvocidib can be treated with 2 equivalents of a suitable halide reagent 3a (e.g., acid chloride, a carbonochloridate, or a carbamic chloride) under basic conditions (for example, $Et_3N$) to react with two of the free hydroxyl groups of the starting material. In a second step, one of the hydroxyl groups can be regenerated by selectively removing one of the substituents under suitable conditions (e.g., aq. $NH_3$ in EtOH). Thus, the desired compound of structure (IB) can be obtained in two reaction steps.

General Reaction Scheme 4

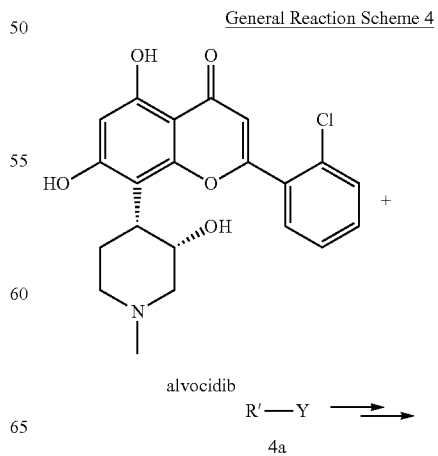

alvocidib

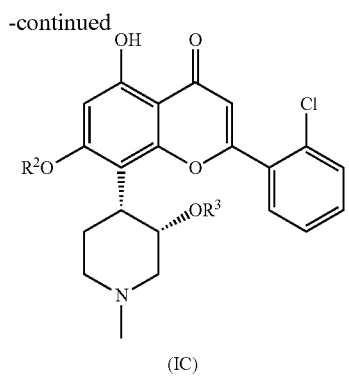

(IC)

General Reaction Scheme 4 provides an exemplary method for preparation of compounds of structure (IC). $R^2$ and $R^3$ in General Reaction Scheme 4 are defined herein, and Y is a halide or a hydroxyl, R' is —P(=O)(OR$^h$)$_2$ or —C(=O)R$^b$ with R$^b$ and R$^h$ as defined herein.

As shown in General Reaction Scheme 4, alvocidib can be reacted with a molar excess of a phosphonate 4a (e.g., diethyl hydrogen phosphate) to couple with two of the free hydroxyl groups of the starting material under appropriate conditions (e.g., with a catalytic amount of $I_2$). The resultant product can be isolated to yield the desired product of structure (IC).

Alternatively, alvocidib can be treated as described in General Reaction Scheme 3 when reagent 4a is an acid chloride, a carbonochloridate, or a carbamic chloride under basic conditions (e.g., Et$_3$N). The resultant product can then be used without the selective regeneration of the hydroxyl group to yield a compound according to structure (IC) in one step.

It will be apparent to one of ordinary skill in the art that compounds of structure (I) having a functional groups attached at any one or two of the three hydroxyl groups of alvocidib can be prepared according to the above schemes, and the desired regioisomer separated by usual techniques, such as chromatography. Protecting group strategies for optimizing the yield of the desired regioisomer will also be apparent to one of ordinary skill in the art.

II. Methods

In various embodiments, the invention provides a method for treating a disease in a mammal in need thereof by administration of a compound of structure (I), or a pharmaceutical composition comprising the same, to the mammal. In some specific embodiments, the method is for treating a disease associated with overexpression of a cyclin-dependent kinase (CDK) in a mammal in need thereof, the method comprising administering a therapeutically effective amount of any of the foregoing compounds of structure (I), or a pharmaceutical composition comprising the same, to the mammal.

In some more embodiments, the disease is cancer, for example a hematologic cancer. In some of these embodiments, the hematologic cancer is selected from acute myelogenous leukemia (AML), multiple myeloma, follicular lymphoma, acute lymphoblastic leukemia (ALL), chronic lymphocytic leukemia (CLL) and non-Hodgkin's lymphoma. In other embodiments, the hematological cancer is acute myelogenous leukemia (AML). In other different embodiments, the hematologic cancer is chronic lymphocytic leukemia (CLL). In still more different embodiments, the hematologic cancer is myelodysplasic syndrome (MDS).

In some other specific embodiments of the foregoing methods, the method comprises orally administering the compound of structure (I), or the pharmaceutical composition comprising the same, to the mammal.

In addition to the above exemplary diseases, a wide variety of cancers, including solid tumors and leukemias (e.g., acute myeloid leukemia) are amenable to the methods disclosed herein. Types of cancer that may be treated in various embodiments include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include, but are not limited to, angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

The compounds of the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the invention is administered in a single dose. A single dose of a compound of the invention may also be used for treatment of an acute condition.

In some embodiments, a compound of the invention is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

In some embodiments, the compounds of the invention are administered in dosages. Due to intersubject variability in compound pharmacokinetics, individualization of dosing regimen is provided in certain embodiments. Dosing for a compound of the invention may be found by routine experimentation in light of the instant disclosure and/or can be derived by one of ordinary skill in the art.

EXAMPLES

Example 1

Preparation of Compound 15

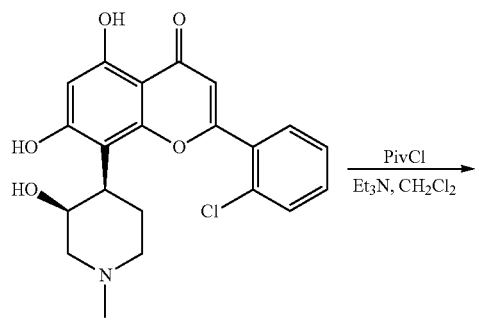

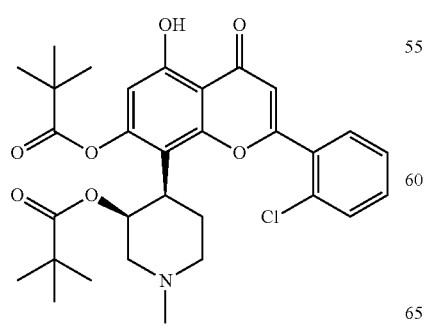

Example 2

Preparation of Compound 1

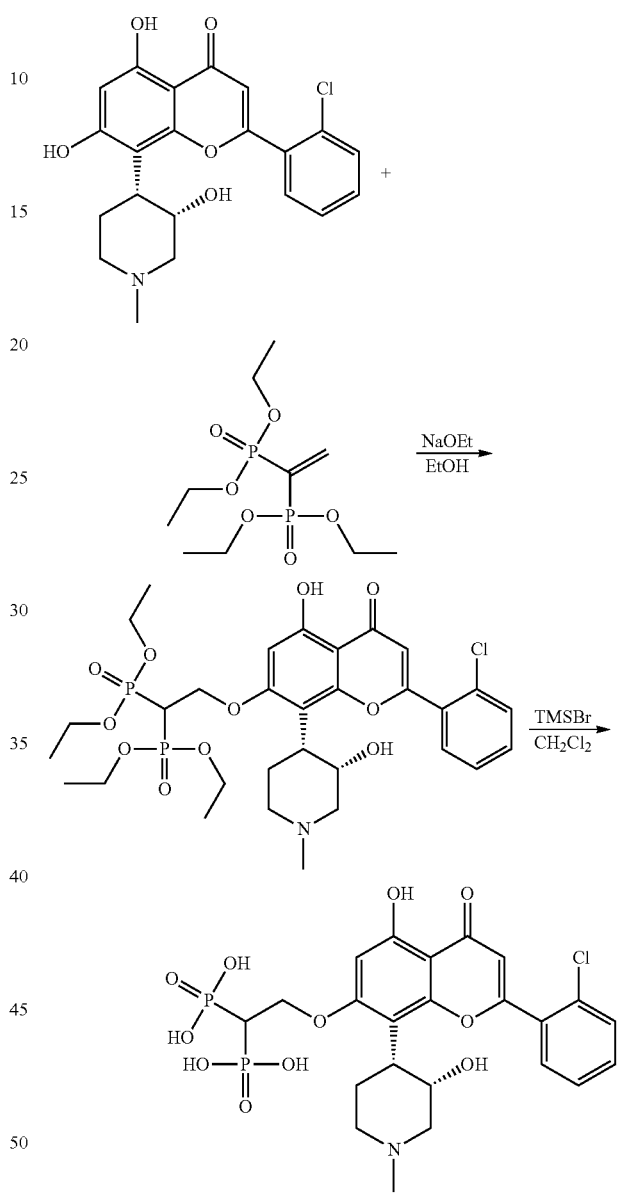

Example 3

Preparation of Compound 3

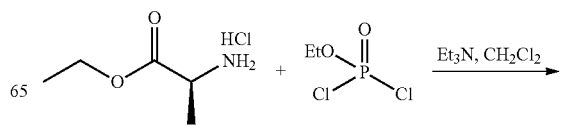

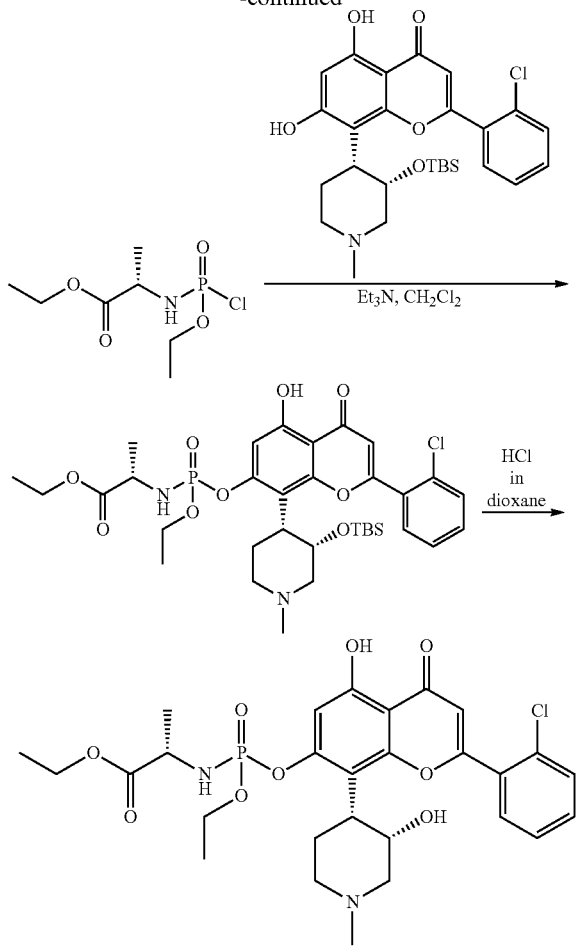

Ethyl (chloro (ethoxy)phosphoryl)-L-alaninate

To a stirred solution of ethyl phosphorodichloridate (2 g, 12.3 mmol, 1 eq) in dichloromethane (20 mL) was added triethylamine (5.13 mL, 36.6 mmol, 3.0 eq) at −78° C., ethyl L-alaninate hydrochloride (0.41 g, 0.75 mmol, 1.1 eq) was added dropwise. The reaction mixture was stirred for 2 hours at room temperature. After confirming the reaction by TLC, the reaction mixture was quenched with ice cold water (50 mL) and extracted with dichloromethane, washed with water and brine solution. The organic layer was dried over sodium sulfate and solvent was evaporated under vacuum to afford crude ethyl (chloro (ethoxy) phosphoryl)-L-alaninate as a white solid (2 g, 66%); $^1$H NMR (400 MHz, DMSO-$d_6$) δ: 10.61 (s, 1H), 4.04-4.09 (m, 1H), 3.01-3.07 (m, 4H), 1.18-1.21 (m, 9H).

Ethyl (((8-((3S, 4R)-3-((tert-butyldimethylsilyl)oxy)-1-methylpiperidin-4-yl)-2-(2-chlorophenyl)-5-hydroxy-4-oxo-4H-chromen-7-yl)oxy)(ethoxy)phosphoryl)-L-alaninate To a stirred solution of 8-((3S, 4R)-3-((tert-butyldimethylsilyl)oxy)-1-methylpiperidin-4-yl)-2-(2-chlorophenyl)-5,7-dihydroxy-4H-chromen-4-one (0.5 g, 0.97 mmol, 1 eq) in dichloromethane (10 mL) at 0° C., triethylamine (0.68 mL, 4.85 mmol, 3.0 eq) and ethyl (chloro(ethoxy)phosphoryl)-L-alaninate (in dichloromethane) (0.147 g, 1.94 mmol, 2 eq) were added dropwise. The reaction mixture was stirred for 5 hours at room temperature. After confirming the reaction by LC/MS, the reaction mixture was quenched with ice cold water (20 mL) and extracted with dichloromethane, washed with water and brine solution. The organic layer was dried over sodium sulfate and solvent was evaporated under vacuum. The crude residue obtained was purified by preparative HPLC to afford ethyl (((8-((3 S, 4R)-3-((tert-butyldimethylsilyl)oxy)-1-methylpiperidin-4-yl)-2-(2-chlorophenyl)-5-hydroxy-4-oxo-4H-chromen-7-yl)oxy)(ethoxy)phosphoryl)-L-alaninate as an off white solid (0.2 g, 28%). LC/MS m/z: 723.2 [M+H]$^+$; HPLC Purity: 95.32%.

Ethyl (((2-(2-chlorophenyl)-5-hydroxy-8-((3S, 4R)-3-hydroxy-1-methylpiperidin-4-yl)-4-oxo-4H-chromen-7-yl)oxy)(ethoxy)phosphoryl)-L-alaninate To a stirred solution of (3 S, 4R)-4-(2-(2-chlorophenyl)-5,7-dihydroxy-4-oxo-4H-chromen-8-yl)-1-methylpiperidin-3-yl (tert-butoxycarbonyl)-L-valinate (0.2 g, 0.27 mmol, 1 eq) in dichloromethane (5 mL) at 0° C., 2.0 M HCl in dioxane (2.0 mL, 2.0 eq) was added. The reaction mixture was stirred for 2 hours at room temperature. After confirming the reaction by LC/MS, the reaction mixture was concentrated. The crude residue obtained was purified by preparative HPLC to afford ethyl (((2-(2-chlorophenyl)-5-hydroxy-8-((3 S, 4R)-3-hydroxy-1-methylpiperidin-4-yl)-4-oxo-4H-chromen-7-yl)oxy)(ethoxy) phosphoryl)-L-alaninate as an off white solid (0.05 g, 30%). LC/MS m/z: 609.1 [M+H]$^+$; HPLC Purity: 95.82%; 1H NMR (400 MHz, DMSO-$d_6$) δ: 12.94 (s, 1H), 7.56-7.97 (m, 4H), 6.99 (s, 1H), 6.72 (s, 1H), 6.24-6.30 (m, 1H), 4.03-4.43 (m, 5H), 3.77-3.88 (m, 2H), 3.20 (t, J=12.04 Hz, 1H), 2.83-2.85 (m, 3H), 2.09-2.15 (m, 4H), 1.90 (s, 1H), 1.53 (s, 1H), 1.12-1.31 (m, 9H).

Example 4

Preparation of Compound 14

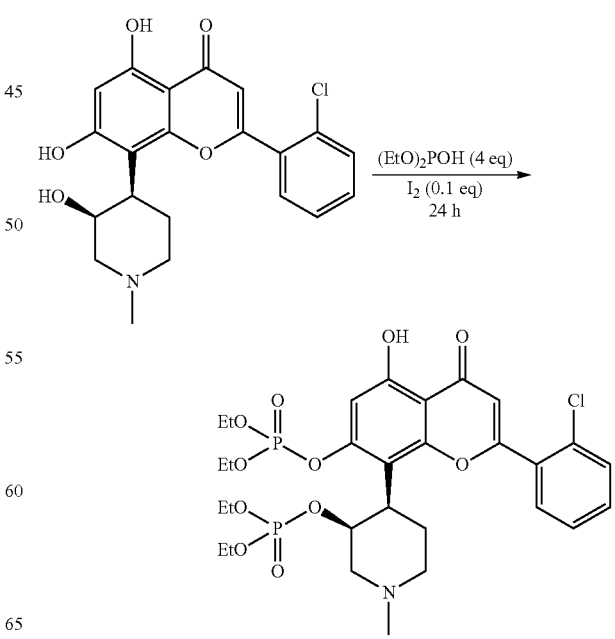

Example 5

Preparation of Compound 10

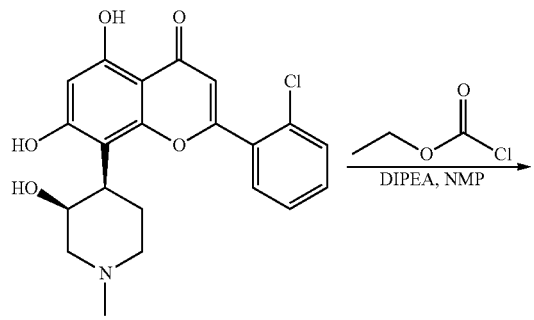

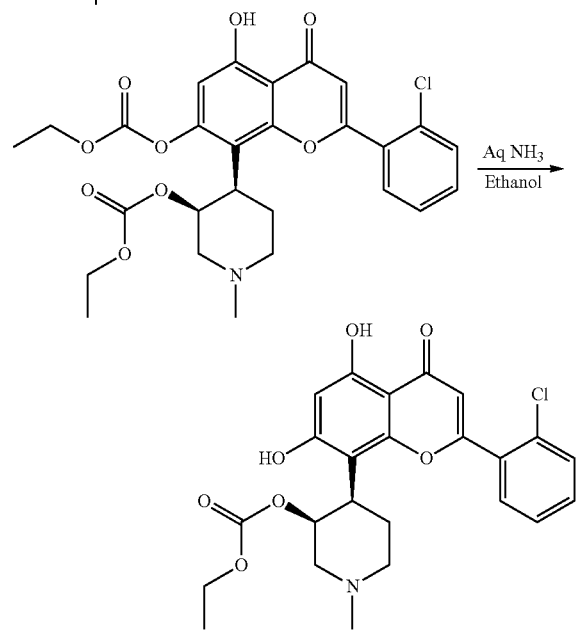

2-(2-chlorophenyl)-8-((3S, 4R)-3-((ethoxycarbonyl)oxy)-1-methylpiperidin-4-yl)-5-hydroxy-4-oxo-4H-chromen-7-yl ethyl carbonate To a stirred solution of 2-(2-chlorophenyl)-5,7-dihydroxy-8-((3S, 4R)-3-hydroxy-1-methylpiperidin-4-yl)-4H-chromen-4-one (1 g, 2.28 mmol, 1.0 eq) in NMP (10 mL) at 0° C., diisopropylamine (1.2 mL, 6.86 mmol, 3.0 eq) and ethylchloroformate (0.19 mL, 2.28 mmol, 1.0 eq) were added dropwise. The reaction mixture was stirred for 6 hours at room temperature. After confirming the reaction by TLC, the reaction mixture was quenched with ice cold water (20 mL). The solid precipitated was filtered. Crude solid obtained was lyophilized to afford 2-(2-chlorophenyl)-8-((3S,4R)-3-((ethoxycarbonyl)oxy)-1-methylpiperidin-4-yl)-5-hydroxy-4-oxo-4H-chromen-7-yl ethyl carbonate as a yellow solid (0.45 g). LC/MS m/z: 546.2 [M+H]$^+$.

(3S, 4R)-4-(2-(2-chlorophenyl)-5,7-dihydroxy-4-oxo-4H-chromen-8-yl)-1-methylpiperidin-3-yl ethyl carbonate To a stirred solution of 2-(2-chlorophenyl)-8-((3S, 4R)-3-((ethoxycarbonyl)oxy)-1-methylpiperidin-4-yl)-5-hydroxy-4-oxo-4H-chromen-7-yl ethyl carbonate (0.45 g, 0.82 mmol, 1 eq) in ethanol (10 mL) at 0° C., aqueous ammonia (4.5 mL) was added. The reaction mixture was stirred for 2 hours at room temperature. After confirming the reaction by LC/MS, the reaction mixture was concentrated. The crude residue obtained was purified by preparative HPLC to afford (3 S, 4R)-4-(2-(2-chlorophenyl)-5,7-dihydroxy-4-oxo-4H-chromen-8-yl)-1-methylpiperidin-3-yl ethyl carbonate as a yellow solid (0.280 g, 71%). LC/MS m/z: 474 [M+H]$^+$; HPLC Purity: 99.50%; $^1$H NMR (400 MHz, DMSO-d$_6$) δ: 12.98 (s, 1H), 11.17 (s, 1H), 7.91 (d, J=7.60 Hz, 1H), 7.72 (d, J=7.60 Hz, 1H), 7.57-7.64 (m, 2H), 6.58 (s, 1H), 6.36 (s, 1H), 4.84 (s, 1H), 3.86-3.92 (m, 2H), 3.33 (s, 1H), 2.84-3.02 (m, 3H), 2.18 (s, 5H), 1.62 (d, J=11.20 Hz, 1H), 1.01 (t, J=6.80 Hz, 3H)

Example 6

Preparation of Compound 11

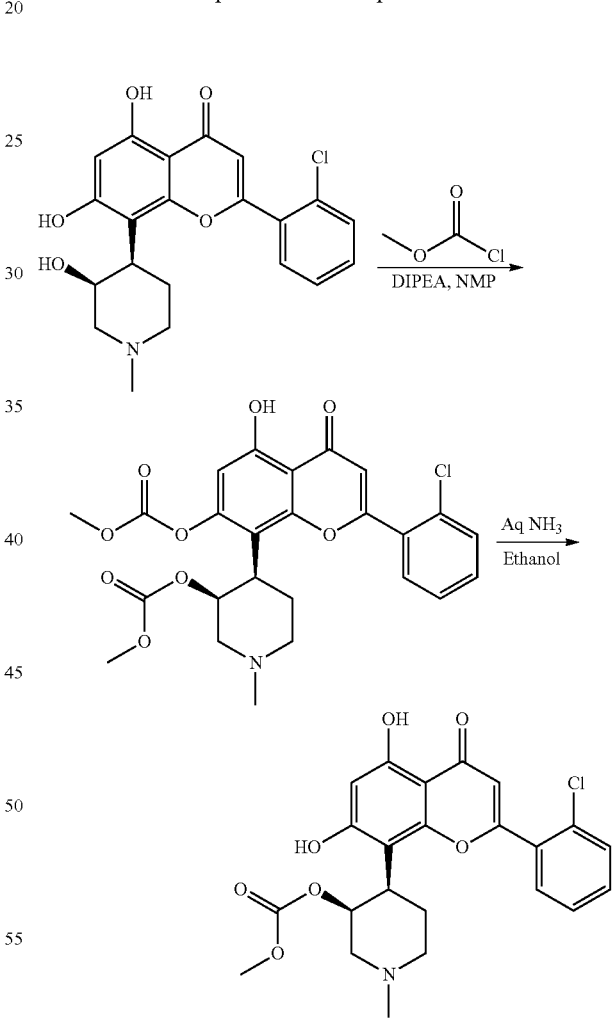

2-(2-chlorophenyl)-5-hydroxy-8-((3S, 4R)-3-((methoxycarbonyl)oxy)-1-methylpiperidin-4-yl)-4-oxo-4H-chromen-7-yl methyl carbonate To a stirred solution of 2-(2-chlorophenyl)-5,7-dihydroxy-8-((3S, 4R)-3-hydroxy-1-methylpiperidin-4-yl)-4H-chromen-4-one (1 g, 2.28 mmol, 1.0 eq) in NMP (10 mL) at 0° C., diisopropylamine (1.2 mL, 6.86 mmol, 3.0 eq) and methylchloroformate (0.16 mL, 2.28 mmol, 1.0 eq) were added dropwise. The reaction mixture was stirred for 6 hours at room temperature. After confirming the reaction by TLC, the reaction mixture was quenched with ice cold water (20 mL). The solid precipitate was filtered. Crude solid obtained was lyophilized to afford 2-(2-chlorophenyl)-5-hydroxy-8-((3 S, 4R)-3-((methoxycarbonyl)oxy)-1-methylpiperidin-4-yl)-4-oxo-4H-chromen-7-yl methyl carbonate as a yellow solid (1 g). LC/MS m/z: 518.2 [M+H]$^+$.

(3S, 4R)-4-(2-(2-chlorophenyl)-5,7-dihydroxy-4-oxo-4H-chromen-8-yl)-1-methylpiperidin-3-yl methyl carbonate To a stirred solution of 2-(2-chlorophenyl)-8-((3S, 4R)-3-((ethoxycarbonyl)oxy)-1-methylpiperidin-4-yl)-5-hydroxy-4-oxo-4H-chromen-7-yl ethyl carbonate (1 g, 1.9 mmol, 1 eq) in ethanol (10 mL) at 0° C., aqueous ammonia (10 mL) was added. The reaction mixture was stirred for 2 hours at room temperature. After confirming the reaction by LC/MS, the reaction mixture was concentrated. The crude residue obtained was purified by preparative HPLC to afford (3 S, 4R)-4-(2-(2-chlorophenyl)-5,7-dihydroxy-4-oxo-4H-chromen-8-yl)-1-methylpiperidin-3-yl methyl carbonate as a yellow solid (0.81 g, 91%). LC/MS m/z: 460.0 [M+H]$^+$; HPLC Purity: 92.28%; $^1$H NMR (400 MHz, DMSO-d$_6$) δ: 12.98 (s, 1H), 11.32 (s, 1H), 7.89 (d, J=7.20 Hz, 1H), 7.72 (d, J=7.60 Hz, 1H), 7.57-7.65 (m, 2H), 6.56 (s, 1H), 6.33 (s, 1H), 4.79 (s, 1H), 3.48-3.49 (m, 3H), 3.29-3.35 (m, 2H), 2.97 (d, J=12.40 Hz, 1H), 2.84 (d, J=11.20 Hz, 2H), 2.13-2.19 (m, 4H), 1.94 (d, J=23.60 Hz, 1H), 1.59 (d, J=11.20 Hz, 1H).

Example 7

Preparation of Compound 12

(3S, 4R)-4-(2-(2-chlorophenyl)-5,7-dihydroxy-4-oxo-4H-chromen-8-yl)-1-methylpiperidin-3-yl ethylcarbamate To a stirred solution of 2-(2-chlorophenyl)-5,7-dihydroxy-8-((3S, 4R)-3-hydroxy-1-methylpiperidin-4-yl)-4H-chromen-4-one (1 g, 2.28 mmol, 1.0 eq) in NMP (10 mL) at 0° C., diisopropylamine (1.2 mL, 6.86 mmol, 3.0 eq) and ethylcarbamic chloride (0.25 g, 2.28 mmol, 1.0 eq) were added dropwise. The reaction mixture was stirred for 6 hours at room temperature. After confirming the reaction by TLC, the reaction mixture was quenched with ice cold water (20 mL). The solid precipitated was filtered. The solid obtained was lyophilized to afford (3 S, 4R)-4-(2-(2-chlorophenyl)-5,7-dihydroxy-4-oxo-4H-chromen-8-yl)-1-methylpiperidin-3-yl ethylcarbamate as a yellow solid (0.69 g, 69%). 5 LC/MS m/z: 471.0 [M+H]$^+$; HPLC Purity: 98.32%; $^1$H NMR (400 MHz, DMSO-d$_6$) δ: 12.97 (s, 1H), 10.67 (s, 1H), 7.56-7.79 (m, 4H), 6.50 (s, 1H), 6.33 (s, 1H), 6.11 (s, 1H), 4.92 (s, 1H), 3.28-3.32 (m, 1H), 2.77-3.06 (m, 5H), 2.15 (d, J=5.84 Hz, 4H), 1.96 (t, J=11.48 Hz, 1H), 1.66 (d, J=11.28 Hz, 1H), 0.85 (t, J=7.04 Hz, 3H).

Example 8

Preparation of Compound 13

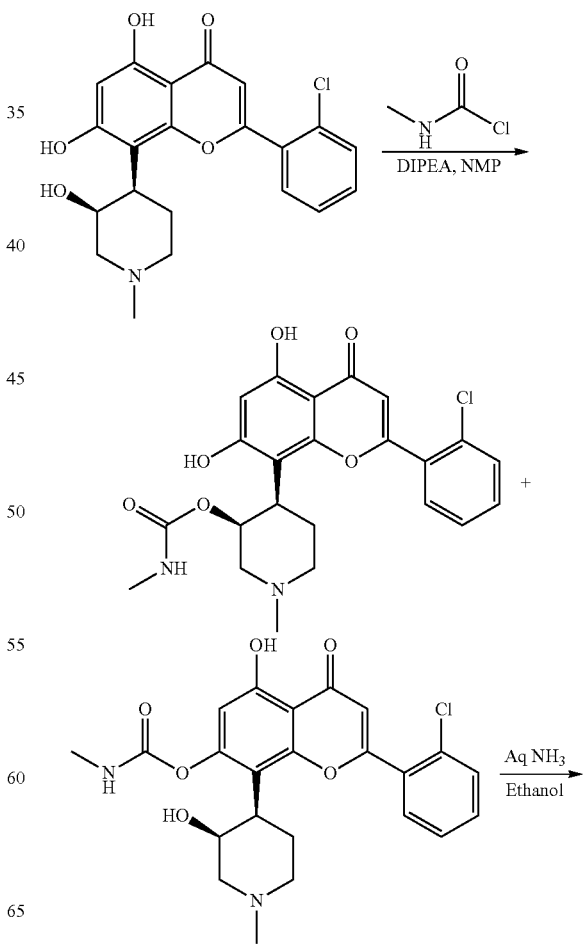

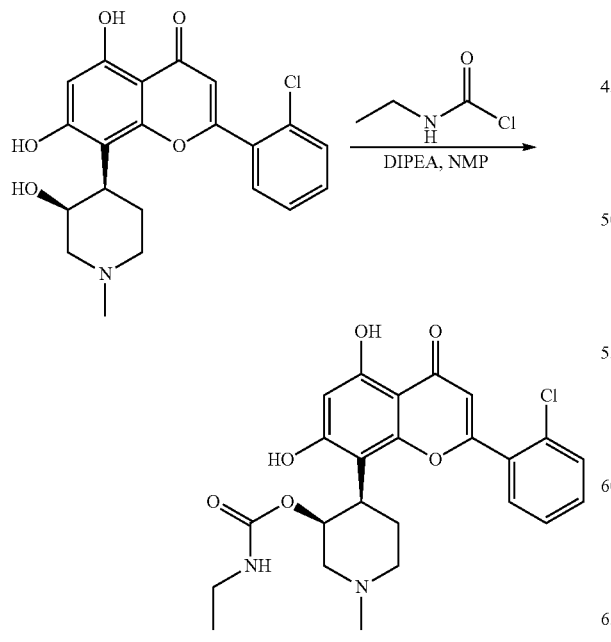

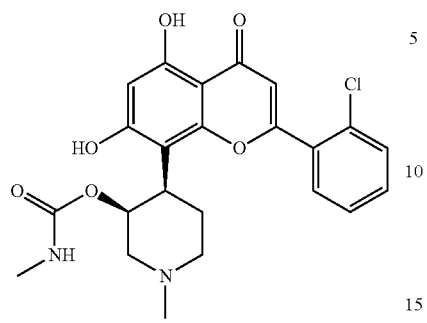

2-(2-chlorophenyl)-5-hydroxy-8-((3S, 4R)-1-methyl-3-((methylcarbamoyl)oxy)piperidin-4-yl)-4-oxo-4H-chromen-7-yl methylcarbamate To a stirred solution of 2-(2-chlorophenyl)-5,7-dihydroxy-8-((3S, 4R)-3-hydroxy-1-methylpiperidin-4-yl)-4H-chromen-4-one (1 g, 2.28 mmol, 1.0 eq) in NMP (10 mL) at 0° C., diisopropylamine (1.2 mL, 6.86 mmol, 3.0 eq) and methylcarbamic chloride (0.21 mL, 2.28 mmol, 1.0 eq) were added dropwise. The reaction mixture was stirred for 2 hours at room temperature. After confirming the reaction by TLC, the reaction mixture was quenched with ice cold water (20 mL). The solid precipitated was filtered. Crude solid obtained was lyophilized to afford mixture of 2-(2-chlorophenyl)-5-hydroxy-8-((3 S, 4R)-3-hydroxy-1-methylpiperidin-4-yl)-4-oxo-4H-chromen-7-yl methylcarbamate and (3 S, 4R)-4-(2-(2-chlorophenyl)-5,7-dihydroxy-4-oxo-4H-chromen-8-yl)-1-methylpiperidin-3-yl methylcarbamate as a yellow solid (1 g). LC/MS m/z: 459.0 [M+H]$^+$.

(3S, 4R)-4-(2-(2-chlorophenyl)-5,7-dihydroxy-4-oxo-4H-chromen-8-yl)-1-methylpiperidin-3-yl methylcarbamate To a stirred solution of 2-(2-chlorophenyl)-5-hydroxy-8-((3S, 4R)-3-hydroxy-1-methylpiperidin-4-yl)-4-oxo-4H-chromen-7-yl methylcarbamate and (3 S, 4R)-4-(2-(2-chlorophenyl)-5,7-dihydroxy-4-oxo-4H-chromen-8-yl)-1-methylpiperidin-3-yl methylcarbamate (1 g, 1.9 mmol, 1 eq) in ethanol (10 mL) at 0° C., aqueous ammonia (10 mL) was added. The reaction mixture was stirred for 2 hour at room temperature. After confirming the reaction by LC/MS, the reaction mixture was concentrated. The crude residue obtained was purified by preparative HPLC to afford (3 S, 4R)-4-(2-(2-chlorophenyl)-5,7-dihydroxy-4-oxo-4H-chromen-8-yl)-1-methylpiperidin-3-yl methyl carbonate as a yellow solid (0.81 g, 91%). LC/MS m/z: 459.0 [M+H]$^+$; HPLC Purity: 95.32%; 1H NMR (400 MHz, DMSO-d$_6$) δ: 12.79 (s, 1H), 10.65 (s, 1H), 7.59-7.78 (m, 4H), 6.49 (s, 1H), 6.33 (s, 1H), 6.00 (s, 1H), 4.89 (s, 1H), 3.29-3.33 (m, 2H), 2.84-3.04 (m, 3H), 2.40-2.41 (m, 3H), 2.14-2.15 (m, 4H), 1.97 (t, J=12.00 Hz, 1H), 1.64 (d, J=12.00 Hz, 1H).

Example 9

Preparation of Compound 16

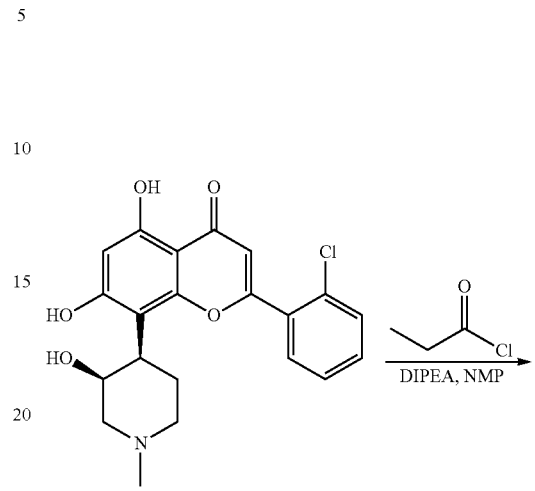

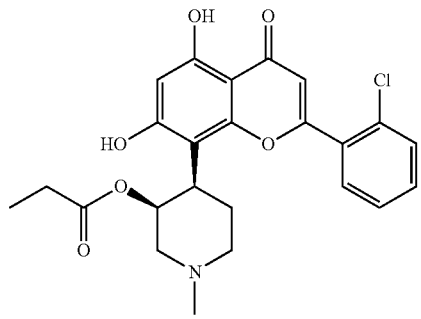

(3S, 4R)-4-(2-(2-chlorophenyl)-5,7-dihydroxy-4-oxo-4H-chromen-8-yl)-1-methylpiperidin-3-yl propionate To a stirred solution of 2-(2-chlorophenyl)-5,7-dihydroxy-8-((3S, 4R)-3-hydroxy-1-methylpiperidin-4-yl)-4H-chromen-4-one (1 g, 2.28 mmol, 1.0 eq) in NMP (5 mL) at 0° C., diisopropylamine (1.2 mL, 6.36 mmol, 3.0 eq) and propionyl chloride (0.19 mL, 1.14 mmol, 1.0 eq) were added dropwise. The reaction mixture was stirred for 6 hours at room temperature. After confirming the reaction by TLC, the reaction mixture was quenched with ice cold water (20 mL). The solid precipitated was filtered. The crude residue obtained was purified by preparative HPLC to afford (3 S, 4R)-4-(2-(2-chlorophenyl)-5,7-dihydroxy-4-oxo-4H-chromen-8-yl)-1-methylpiperidin-3-yl propionate as a yellow solid (0.15 g, 22%). LC/MS m/z: 458.4 [M+H]$^+$; HPLC Purity: 92.17%; 1H NMR (400 MHz, DMSO-d$_6$) δ: 12.95 (s, 1H), 11.02 (s, 1H), 7.58-7.81 (m, 4H), 6.57 (s, 1H), 6.34 (s, 1H), 4.98 (s, 1H), 3.30-3.33 (m, 2H), 2.85-2.92 (m, 3H), 1.94-2.13 (m, 7H), 1.67 (d, J=12.00 Hz, 1H), 0.76-0.80 (m, 3H).

Example 10

Preparation of Compound 21

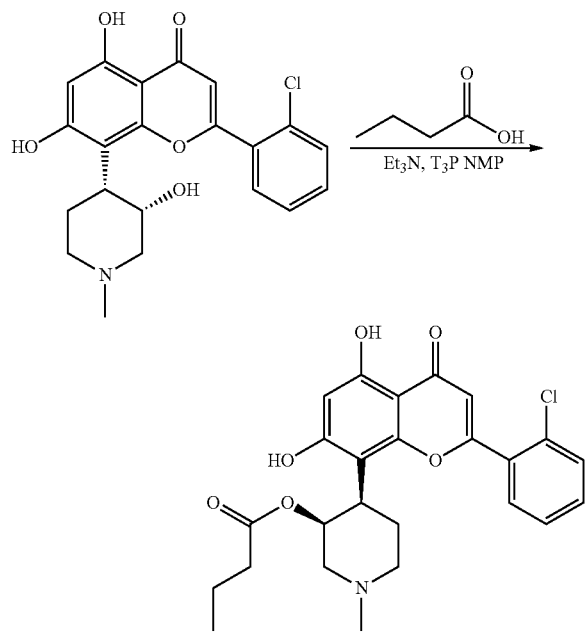

(3S, 4R)-4-(2-(2-chlorophenyl)-5,7-dihydroxy-4-oxo-4H-chromen-8-yl)-1-methylpiperidin-3-yl butyrate To a stirred solution of 2-(2-chlorophenyl)-5,7-dihydroxy-8-((3S, 4R)-3-hydroxy-1-methylpiperidin-4-yl)-4H-chromen-4-one (0.3 g, 0.686 mmol, 1 eq) and butyric acid (0.06 g, 0.686 mmol, 1.0 eq) in dimethylformamide (5 mL) at 0° C., Triethylamine (0.32 mL, 2.051 mmol, 3.0 eq) and T$_3$P (0.43 mL, 1.37 mmol, 2.0 eq) were added. The reaction mixture was stirred for 16 hours at room temperature. After confirming the reaction by TLC, the reaction mixture was concentrated. The crude residue obtained was purified by preparative HPLC to afford (3 S, 4R)-4-(2-(2-chlorophenyl)-5,7-dihydroxy-4-oxo-4H-chromen-8-yl)-1-methylpiperidin-3-yl butyrate as an off white solid (0.03 g, 12%). LC/MS m/z: 472.1 [M+H]$^+$; HPLC Purity: 97.04%; $^1$H NMR (400 MHz, DMSO-d$_6$) δ: 12.97 (s, 1H), 11.43 (s, 1H), 9.83 (s, 1H), 7.64-7.85 (m, 4H), 6.61 (s, 1H), 5.10 (s, 1H), 3.51-3.52 (m, 1H), 3.05-3.10 (m, 6H), 2.09-2.20 (m, 4H), 1.18-1.35 (m, 3H), 0.59-0.61 (m, 3H).

Example 11

Preparation of Compound 22

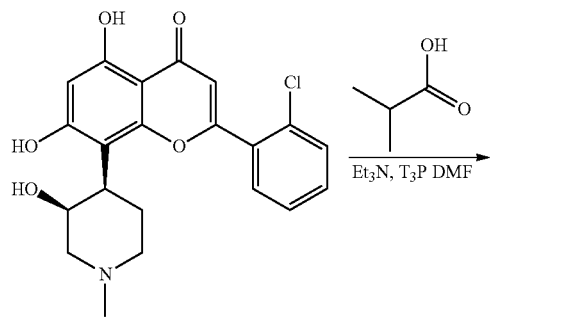

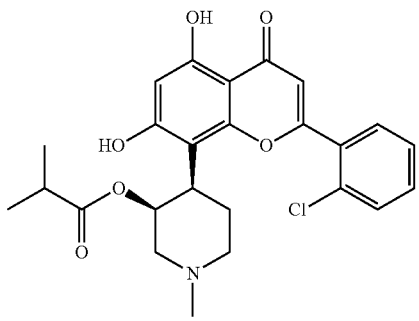

(3S, 4R)-4-(2-(2-chlorophenyl)-5,7-dihydroxy-4-oxo-4H-chromen-8-yl)-1-methylpiperidin-3-yl isobutyrate To a stirred solution of 2-(2-chlorophenyl)-5,7-dihydroxy-8-((3S, 4R)-3-hydroxy-1-methylpiperidin-4-yl)-4H-chromen-4-one (0.3 g, 0.686 mmol, 1 eq) and butyric acid (0.06 g, 0.686 mmol, 1.0 eq) in dimethylformamide (5 mL) at 0° C., Triethylamine (0.32 mL, 2.051 mmol, 3.0 eq) and T$_3$P (0.43 mL, 1.37 mmol, 2.0 eq) were added. The reaction mixture was stirred for 16 hours at room temperature. After confirming the reaction by TLC, the reaction mixture was concentrated. The crude residue obtained was purified by preparative HPLC to afford (3 S, 4R)-4-(2-(2-chlorophenyl)-5,7-dihydroxy-4-oxo-4H-chromen-8-yl)-1-methylpiperidin-3-yl isobutyrate as an off white solid (0.025 g, 11%). LC/MS m/z: 471.1 [M+H]$^+$; HPLC Purity: 98.38; $^1$H NMR (400 MHz, DMSO-d$_6$) δ: 12.96 (s, 1H), 11.07 (s, 1H), 7.60-7.78 (m, 4H), 6.56 (s, 1H), 6.33 (s, 1H), 4.93 (s, 1H), 3.28-3.39 (m, 2H), 2.84-2.91 (m, 3H), 1.71-2.11 (m, 4H), 1.24 (s, 2H), 1.06 (d, J=7.08 Hz, 1H), 0.85 (d, J=6.88 Hz, 3H), 0.76 (d, J=6.92 Hz, 3H).

Example 12

Preparation of Compound 23

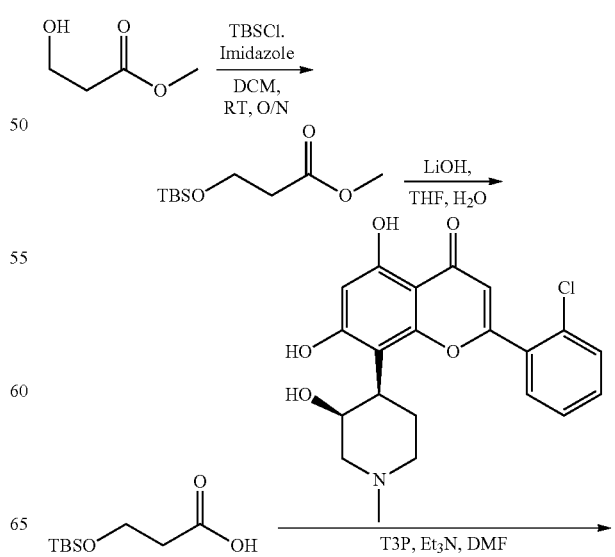

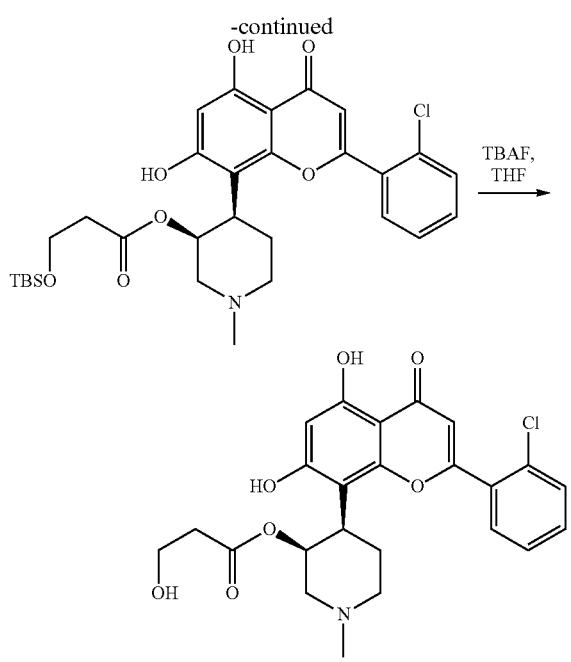

Methyl 3-((tert-butyldimethylsilyl)oxy)propanoate

To a stirred solution of methyl 3-hydroxypropanoate (1 g, 9.6 mmol, 1.0 eq) and imidazole (1.3 g, 19.2 mmol, 2 eq) in dichloromethane (10 mL) at 0° C., tert-Butyldimethylsilyl chloride (2.16 g, 14.42 mmol, 1.5 eq) was added. The reaction mixture was stirred for 20 hours at room temperature. After confirming the reaction by TLC, the solvent was evaporated under vacuum. The crude residue obtained was purified by flash column chromatography to afford methyl 3-((tert-butyldimethylsilyl) oxy) propanoate as a colorless liquid (1.4 g, 58%). $^1$H NMR (400 MHz, DMSO-d$_6$) δ: 3.82 (t, J=8.00 Hz, 2H), 3.59 (s, 3H), 2.47-2.52 (m, 2H), 0.83 (s, 9H), 0.02-0.04 (m, 6H).

3-((tert-butyldimethylsilyl)oxy)propanoic acid

To a stirred solution of methyl 3-((tert-butyldimethylsilyl) oxy)propanoate (1.4 g, 6.86 mmol, 1.0 eq) in tetrahydrofuran (20 mL) and water (7 mL) at 0° C., lithium hydroxide (0.23 g, 10.29 mmol, 1.5 eq) was added. The reaction mixture was stirred for 2 hours at room temperature. After confirming the reaction by TLC, the reaction mixture was quenched with ice cold water (20 mL) and extracted with dichloromethane (20 mL). The organic layer was dried over sodium sulphate the solvent was evaporated under vacuum to afford crude of 3-((tert-butyldimethylsilyl) oxy) propanoic acid as a white solid (0.7 g). $^1$H NMR (400 MHz, DMSO-d$_6$) δ: 12.21 (s, 1H), 3.80 (t, J=6.12 Hz, 2H), 2.37-2.40 (m, 2H), 0.84-0.86 (m, 9H), 0.03-0.04 (m, 6H).

(3S, 4R)-4-(2-(2-chlorophenyl)-5,7-dihydroxy-4-oxo-4H-chromen-8-yl)-1-methylpiperidin-3-yl 3-((tert-butyldimethylsilyl)oxy)propanoate To a stirred solution 2-(2-chlorophenyl)-5,7-dihydroxy-8-((3S, 4R)-3-hydroxy-1-methylpiperidin-4-yl)-4H-chromen-4-one (0.5 g, 1.14 mmol, 1 eq) and 3-((tert-butyldimethylsilyl)oxy)propanoic acid (0.35 g, 1.75 mmol, 1.5 eq) in dimethylformamide (5 mL) at 0° C., Triethylamine (0.48 mL, 3.43 mmol, 3.0 eq) and T3P (0.72 mL, 2.28 mmol, 2.0 eq) were added. The reaction mixture was stirred for 12 hours at room temperature. After confirming the reaction by TLC, the reaction mixture was quenched with ice cold water (50 mL) and extracted with dichloromethane. The organic layer was dried over sodium sulphate and solvent was evaporated under vacuum. The crude residue obtained was purified by flash column chromatography to afford (3 S, 4R)-4-(2-(2-chlorophenyl)-5,7-dihydroxy-4-oxo-4H-chromen-8-yl)-1-methylpiperidin-3-yl 3-((tert-butyldimethylsilyl)oxy)propanoate as a gummy solid (0.06 g, 15%). LC/MS m/z: 588.1 [M+H]$^+$; HPLC Purity: 76.01.

(3S, 4R)-4-(2-(2-chlorophenyl)-5,7-dihydroxy-4-oxo-4H-chromen-8-yl)-1-methylpiperidin-3-yl 3-hydroxypropanoate To a stirred solution of (3 S, 4R)-4-(2-(2-chlorophenyl)-5,7-dihydroxy-4-oxo-4H-chromen-8-yl)-1-methylpiperidin-3-yl 3-((tert-butyldimethylsilyl)oxy)propanoate (0.06 g, 0.102 mmol, 1 eq) in tetrahydrofuran (10 mL) at 0° C., Tetrabutylammonium fluoride (0.5 mL, 2 eq) was added. The reaction mixture was stirred for 16 hours at room temperature. After confirming the reaction by TLC, the reaction mixture was concentrated. The crude residue obtained was purified by preparative HPLC to afford (3 S, 4R)-4-(2-(2-chlorophenyl)-5,7-dihydroxy-4-oxo-4H-chromen-8-yl)-1-methylpiperidin-3-yl 3-hydroxy propanoate as a yellow solid (0.025 g, 50%). LC/MS m/z: 474.1 [M+H]$^+$; HPLC Purity: 96.54%; 1H NMR (400 MHz, DMSO-d$_6$) δ: 13.02 (t, J=Hz, 2H), 7.54-7.77 (m, 4H), 6.08 (s, 1H), 5.56 (s, 1H), 4.81 (s, 1H), 3.33-3.36 (m, 3H), 3.06-3.10 (m, 2H), 2.85-2.90 (m, 3H), 2.15-2.34 (m, 2H), 2.05 (s, 3H), 1.58-1.68 (m, 4H).

Example 13

Preparation of Compound 24

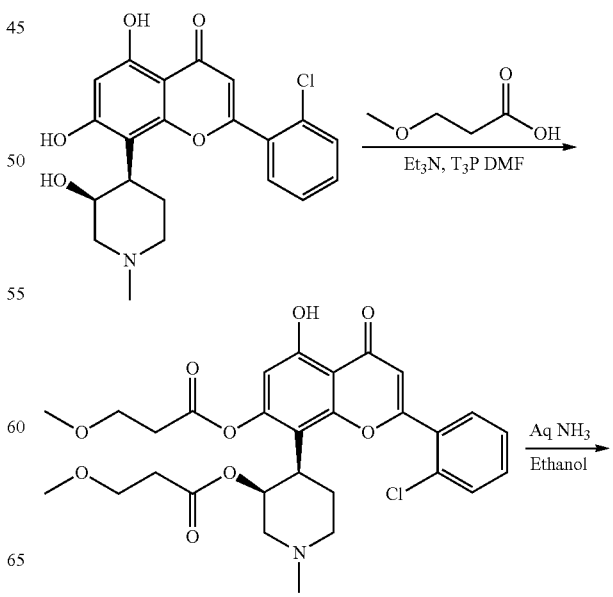

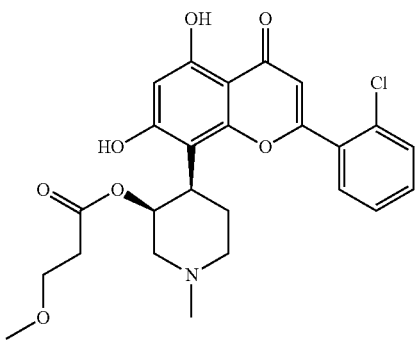

(3S, 4R)-4-(2-(2-chlorophenyl)-5-hydroxy-7-((3-methoxypropanoyl)oxy)-4-oxo-4H-chromen-8-yl)-1-methylpiperidin-3-yl 3-methoxypropanoate To a stirred solution of 2-(2-chlorophenyl)-5,7-dihydroxy-8-((3S, 4R)-3-hydroxy-1-methylpiperidin-4-yl)-4H-chromen-4-one (0.3 g, 0.686 mmol, 1.0 eq) and 3-methoxypropanoic acid (0.07 g, 0.686 mmol, 1.0 eq) in dimethylformamide (5 mL) at 0° C., Triethylamine (0.32 mL, 2.051 mmol, 3.0 eq) and T$_3$P (0.43 mL, 1.37 mmol, 2.0 eq) were added. The reaction mixture was stirred for 12 hours at room temperature. After confirming the reaction by TLC, the reaction mixture was quenched with ice cold water (50 mL) and extracted with dichloromethane. The organic layer was dried over sodium sulphate and solvent was evaporated under vacuum to afford crude of (3 S, 4R)-4-(2-(2-chlorophenyl)-5-hydroxy-7-((3-methoxypropanoyl)oxy)-4-oxo-4H-chromen-8-yl)-1-methylpiperidin-3-yl 3-methoxypropanoate (0.3 g, 70%). LC/MS m/z: 574.2 [M+H]$^+$.

(3S, 4R)-4-(2-(2-chlorophenyl)-5,7-dihydroxy-4-oxo-4H-chromen-8-yl)-1-methylpiperidin-3-yl 3-methoxypropanoate To a stirred solution of (3 S, 4R)-4-(2-(2-chlorophenyl)-5-hydroxy-7-((3-methoxypropanoyl)oxy)-4-oxo-4H-chromen-8-yl)-1-methylpiperidin-3-yl 3-methoxypropanoate (0.3 g, 0.63 mmol, 1 eq) in Ethanol (10 mL) at 0° C., aqueous ammonia (4.5 mL) was added. The reaction mixture was stirred for 2 hours at room temperature. After confirming the reaction by LCMS, the reaction mixture was concentrated. The crude residue obtained was purified by preparative HPLC to afford (3 S, 4R)-4-(2-(2-chlorophenyl)-5,7-dihydroxy-4-oxo-4H-chromen-8-yl)-1-methylpiperidin-3-yl 3-methoxypropanoate as a yellow solid (0.05 g, 20%). LC/MS m/z: 488.2 [M+H]$^+$; HPLC Purity: 93.95%; $^1$H NMR (400 MHz, DMSO-d$_6$) δ: 12.99 (s, 1H), 11.06 (s, 1H), 7.58-7.79 (m, 4H), 6.56 (s, 1H), 6.33 (s, 1H), 4.96 (s, 1H), 3.29-3.30 (m, 2H), 3.02 (s, 3H), 2.83-2.86 (m, 4H), 2.26-2.33 (m, 1H), 2.11-2.21 (m, 6H), 1.91-1.94 (m, 1H), 1.65 (d, J=11.56 Hz, 1H).

Example 14

Preparation of Compound 25

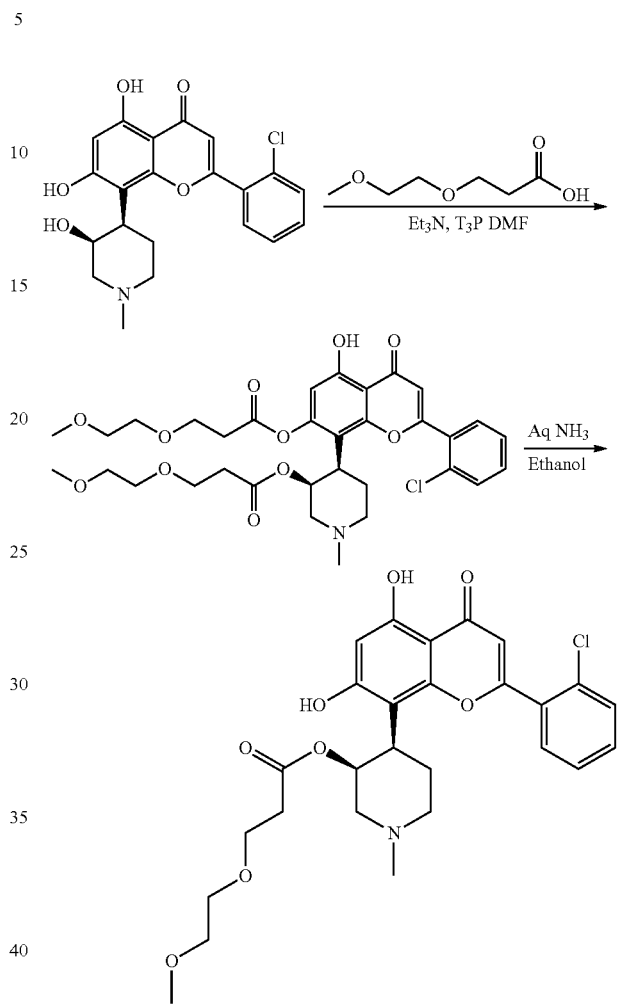

(3S, 4R)-4-(2-(2-chlorophenyl)-5-hydroxy-7-((3-(2-methoxyethoxy)propanoyl)oxy)-4-oxo-4H-chromen-8-yl)-1-methylpiperidin-3-yl 3-(2-methoxyethoxy) propanoate To a stirred solution of 2-(2-chlorophenyl)-5,7-dihydroxy-8-((3S, 4R)-3-hydroxy-1-methylpiperidin-4-yl)-4H-chromen-4-one (0.3 g, 0.686 mmol, 1 eq) and 3-(2-methoxyethoxy)propanoic acid (0.074 g, 0.686 mmol, 1.0 eq) in dimethylformamide (5 mL) at 0° C., Triethylamine (0.28 mL, 2.051 mmol, 3.0 eq) and T$_3$P (0.43 mL, 1.37 mmol, 2.0 eq) were added. The reaction mixture was stirred for 12 hours at room temperature. After confirming the reaction by TLC, the reaction mixture was quenched with ice cold water (50 mL) and extracted with dichloromethane. The organic layer was dried over sodium sulphate and solvent was evaporated under vacuum to afford crude of (3 S, 4R)-4-(2-(2-chlorophenyl)-5-hydroxy-7-((3-(2-methoxyethoxy)propanoyl)oxy)-4-oxo-4H-chromen-8-yl)-1-methylpiperidin-3-yl 3-(2-methoxyethoxy) propanoate (0.3 g, 70%). LC/MS m/z: 662.3 [M+H]$^+$.

81

(3S, 4R)-4-(2-(2-chlorophenyl)-5,7-dihydroxy-4-oxo-4H-chromen-8-yl)-1-methylpiperidin-3-yl 3-(2-methoxyethoxy)propanoate To a stirred solution of (3 S, 4R)-4-(2-(2-chlorophenyl)-5-hydroxy-7-((3-methoxypropanoyl)oxy)-4-oxo-4H-chromen-8-yl)-1-methylpiperidin-3-yl 3-methoxypropanoate (0.3 g, 0.63 mmol, 1 eq) in Ethanol (10 mL) at 0° C., aqueous ammonia (4.5 mL) was added. The reaction mixture was stirred for 2 hours at room temperature. After confirming the reaction by LC/MS, the reaction mixture was concentrated. The crude residue obtained was purified by preparative HPLC to afford (3 S, 4R)-4-(2-(2-chlorophenyl)-5,7-dihydroxy-4-oxo-4H-chromen-8-yl)-1-methylpiperidin-3-yl 3-(2-methoxyethoxy) propanoate as a yellow solid (0.12 g, 33%.). LC/MS m/z: 532.2 [M+H]+; HPLC Purity: 98.52%; $^1$H NMR (400 MHz, DMSO-$d_6$) δ: 12.97 (s, 1H), 11.07 (s, 1H), 7.60-7.81 (m, 4H), 6.56 (s, 1H), 6.34 (s, 1H), 4.96 (s, 1H), 3.25-3.38 (m, 6H), 3.18 (s, 3H), 2.85-2.89 (m, 3H), 2.29 (s, 2H), 2.17-2.21 (m, 5H), 2.12 (s, 2H).

Example 15

Preparation of Compound 26

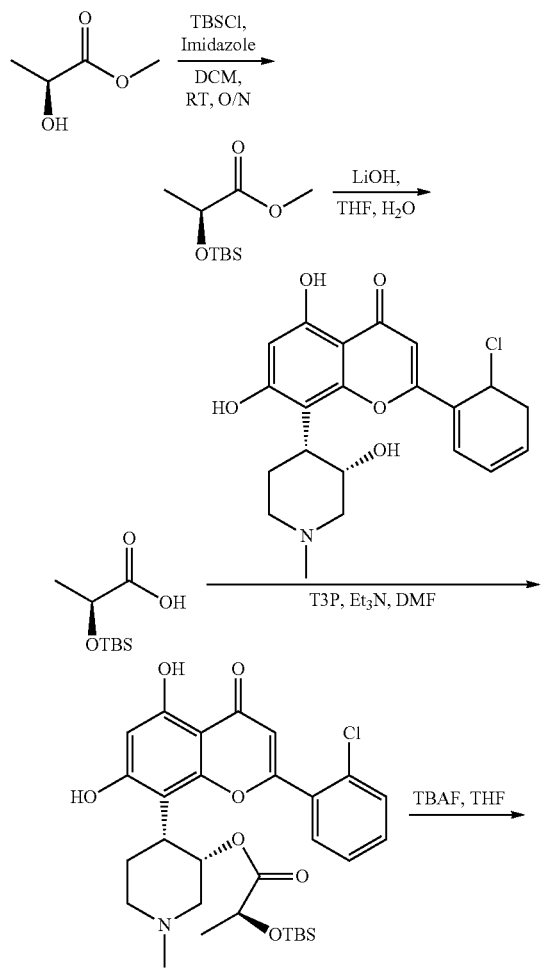

82

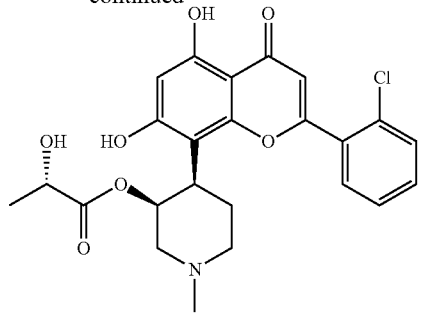

Methyl (S)-2-((tert-butyldimethylsilyl)oxy)propanoate

To a stirred solution of methyl (S)-2-hydroxypropanoate (0.3 g, 2.88 mmol, 1.0 eq) and imidazole (0.39 g, 5.76 mmol, 2 eq) in dichloromethane (10 mL) at 0° C., tert-Butyldimethylsilyl chloride (0.65 g, 4.32 mmol, 1.5 eq) was added. The reaction mixture was stirred for 20 hours at room temperature. After confirming the reaction by TLC, the solvent was evaporated under vacuum. The crude residue obtained was purified by flash column chromatography to afford methyl (S)-2-((tert-butyldimethylsilyl) oxy)propanoate as a colorless liquid (0.6 g, 78%). $^1$H NMR (400 MHz, DMSO-$d_6$) δ: 4.37 (d, J=8.80 Hz, 1H), 3.64 (s, 3H), 1.28-1.30 (m, 3H), 0.86-0.93 (m, 9H), 0.05-0.05 (m, 6H).

(S)-2-((tert-butyldimethylsilyl)oxy)propanoic acid

To a stirred solution of methyl (S)-2-((tert-butyldimethylsilyl)oxy)propanoate (0.6 g, 2.94 mmol, 1.0 eq) in tetrahydrofuran (10 mL) and water (3 mL) at 0° C., lithium hydroxide (0.1 g, 4.41 mmol, 1.5 eq) was added. The reaction mixture was stirred for 2 hours at room temperature. After confirming the reaction by TLC, the reaction mixture was quenched with ice cold water (20 mL) and extracted with dichloromethane (20 mL). The organic layer was dried over sodium sulphate the solvent was evaporated under vacuum to afford crude of (S)-2-((tert-butyldimethylsilyl) oxy)propanoic acid as a white solid (0.43 g, 76%). $^1$H NMR (400 MHz, DMSO-$d_6$) δ: 12.12 (s, 1H), 4.36 (d, J=8.70 Hz, 1H), 1.26-1.34 (m, 3H), 0.85-0.92 (m, 9H), 0.05-0.05 (m, 6H).

(3S, 4R)-4-(2-(2-chlorophenyl)-5,7-dihydroxy-4-oxo-4H-chromen-8-yl)-1-methylpiperidin-3-yl (S)-2-((tert-butyldimethylsilyl)oxy)propanoate To a stirred solution 2-(2-chlorophenyl)-5,7-dihydroxy-8-((3S, 4R)-3-hydroxy-1-methylpiperidin-4-yl)-4H-chromen-4-one (0.7 g, 1.60 mmol, 1 eq) and (S)-2-((tert-butyldimethylsilyl)oxy)propanoic acid (0.4 g, 1.92 mmol, 1.2 eq) in dimethylformamide (5 mL) at 0° C., Triethylamine (0.67 mL, 4.8 mmol, 3.0 eq) and T$_3$P (0.9 mL, 3.2 mmol, 2.0 eq) were added. The reaction mixture was stirred for 12 hours at room temperature. After confirming the reaction by TLC, the reaction mixture was quenched with ice cold water (30 mL) and extracted with dichloromethane. The organic layer was dried over sodium sulphate and solvent was evaporated under vacuum. The crude residue obtained was purified by flash column chromatography to afford (3 S, 4R)-4-(2-(2-chlorophenyl)-5,7-dihydroxy-4-oxo-4H-chromen-8-yl)-1- methylpiperidin-3-yl(S)-2-((tertbutyldimethylsilyl) oxy) propanoate as a gummy solid (0.06 g, 15%). LC/MS m/z: 588.3 [M+H]⁺.

(3S, 4R)-4-(2-(2-chlorophenyl)-5,7-dihydroxy-4-oxo-4H-chromen-8-yl)-1-methylpiperidin-3-yl (S)-2-hydroxypropanoate To a stirred solution of (3 S, 4R)-4-(2-(2-chlorophenyl)-5,7-dihydroxy-4-oxo-4H-chromen-8-yl)-1-methylpiperidin-3-yl(S)-2-((tert-butyldimethylsilyl) oxy)propanoate (0.06 g, 0.102 mmol, 1 eq) in tetrahydrofuran (10 mL) at 0° C., tetrabutylammonium fluoride (0.5 mL, 2 eq) was added. The reaction mixture was stirred for 16 hours at room temperature. After confirming the reaction by TLC, the reaction mixture was concentrated. The crude residue obtained was purified by preparative HPLC to afford (3S, 4R)-4-(2-(2-chlorophenyl)-5,7-dihydroxy-4-oxo-4H-chromen-8-yl)-1-methylpiperidin-3-yl (S)-2-hydroxypropanoate as a yellow solid (0.025 g, 50%). LC/MS m/z: 474.0 [M+H]⁺; HPLC Purity: 92.38%; ¹H NMR (400 MHz, DMSO-d₆) δ: 12.90 (s, 1H), 11.43 (s, 1H), 7.53-7.75 (m, 4H), 6.04 (s, 1H), 5.41 (s, 1H), 3.79-3.81 (m, 1H), 3.15-3.19 (m, 6H), 2.80 (d, J=11.76 Hz, 3H), 2.07 (d, J=13.72 Hz, 4H), 1.86 (s, 2H).

Example 16

Preparation of Compound 27

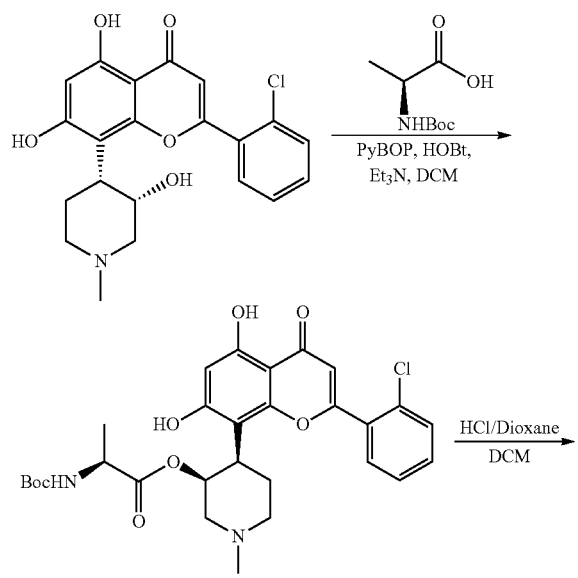

(3S, 4R)-4-(2-(2-chlorophenyl)-5,7-dihydroxy-4-oxo-4H-chromen-8-yl)-1-methylpiperidin-3-yl (tert-butoxycarbonyl)-L-alaninate To a stirred solution of 2-(2-chlorophenyl)-5,7-dihydroxy-8-((3S, 4R)-3-hydroxy-1-methylpiperidin-4-yl)-4H-chromen-4-one (0.3 g, 0.686 mmol, 1 eq) in dichloromethane (5 mL) at 0° C., Triethylamine (0.28 mL, 2.051 mmol, 3.0 eq) and (tert-butoxycarbonyl)-L-alanine (0.41 g, 0.75 mmol, 1.1 eq) were added followed by HOBT (0.12 g, 0.89 mmol, 1.3 eq) and PyBOP (0.57 g, 0.82 mmol, 1.2 eq). The reaction mixture was stirred for 12 hours at room temperature. After confirming the reaction by TLC, the reaction mixture was quenched with ice cold water (50 mL) and extracted with dichloromethane, washed with water and brine solution. The organic layer was dried over sodium sulphate and solvent was evaporated under vacuum to afford crude of (3 S, 4R)-4-(2-(2-chlorophenyl)-5,7-dihydroxy-4-oxo-4H-chromen-8-yl)-1-methylpiperidin-3-yl (tert-butoxycarbonyl)-L-alaninate (0.2 g, 52%). LC/MS m/z: 573.2 [M+H]⁺.

(3S, 4R)-4-(2-(2-chlorophenyl)-5,7-dihydroxy-4-oxo-4H-chromen-8-yl)-1-methylpiperidin-3-yl L-alaninate To a stirred solution of (3 S, 4R)-4-(2-(2-chlorophenyl)-5,7-dihydroxy-4-oxo-4H-chromen-8-yl)-1-methylpiperidin-3-yl (tert-butoxycarbonyl)-L-alaninate (0.2 g, 0.34 mmol, 1 eq) in dichloromethane (6 mL) at 0° C., 2.0 M HCl in dioxane (2.5 mL) was added. The reaction mixture was stirred for 2 hours at room temperature. After confirming the reaction by LCMS, the reaction mixture was concentrated. The crude residue obtained was purified by preparative HPLC to afford TFA salt of (3 S, 4R)-4-(2-(2-chlorophenyl)-5,7-dihydroxy-4-oxo-4H-chromen-8-yl)-1-methylpiperidin-3-yl L-alaninate as a off white solid (0.05 g, 30%). LC/MS m/z: 473.1 [M+H]⁺; HPLC Purity: 97.61%; ¹H NMR (400 MHz, DMSO-d₆) δ: 12.98 (s, 1H), 11.55 (s, 1H), 9.76 (s, 1H), 8.30 (s, 3H), 7.56-7.79 (m, 4H), 6.60 (s, 1H), 6.38 (s, 1H), 5.33 (s, 1H), 3.66 (d, J=12.40 Hz, 2H), 3.52 (s, 2H), 3.07-3.23 (m, 2H), 2.80 (s, 3H), 1.99 (d, J=13.60 Hz, 1H), 1.35 (d, J=7.20 Hz, 3H).

Example 17

Preparation of Compound 28

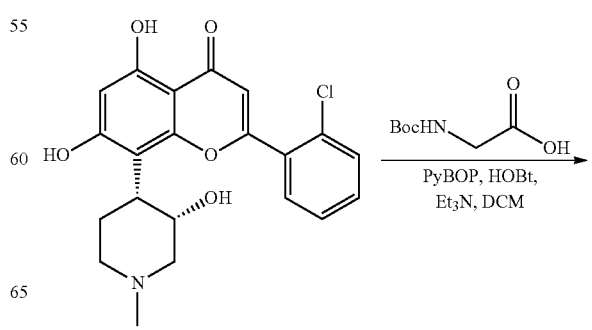

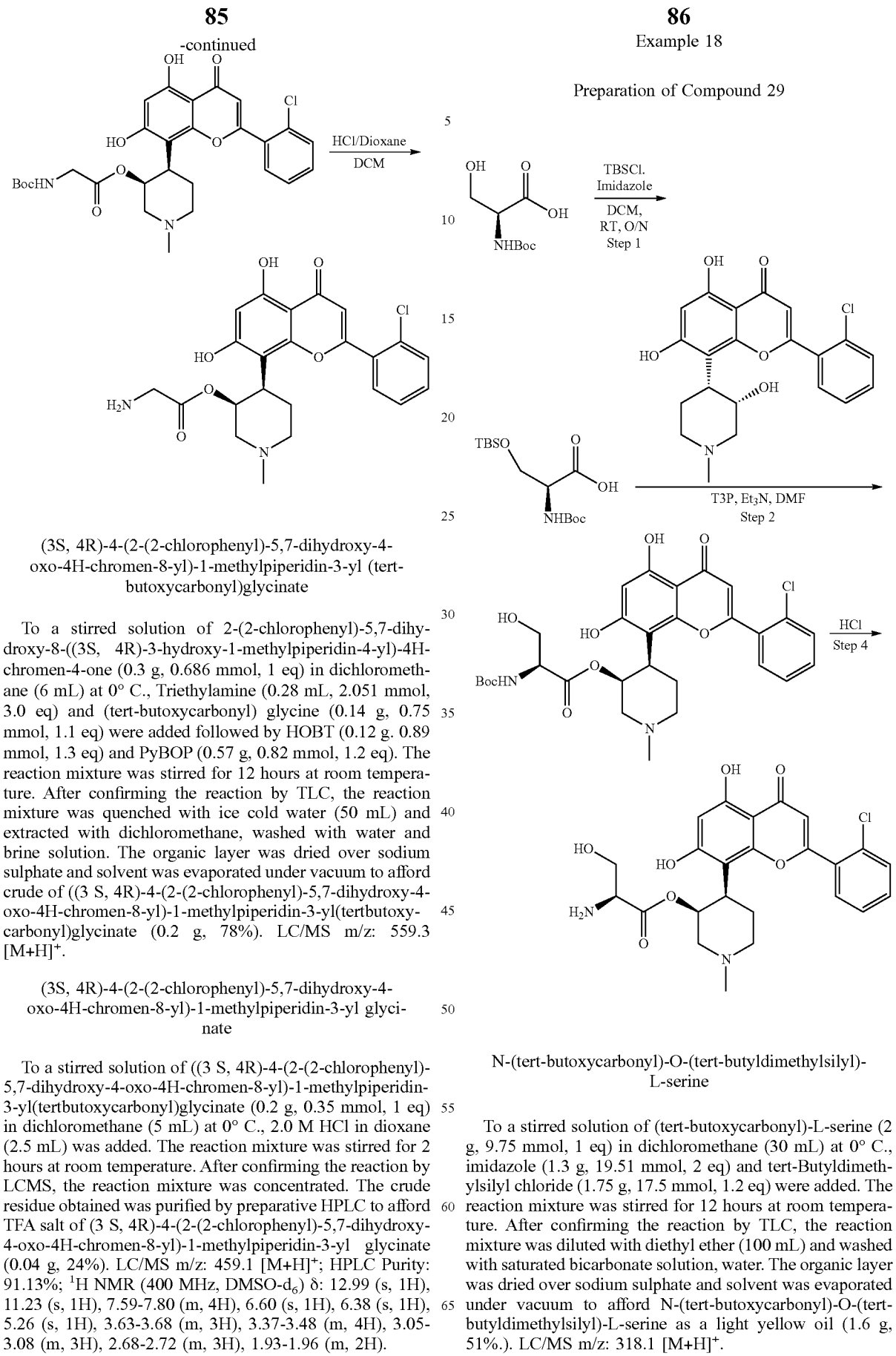

(3S, 4R)-4-(2-(2-chlorophenyl)-5,7-dihydroxy-4-oxo-4H-chromen-8-yl)-1-methylpiperidin-3-yl (tert-butoxycarbonyl)glycinate To a stirred solution of 2-(2-chlorophenyl)-5,7-dihydroxy-8-((3S, 4R)-3-hydroxy-1-methylpiperidin-4-yl)-4H-chromen-4-one (0.3 g, 0.686 mmol, 1 eq) in dichloromethane (6 mL) at 0° C., Triethylamine (0.28 mL, 2.051 mmol, 3.0 eq) and (tert-butoxycarbonyl) glycine (0.14 g, 0.75 mmol, 1.1 eq) were added followed by HOBT (0.12 g. 0.89 mmol, 1.3 eq) and PyBOP (0.57 g, 0.82 mmol, 1.2 eq). The reaction mixture was stirred for 12 hours at room temperature. After confirming the reaction by TLC, the reaction mixture was quenched with ice cold water (50 mL) and extracted with dichloromethane, washed with water and brine solution. The organic layer was dried over sodium sulphate and solvent was evaporated under vacuum to afford crude of ((3 S, 4R)-4-(2-(2-chlorophenyl)-5,7-dihydroxy-4-oxo-4H-chromen-8-yl)-1-methylpiperidin-3-yl(tertbutoxycarbonyl)glycinate (0.2 g, 78%). LC/MS m/z: 559.3 [M+H]$^+$.

(3S, 4R)-4-(2-(2-chlorophenyl)-5,7-dihydroxy-4-oxo-4H-chromen-8-yl)-1-methylpiperidin-3-yl glycinate To a stirred solution of ((3 S, 4R)-4-(2-(2-chlorophenyl)-5,7-dihydroxy-4-oxo-4H-chromen-8-yl)-1-methylpiperidin-3-yl(tertbutoxycarbonyl)glycinate (0.2 g, 0.35 mmol, 1 eq) in dichloromethane (5 mL) at 0° C., 2.0 M HCl in dioxane (2.5 mL) was added. The reaction mixture was stirred for 2 hours at room temperature. After confirming the reaction by LCMS, the reaction mixture was concentrated. The crude residue obtained was purified by preparative HPLC to afford TFA salt of (3 S, 4R)-4-(2-(2-chlorophenyl)-5,7-dihydroxy-4-oxo-4H-chromen-8-yl)-1-methylpiperidin-3-yl glycinate (0.04 g, 24%). LC/MS m/z: 459.1 [M+H]$^+$; HPLC Purity: 91.13%; $^1$H NMR (400 MHz, DMSO-$d_6$) δ: 12.99 (s, 1H), 11.23 (s, 1H), 7.59-7.80 (m, 4H), 6.60 (s, 1H), 6.38 (s, 1H), 5.26 (s, 1H), 3.63-3.68 (m, 3H), 3.37-3.48 (m, 4H), 3.05-3.08 (m, 3H), 2.68-2.72 (m, 3H), 1.93-1.96 (m, 2H).

Example 18

Preparation of Compound 29

N-(tert-butoxycarbonyl)-O-(tert-butyldimethylsilyl)-L-serine

To a stirred solution of (tert-butoxycarbonyl)-L-serine (2 g, 9.75 mmol, 1 eq) in dichloromethane (30 mL) at 0° C., imidazole (1.3 g, 19.51 mmol, 2 eq) and tert-Butyldimethylsilyl chloride (1.75 g, 17.5 mmol, 1.2 eq) were added. The reaction mixture was stirred for 12 hours at room temperature. After confirming the reaction by TLC, the reaction mixture was diluted with diethyl ether (100 mL) and washed with saturated bicarbonate solution, water. The organic layer was dried over sodium sulphate and solvent was evaporated under vacuum to afford N-(tert-butoxycarbonyl)-O-(tert-butyldimethylsilyl)-L-serine as a light yellow oil (1.6 g, 51%.). LC/MS m/z: 318.1 [M+H]$^+$.

(3S, 4R)-4-(2-(2-chlorophenyl)-5,7-dihydroxy-4-oxo-4H-chromen-8-yl)-1-methylpiperidin-3-yl N-(tert-butoxycarbonyl)-O-(tert-butyldimethylsilyl)-L-serinate To a stirred solution of N-(tert-butoxycarbonyl)-O-(tert-butyldimethylsilyl)-L-serine (0.7 g, 2.19 mmol, 1 eq) and 2-(2-chlorophenyl)-5,7-dihydroxy-8-((3 S, 4R)-3-hydroxy-1-methylpiperidin-4-yl)-4H-chromen-4-one (0.76 g, 19.51 mmol, 2 eq) in dimethylformamide (10 mL) at 0° C., Triethylamine (0.78 mL, 5.2 mmol, 3 eq) and T3P (1.1 mL, 3.4 mmol, 2 eq) were added. The reaction mixture was stirred for 16 hours at room temperature. After confirming the reaction by TLC, the reaction mixture was quenched with ice cold water (50 mL) and extracted with dichloromethane. The organic layer was washed with 10% NaHCO$_3$ solution (50 mL), water (50 mL) and brine solution (50 mL). The organic layer was dried over sodium sulphate and solvent was evaporated under vacuum. The crude residue obtained was purified by preparative HPLC to afford 3S,4R)-4-(2-(2-chlorophenyl)-5,7-dihydroxy-4-oxo-4H-chromen-8-yl)-1-methylpiperidin-3-yl N-(tert-butoxycarbonyl)-O-(tert-butyldimethylsilyl)-L-serinate as a light yellow solid (0.29 g, 22%). LC/MS m/z: 589.2 (Cleavage of silyl group mass) [M+H]$^+$.

(3S, 4R)-4-(2-(2-chlorophenyl)-5,7-dihydroxy-4-oxo-4H-chromen-8-yl)-1-methylpiperidin-3-yl L-serinate To a stirred solution of 3 S, 4R)-4-(2-(2-chlorophenyl)-5,7-dihydroxy-4-oxo-4H-chromen-8-yl)-1-methylpiperidin-3-yl N-(tert-butoxycarbonyl)-O-(tert-butyldimethylsilyl)-L-serinate (0.29 g, 0.49 mmol, 1 eq) in dichloromethane (10 mL) at 0° C., 2.0 M HCl in dioxane (0.49 mL, 2 eq) was added. The reaction mixture was stirred for 16 hours at room temperature. After confirming the reaction by LCMS, the reaction mixture was concentrated. The crude residue obtained was purified by preparative HPLC to afford TFA salt of (3 S, 4R)-4-(2-(2-chlorophenyl)-5,7-dihydroxy-4-oxo-4H-chromen-8-yl)-1-methylpiperidin-3-yl L-serinate (0.12 g, 50%). LC/MS m/z: 489.2 [M+H]$^+$; HPLC Purity: 98.40%; $^1$H NMR (400 MHz, DMSO-d$_6$) δ: 12.97 (s, 1H), 11.55 (s, 1H), 9.58 (s, 1H), 8.34 (s, 3H), 7.65-7.77 (m, 4H), 6.58 (s, 1H), 6.37 (s, 1H), 5.38 (s, 2H), 3.97 (d, J=8.32, Hz, 2H), 3.49-3.67 (m, 5H), 3.07-3.21 (m, 2H), 2.81 (s, 1H), 1.97 (d, J=13.60, Hz, 1H).

Example 19

Preparation of Compound 30

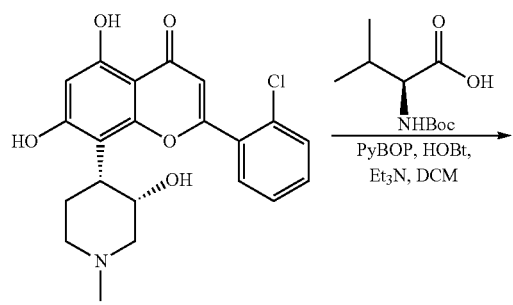

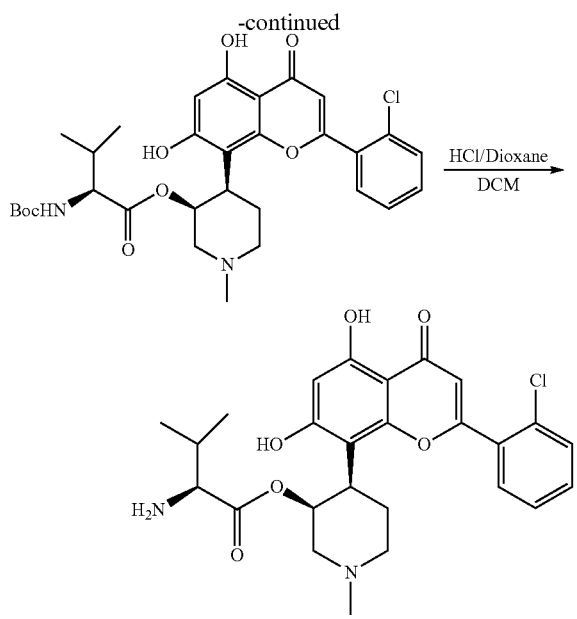

(3S, 4R)-4-(2-(2-chlorophenyl)-5,7-dihydroxy-4-oxo-4H-chromen-8-yl)-1-methylpiperidin-3-yl (tert-butoxycarbonyl)-L-valinate To a stirred solution of 2-(2-chlorophenyl)-5,7-dihydroxy-8-((3S, 4R)-3-hydroxy-1-methylpiperidin-4-yl)-4H-chromen-4-one (0.3 g, 0.686 mmol, 1 eq) in dichloromethane (6 mL) at 0° C., Triethylamine (0.28 mL, 2.051 mmol, 3.0 eq) and (Tert-butoxycarbonyl)-L-valine (0.16 g, 0.75 mmol, 1.1 eq) were added followed by HOBT (0.12 g. 0.89 mmol, 1.3 eq) and PyBOP (0.57 g, 0.82 mmol, 1.2 eq). The reaction mixture was stirred for 12 hours at room temperature. After confirming the reaction by TLC, the reaction mixture was quenched with ice cold water (50 mL) and extracted with dichloromethane, washed with water and brine solution. The organic layer was dried over sodium sulphate and solvent was evaporated under vacuum to afford crude of (3 S, 4R)-4-(2-(2-chlorophenyl)-5,7-dihydroxy-4-oxo-4H-chromen-8-yl)-1-methylpiperidin-3-yl (tert-butoxycarbonyl)-L-valinate (0.2 g, 72%). LC/MS m/z: 602.1 [M+H]$^+$.

(3S, 4R)-4-(2-(2-chlorophenyl)-5,7-dihydroxy-4-oxo-4H-chromen-8-yl)-1-methylpiperidin-3-yl L-valinate To a stirred solution of (3 S, 4R)-4-(2-(2-chlorophenyl)-5,7-dihydroxy-4-oxo-4H-chromen-8-yl)-1-methylpiperidin-3-yl (tert-butoxycarbonyl)-L-valinate (0.2 g, 0.35 mmol, 1 eq) in dichloromethane (5 mL) at 0° C., 2.0 M HCl in dioxane (2.5 mL) was added. The reaction mixture was stirred for 2 hours at room temperature. After confirming the reaction by LCMS, the reaction mixture was concentrated. The crude residue obtained was purified by preparative HPLC to afford (3 S, 4R)-4-(2-(2-chlorophenyl)-5, 7-dihydroxy-4-oxo-4H-chromen-8-yl)-1-methylpiperidin-3-yl L-valinate (0.03 g, 18%). LC/MS m/z: 501.1 [M+H]$^+$; HPLC Purity: 96.51; $^1$H NMR (400 MHz, DMSO-d$_6$) δ: 12.99 (s, 1H), 11.48 (s, 1H), 9.58 (s, 1H), 8.25 (s, 2H), 7.56-7.79 (m, 4H), 6.61 (s, 1H), 6.37 (s, 1H), 5.48 (s, 1H), 3.63-3.67 (m, 3H), 2.99-3.39 (m, 6H), 1.94-2.07 (m, 2H), 0.82 (d, J=6.00 Hz, 6H).

Example 20

Preparation of Compound 31

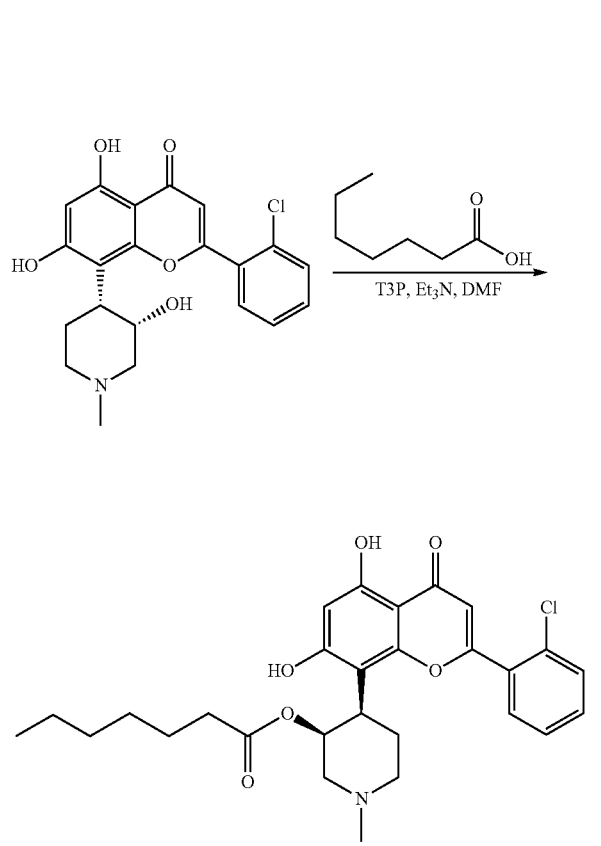

(3S, 4R)-4-(2-(2-chlorophenyl)-5,7-dihydroxy-4-oxo-4H-chromen-8-yl)-1-methylpiperidin-3-yl heptanoate To a stirred solution of 2-(2-chlorophenyl)-5,7-dihydroxy-8-((3S, 4R)-3-hydroxy-1-methylpiperidin-4-yl)-4H-chromen-4-one (0.3 g, 0.686 mmol, 1 eq) and heptanoic acid (0.089 g, 0.686 mmol, 1.0 eq) in dimethylformamide (5 mL) at 0° C., Triethylamine (0.32 mL, 2.05 mmol, 3.0 eq) and T$_3$P (0.43 mL, 1.37 mmol, 2.0 eq) were added. The reaction mixture was stirred for 16 hours at room temperature. After confirming the reaction by TLC, the reaction mixture was concentrated. The crude residue obtained was purified by preparative HPLC to afford (3 S, 4R)-4-(2-(2-chlorophenyl)-5,7-dihydroxy-4-oxo-4H-chromen-8-yl)-1-methylpiperidin-3-yl heptanoate as a off white solid (0.024 g, 11%). LC/MS m/z: 514.2 [M+H]$^+$; HPLC Purity: 98.23%; $^1$H NMR (400 MHz, DMSO-d$_6$) δ: 2.97 (s, 1H), 11.13 (s, 1H), 7.57-7.79 (m, 4H), 6.56 (s, 1H), 6.33 (s, 1H), 4.95 (s, 1H), 3.28-3.32 (m, 1H), 2.87-3.27 (m, 3H), 2.51 (d, J=12.00 Hz, 1H), 2.33 (s, 3H), 2.15-2.25 (m, 3H), 1.92 (d, J=16.00 Hz, 1H), 1.62 (s, 1H), 1.31-1.42 (m, 3H), 1.10-1.22 (m, 4H), 0.83-1.04 (m, 4H).

Example 21

Preparation of Compound 32

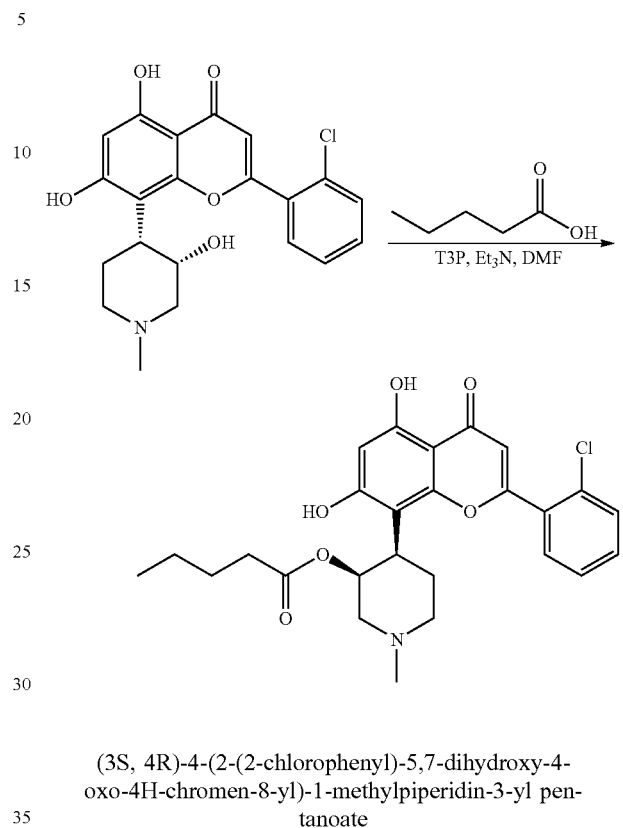

(3S, 4R)-4-(2-(2-chlorophenyl)-5,7-dihydroxy-4-oxo-4H-chromen-8-yl)-1-methylpiperidin-3-yl pentanoate To a stirred solution of 2-(2-chlorophenyl)-5,7-dihydroxy-8-((3S, 4R)-3-hydroxy-1-methylpiperidin-4-yl)-4H-chromen-4-one (0.3 g, 0.686 mmol, 1 eq) and Valeric acid (0.08 g, 0.686 mmol, 1.0 eq) in dimethylformamide (5 mL) at 0° C., Triethylamine (0.32 mL, 2.05 mmol, 3.0 eq) and T$_3$P (0.43 mL, 1.37 mmol, 2.0 eq) were added. The reaction mixture was stirred for 16 hours at room temperature. After confirming the reaction by TLC, the reaction mixture was concentrated. The crude residue obtained was purified by preparative HPLC to afford (3 S, 4R)-4-(2-(2-chlorophenyl)-5,7-dihydroxy-4-oxo-4H-chromen-8-yl)-1-methylpiperidin-3-yl pentanoate as an off white solid (0.024 g, 11%). LC/MS m/z: 486.2 [M+H]$^+$; HPLC Purity: 96.85%; $^1$H NMR (400 MHz, DMSO-d$_6$) δ: 2.96 (s, 1H), 11.13 (s, 1H), 7.57-7.79 (m, 4H), 6.56 (s, 1H), 6.32 (s, 1H), 4.95 (s, 1H), 2.84 (d, J=13.60 Hz, 3H), 2.12-2.20 (m, 5H), 1.90-1.96 (m, 3H), 1.60-1.70 (m, 1H), 1.45-1.48 (m, 1H), 1.19-1.28 (m, 3H), 0.96 (d, J=2.60 Hz, 2H), 0.84-0.94 (m, 1H).

Example 22

Preparation of Compound 33

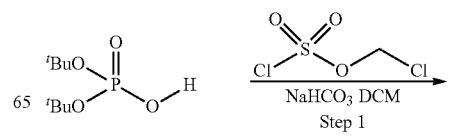

Step 1

-continued

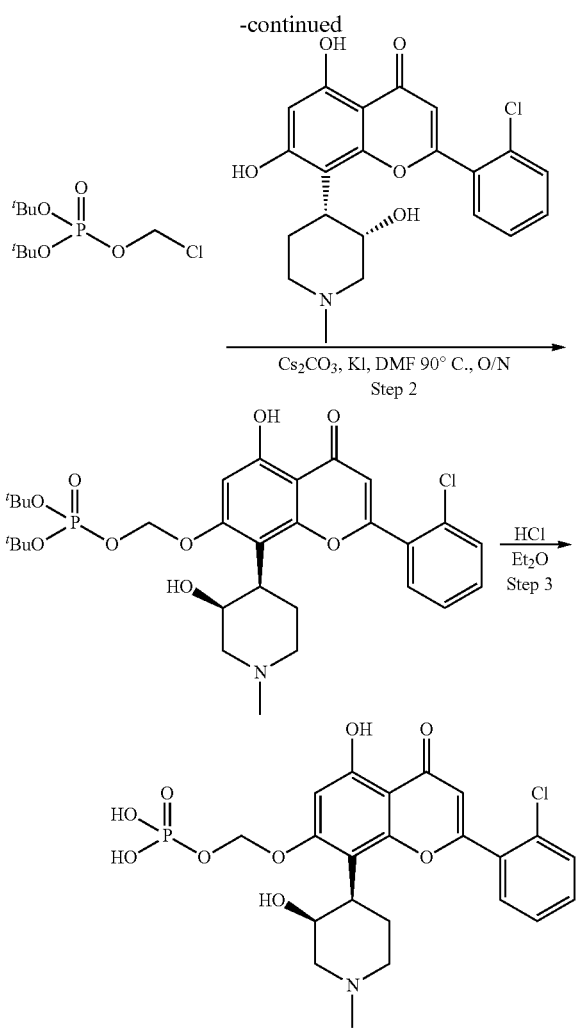

Di-tert-butyl (chloromethyl) phosphate

To a stirred solution of di-tert-butyl hydrogen phosphate (1 g, 4.75 mmol, 1 eq), sodium bicarbonate (15.9 g, 19.04 mmol, 4 eq) and Tetrabutylammonium hydrogensulfate (0.16 g, 0.47 mmol, 0.1 eq) in dichloromethane (30 mL) at 0° C., chloromethyl chlorosulphate (0.57 mL, 5.71 mmol, 1.2 eq) (in dichloromethane 15 mL) was added drop wise. The reaction mixture was stirred for 16 hours at room temperature. After confirming the reaction by TLC, The reaction mixture was diluted with dichloromethane (10 mL) and washed with saturated bicarbonate solution, water. The organic layer was dried over sodium sulphate and solvent was evaporated under vacuum to afford di-tert-butyl (chloromethyl) phosphate as a light yellow oil (0.6 g, 51%). $^1$H NMR (400 MHz, CDCl$_3$) δ: 5.65 (dd, J=14.80, Hz, 2H), 1.47-1.53 (m, 18H).

Di-tert-butyl (((2-(2-chlorophenyl)-5-hydroxy-8-((3S, 4R)-3-hydroxy-1-methylpiperidin-4-yl)-4-oxo-4H-chromen-7-yl)oxy)methyl) phosphate To a stirred solution of 2-(2-chlorophenyl)-5,7-dihydroxy-8-((3S,4R)-3-hydroxy-1-methylpiperidin-4-yl)-4H-chromen-4-one (0.48 g, 1.09 mmol, 1 eq), Cesium carbonate (1.0 g, 3.29 mmol, 3 eq) and potassium iodide (0.218 g, 1.31 mmol, 1.2 eq) in dimethylformamide (10 mL) at 0° C., di-tert-butyl (chloromethyl) phosphate (0.34 g, 1.31 mmol, 1.2 eq) was added. The reaction mixture was stirred for 16 hours at 90° C. After confirming the reaction by TLC, the reaction mixture was filtered through celite and the filtrate was evaporated under high vacuum. The crude residue obtained was purified by preparative HPLC to afford di-tert-butyl (((2-(2-chlorophenyl)-5-hydroxy-8-((3 S, 4R)-3-hydroxy-1-methylpiperidin-4-yl)-4-oxo-4H-chromen-7-yl) oxy) methyl) phosphate as a light yellow solid (0.25 g, 38%). LC/MS m/z: 568.2 (t-butyl cleavage mass) [M+H]$^+$.

((2-(2-chlorophenyl)-5-hydroxy-8-((3S, 4R)-3-hydroxy-1-methylpiperidin-4-yl)-4-oxo-4H-chromen-7-yl) oxy) methyl dihydrogen phosphate To a stirred solution of di-tert-butyl (((2-(2-chlorophenyl)-5-hydroxy-8-((3 S, 4R)-3-hydroxy-1-methylpiperidin-4-yl)-4-oxo-4H-chromen-7-yl)oxy) methyl) phosphate (0.25 g, 0.401 mmol, 1 eq) in dichloromethane (10 mL) at 0° C., 2.0 M HCl in dioxane (0.49 mL, 2 eq) was added. The reaction mixture was stirred for 4 hours at room temperature. After confirming the reaction by LCMS, the reaction mixture was concentrated. The crude residue obtained was purified by preparative HPLC to afford TFA salt of ((2-(2-chlorophenyl)-5-hydroxy-8-((3 S, 4R)-3-hydroxy-1-methylpiperidin-4-yl)-4-oxo-4H-chromen-7-yl) oxy) methyl dihydrogen phosphate as a yellow solid (0.12 g, 58%). LC/MS m/z: 512.0 [M+H]$^+$; HPLC Purity: 97.21%; $^1$H NMR (400 MHz, DMSO-d$_6$) δ: 12.95 (s, 1H), 8.02 (d, J=7.68 Hz, 1H), 7.53-7.74 (m, 3H), 6.64 (s, 1H), 6.38 (s, 1H), 5.49 (t, J=8.36 Hz, 1H), 5.05 (t, J=7.56 Hz, 1H), 4.08 (s, 1H), 3.88 (d, J=13.44 Hz, 1H), 3.44-3.66 (m, 4H), 2.98 (s, 4H), 1.71 (d, J=13.68 Hz, 1H).

Example 23

Preparation of Compound 34

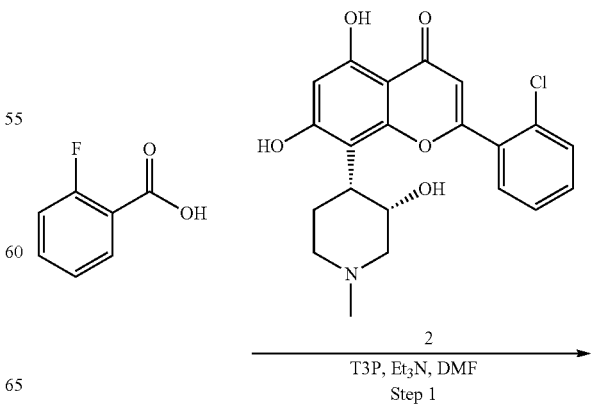

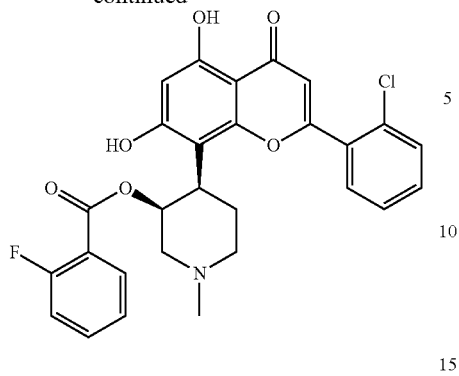

(3S, 4R)-4-(2-(2-chlorophenyl)-5,7-dihydroxy-4-oxo-4H-chromen-8-yl)-1-methylpiperidin-3-yl 2-fluorobenzoate To a stirred solution of 2-(2-chlorophenyl)-5,7-dihydroxy-8-((3S, 4R)-3-hydroxy-1-methylpiperidin-4-yl)-4H-chromen-4-one (0.3 g, 0.686 mmol, 1 eq) and 2-fluorobenzoic acid (0.116 g, 0.755 mmol, 1.1 eq) in dimethylformamide (10 mL) at 0° C., Triethylamine (0.32 mL, 2.051 mmol, 3.0 eq) and $T_3P$ (0.43 mL, 1.37 mmol, 2.0 eq) were added. The reaction mixture was stirred for 16 hours at room temperature. After confirming the reaction by TLC, the reaction mixture was concentrated. The crude residue obtained was purified by preparative HPLC to afford TFA salt of (3 S, 4R)-4-(2-(2-chlorophenyl)-5, 7-dihydroxy-4-oxo-4H-chromen-8-yl)-1-methylpiperidin-3-yl 2-fluorobenzoate as a light yellow solid (0.03 g, 11%). LC/MS m/z: 524.2 [M+H]$^+$; HPLC Purity: 99.59%; $^1$H NMR (400 MHz, DMSO-d$_6$) δ: 12.95 (s, 1H), 11.34 (s, 1H), 9.24 (s, 1H), 7.26-7.89 (m, 7H), 6.55 (s, 1H), 6.54 (s, 1H), 5.47 (s, 1H), 3.49-3.89 (m, 7H), 3.14-3.25 (m, 2H), 2.66-2.79 (m, 2H), 2.16 (d, J=13.20 Hz, 1H).

Example 24

Preparation of Compound 35

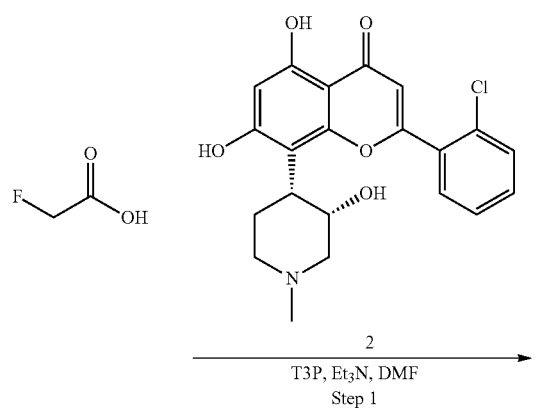

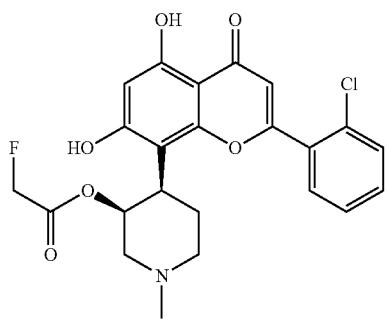

(3S, 4R)-4-(2-(2-chlorophenyl)-5,7-dihydroxy-4-oxo-4H-chromen-8-yl)-1-methylpiperidin-3-yl 2-fluoroacetate To a stirred solution of 2-(2-chlorophenyl)-5,7-dihydroxy-8-((3S, 4R)-3-hydroxy-1-methylpiperidin-4-yl)-4H-chromen-4-one (0.3 g, 0.686 mmol, 1 eq) and 2-fluoroacetic acid (0.068 g, 0.755 mmol, 1.1 eq) in dimethylformamide (10 mL) at 0° C., triethylamine (0.32 mL, 2.051 mmol, 3.0 eq) and $T_3P$ (0.43 mL, 1.37 mmol, 2.0 eq) were added. The reaction mixture was stirred for 16 hours at room temperature. After confirming the reaction by TLC, the reaction mixture was concentrated. The crude residue obtained was purified by preparative HPLC to afford TFA salt of (3 S, 4R)-4-(2-(2-chlorophenyl)-5, 7-dihydroxy-4-oxo-4H-chromen-8-yl)-1-methylpiperidin-3-yl 2-fluoroacetate as a yellow solid (0.21 g, 63%). LC/MS m/z: 462.2 [M+H]$^+$; HPLC Purity: 94.03%; $^1$H NMR (400 MHz, DMSO-d$_6$) δ: 12.99 (s, 1H), 11.39 (s, 1H), 9.52 (s, 1H), 7.57-7.80 (m, 4H), 6.57 (s, 1H), 6.36 (s, 1H), 5.23 (s, 1H), 4.79 (d, J=50.92 Hz, 2H), 3.03-3.19 (m, 7H), 2.75 (d, J=3.44 Hz, 3H), 1.97 (d, J=12.84 Hz, 1H).

Example 25

Preparation of Compounds 36 and 37

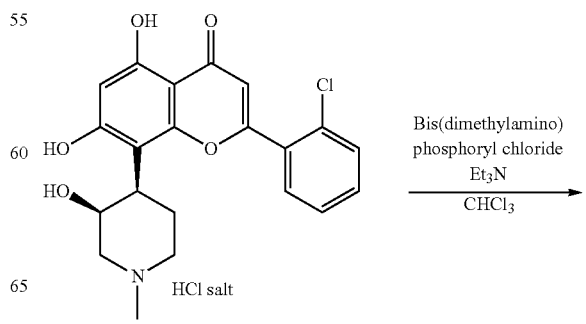

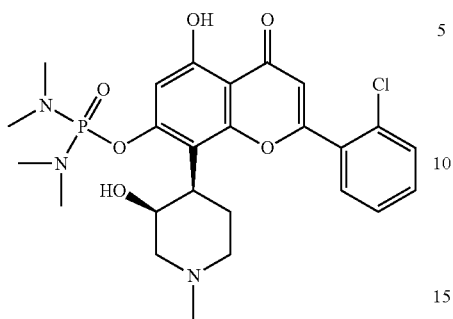

Compound 37

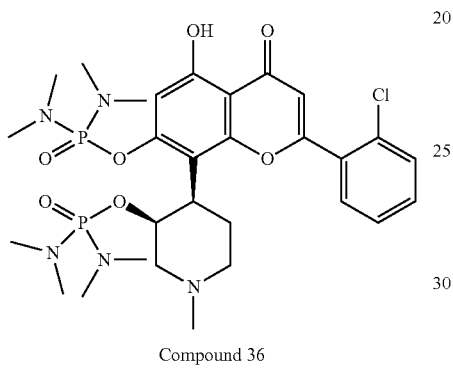

Compound 36

(3S,4R)-4-[7-{[bis(dimethylamino)phosphoryl]oxy}-2-(2-chlorophenyl)-5-hydroxy-4-oxo-4H-1-benzopyran-8-yl]-1-methylpiperidin-3-yl N,N,N',N'-tetramethylphosphorodiamidate (Compound 36) and 2-(2-chlorophenyl)-5-hydroxy-8-[(3S,4R)-3-hydroxy-1-methylpiperidin-4-yl]-4-oxo-4H-1-benzopyran-7-yl N,N,N',N'-tetramethylphosphorodiamidate (Compound 37)

To a solution of 2-(2-chlorophenyl)-5,7-dihydroxy-8-[(3S,4R)-3-hydroxy-1-methylpiperidin-4-yl]-4H-chromen-4-one hydrochloride (0.10 g), triethylamine (0.10 mL) and DMAP (4.0 mg) in chloroform (2.0 mL) was added bis(dimethylamino)phosphoryl chloride (35 μL) at 0° C. After being stirred for 18 hours at room temperature, the reaction mixture was concentrated under reduced pressure. The residue was purified by silica gel column chromatography (chloroform/methanol=100:0-86:14) to yield Compound 37 (49 mg) and Compound 36 (23 mg).

Compound 36:
LC/MS m/z: 670 [M+H]$^+$; $^1$H NMR (400 MHz, CDCl$_3$) δ: 1.68-1.78 (1H, m), 1.89-1.97 (1H, m), 2.11 (3H, s), 2.13 (3H, s), 2.22 (3H, s), 2.30 (1H, d, J=8.5 Hz), 2.52 (3H, s), 2.55 (3H, s), 2.61 (1H, d, J=10.4 Hz), 2.74 (3H, s), 2.77 (3H, s), 2.78 (3H, s), 2.81 (3H, s), 2.87-3.09 (2H, m), 3.26-3.37 (1H, m), 4.50 (1H, br s), 6.65 (1H, s), 6.92 (1H, s), 7.41-7.49 (2H, m), 7.56 (1H, d, J=9.2 Hz), 7.79 (1H, d, J=7.3 Hz), 12.97 (1H, s).

Compound 37:
LC/MS m/z: 536 [M+H]$^+$; $^1$H NMR (400 MHz, CDCl$_3$) δ: 1.51-1.78 (3H, m), 2.20-2.51 (4H, m), 2.77 (6H, s), 2.77 (6H, s), 3.00-3.28 (2H, m), 3.33-3.47 (1H, m), 4.01 (1H, br s), 6.55 (1H, s), 6.87 (1H, s), 7.35-7.44 (2H, m), 7.51 (1H, d, J=7.9 Hz), 7.74 (1H, br s), 12.90 (1H, s).

Example 26

Preparation of Compound 38

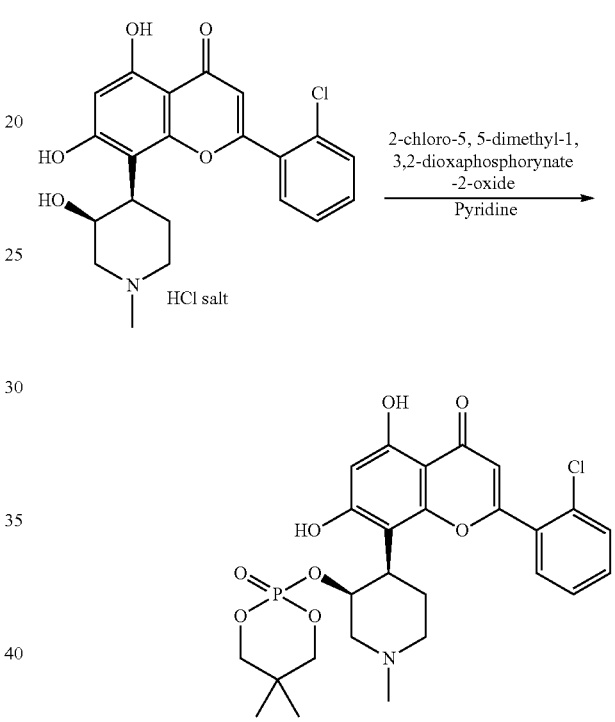

2-(2-chlorophenyl)-8-{(3S,4R)-3-[(5,5-dimethyl-2-oxo-1,3,2λ$^5$-dioxaphosphinan-2-yl)oxy]-1-methylpiperidin-4-yl}-5,7-dihydroxy-4H-1-benzopyran-4-one To a solution of 2-(2-chlorophenyl)-5,7-dihydroxy-8-[(3S,4R)-3-hydroxy-1-methylpiperidin-4-yl]-4H-chromen-4-one hydrochloride (0.10 g) in pyridine (3.0 mL) was added 2-chloro-5,5-dimethyl-1,3,2-dioxaphosphorynate-2-oxide (63 mg) at room temperature. The reaction mixture was stirred at room temperature for 1 hour and then at 50° C. for 2 hours. The reaction mixture was concentrated under reduced pressure. The residue was purified by silica gel column chromatography (chloroform/methanol=100:0-80:20) to yield Compound 38 (25 mg).

LC-MS m/z: 550 [M+H]$^+$; $^1$H NMR (400 MHz, DMSO-d$_6$) δ: 0.83 (3H, s), 1.22 (3H, s), 1.50-1.57 (1H, m), 1.81-1.89 (1H, m), 2.00-2.05 (1H, m), 2.12 (3H, s), 2.81-2.88 (2H, m), 3.17-3.23 (1H, m), 3.83 (1H, br s), 4.00-4.20 (2H, m), 4.26 (1H, d, J=11.0 Hz), 4.56 (1H, d, J=11.0 Hz), 4.60 (1H, br s), 6.74 (1H, s), 6.76 (1H, s), 7.55-7.66 (2H, m), 7.69-7.73 (1H, m), 7.87-7.90 (1H, m), 12.88 (1H, br s).

Example 27

Preparation of Compound 17

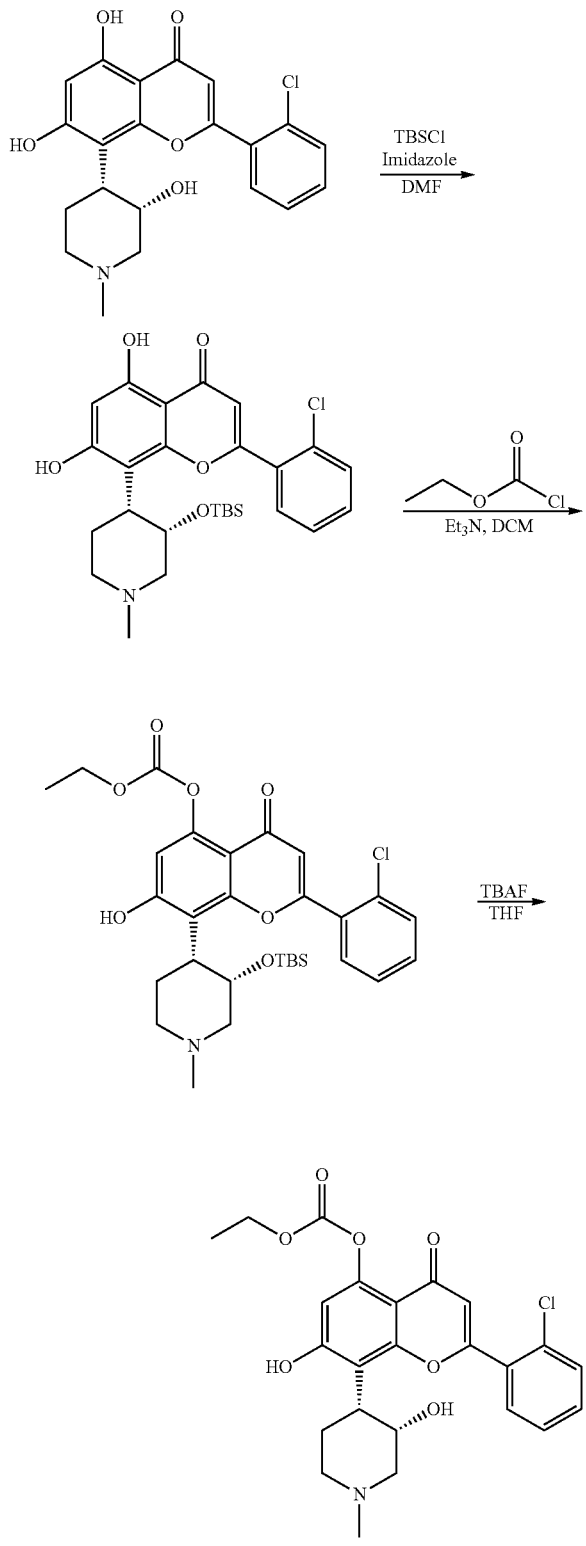

8-((3S, 4R)-3-((tert-butyldimethylsilyl)oxy)-1-methylpiperidin-4-yl)-2-(2-chlorophenyl)-5,7-dihydroxy-4H-chromen-4-one To a stirred solution of 2-(2-chlorophenyl)-5,7-dihydroxy-8-((3S, 4R)-3-hydroxy-1-methylpiperidin-4-yl)-4H-chromen-4-one (1 g, 2.28 mmol, 1.0 eq.) and imidazole (0.35 g, 4.36 mmol, 2 eq.) in dimithylformamide (10 ml) at 0° C., tert-Butyldimethylsilyl chloride (0.37 g, 2.28 mmol, 1.0 eq.) was added. The reaction mixture was stirred for 16 h at room temperature. After confirming the reaction by TLC, the solvent was evaporated under vacuum. The crude residue obtained was purified by preparative HPLC to afford 8-((3 S, 4R)-3-((tert-butyldimethylsilyl)oxy)-1-methylpiperidin-4-yl)-2-(2-chlorophenyl)-5,7-dihydroxy-4H-chromen-4-one as a yellow solid (0.5 g, 45%). LC/MS m/z: 516.2 [M+H]$^+$; HPLC Purity: 91.27%.

8-((3S, 4R)-3-((tert-butyldimethylsilyl)oxy)-1-methylpiperidin-4-yl)-2-(2-chlorophenyl)-7-hydroxy-4-oxo-4H-chromen-5-yl ethyl carbonate To a stirred solution of 8-((3S, 4R)-3-((tert-butyldimethylsilyl)oxy)-1-methylpiperidin-4-yl)-2-(2-chlorophenyl)-5,7-dihydroxy-4H-chromen-4-one (0.5 g, 0.970 mmol, 1.0 eq.) in dichloromethane (10 ml) at 0° C., triethylamine (0.41 ml, 2.8 mmol, 3.0 eq.) and ethylchloroformate (0.1 ml, 0.970 mmol, 1.0 eq.) were added dropwise. The reaction mixture was stirred for 6 h at room temperature. After confirming the reaction by TLC, the reaction mixture was quenched with ice cold water (20 ml) and extracted with dichloromethane (20 ml). The organic layer was dried over sodium sulphate the solvent was evaporated under vacuum. The crude residue obtained was lyophilized to afford 8-((3 S, 4R)-3-((tert-butyldimethyl silyl)oxy)-1-methylpiperidin-4-yl)-2-(2-chlorophenyl)-7-hydroxy-4-oxo-4H-chromen-5-yl ethyl carbonate as a yellow solid (0.45 g). LC/MS m/z: 588.2 [M+H]$^+$.

2-(2-chlorophenyl)-7-hydroxy-8-((3S, 4R)-3-hydroxy-1-methylpiperidin-4-yl)-4-oxo-4H-chromen-5-yl ethyl carbonate To a stirred solution of 8-((3 S, 4R)-3-((tert-butyldimethylsilyl)oxy)-1-methylpiperidin-4-yl)-2-(2-chlorophenyl)-7-hydroxy-4-oxo-4H-chromen-5-yl ethyl carbonate (0.45 g, 0.76 mmol, 1 eq.) in tetrahydrofuran (10 ml) at 0° C., Tetrabutylammonium fluoride (1.0 M in THF) (1.0 ml, 2 eq.) was added. The reaction mixture was stirred for 2 h at room temperature. After confirming the reaction by LCMS, the reaction mixture was concentrated. The crude residue obtained was purified by preparative HPLC to afford 2-(2-chlorophenyl)-7-hydroxy-8-((3 S, 4R)-3-hydroxy-1-methylpiperidin-4-yl)-4-oxo-4H-chromen-5-yl ethyl carbonate as a yellow solid (0.038 g, 12%). LC/MS m/z: 474 [M+H]$^+$; HPLC Purity: 99.50%; $^1$H NMR (400 MHz, DMSO-d$_6$) δ: 12.99 (s, 1H), 7.51-7.78 (m, 4H), 7.78 (s, 1H), 6.22 (d, J=10.28 Hz, 1H), 4.21-4.26 (m, 2H), 4.09 (s, 1H), 3.44-3.55 (m, 2H), 3.08-3.21 (m, 3H), 2.71-2.87 (m, 2H), 2.55-2.59 (m, 2H), 2.45-2.51 (m, 2H), 1.47 (d, J=13.80 Hz, 1H), 1.28-1.34 (m, 3H).

Example 28

Preparation of Compound 18

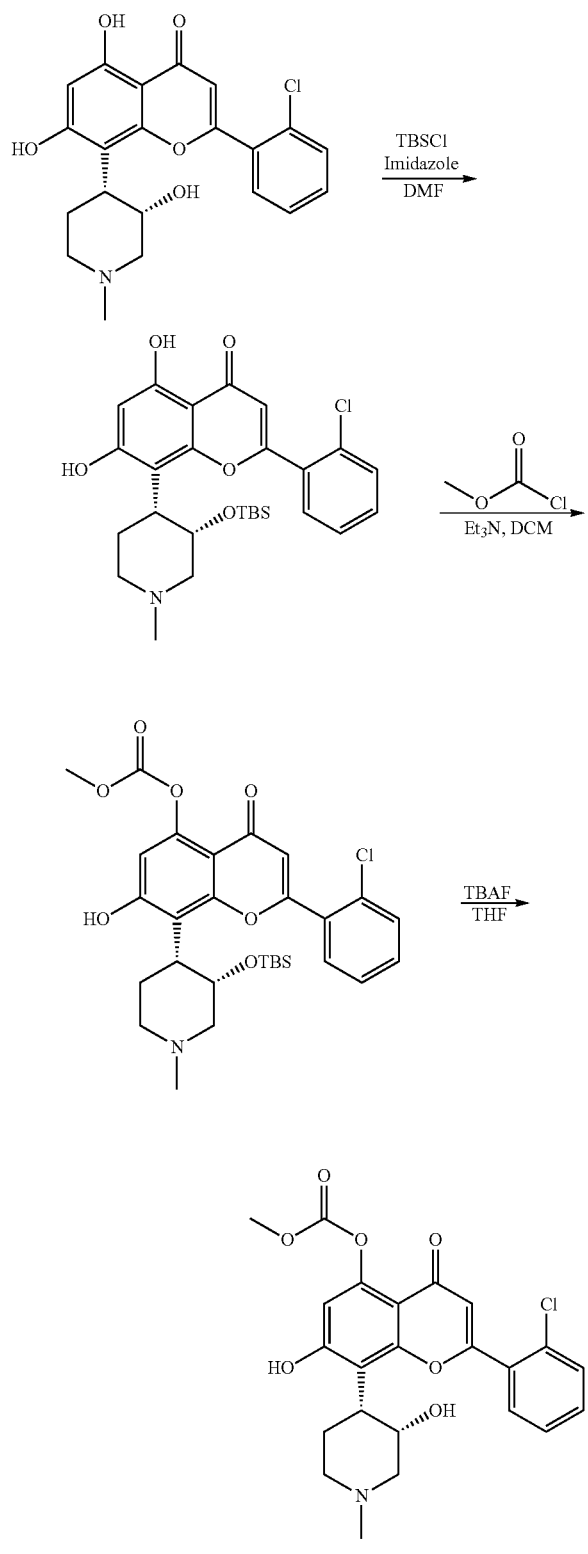

8-((3S, 4R)-3-((tert-butyldimethylsilyl)oxy)-1-methylpiperidin-4-yl)-2-(2-chlorophenyl)-5,7-dihydroxy-4H-chromen-4-one To a stirred solution of 2-(2-chlorophenyl)-5,7-dihydroxy-8-((3S, 4R)-3-hydroxy-1-methylpiperidin-4-yl)-4H-chromen-4-one (1 g, 2.28 mmol, 1.0 eq) and imidazole (0.35 g, 4.36 mmol, 2 eq) in dimethylformamide (10 mL) at 0° C., tert-Butyldimethylsilyl chloride (0.37 g, 2.28 mmol, 1.0 eq) was added. The reaction mixture was stirred for 16 hour at room temperature. After confirming the reaction by TLC, the solvent was evaporated under vacuum. The crude residue obtained was purified by preparative HPLC to afford 8-((3 S, 4R)-3-((tert-butyldimethylsilyl)oxy)-1-methylpiperidin-4-yl)-2-(2-chlorophenyl)-5,7-dihydroxy-4H-chromen-4-one as a yellow solid (0.5 g, 45%). LC/MS m/z: 516.2 [M+H]$^+$; HPLC Purity: 91.27%.

8-((3S, 4R)-3-((tert-butyldimethylsilyl)oxy)-1-methylpiperidin-4-yl)-2-(2-chlorophenyl)-7-hydroxy-4-oxo-4H-chromen-5-yl methyl carbonate To a stirred solution of 8-((3S, 4R)-3-((tert-butyldimethylsilyl)oxy)-1-methylpiperidin-4-yl)-2-(2-chlorophenyl)-5,7-dihydroxy-4H-chromen-4-one (0.5 g, 0.970 mmol, 1.0 eq.) in dichloromethane (10 ml) at 0° C., triethylamine (0.41 ml, 2.8 mmol, 3.0 eq.) and methyl chloroformate (0.09 ml, 0.970 mmol, 1.0 eq.) were added dropwise. The reaction mixture was stirred for 6 h at room temperature. After confirming the reaction by TLC, the reaction mixture was quenched with ice cold water (20 ml) and extracted with dichloromethane (20 ml). The organic layer was dried over sodium sulphate and the solvent was evaporated under vacuum. The crude residue obtained was lyophilized to 8-((3 S, 4R)-3-((tert-butyldimethylsilyl)oxy)-1-methylpiperidin-4-yl)-2-(2-chlorophenyl)-7-hydroxy-4-oxo-4H-chromen-5-yl methyl carbonate as a yellow solid (0.4 g).

2-(2-chlorophenyl)-7-hydroxy-8-((3S, 4R)-3-hydroxy-1-methylpiperidin-4-yl)-4-oxo-4H-chromen-5-yl methyl carbonate To a stirred solution of 8-((3 S, 4R)-3-((tert-butyldimethylsilyl)oxy)-1-methylpiperidin-4-yl)-2-(2-chlorophenyl)-7-hydroxy-4-oxo-4H-chromen-5-yl methyl carbonate (0.4 g, 0.69 mmol, 1 eq.) in tetrahydrofuran (10 ml) at 0° C., Tetrabutylammonium fluoride (1.0 M in THF) (1.0 ml, 2 eq.) was added. The reaction mixture was stirred for 2 h at room temperature. After confirming the reaction by LCMS, the reaction mixture was concentrated. The crude residue obtained was purified by preparative HPLC to afford 2-(2-chlorophenyl)-7-hydroxy-8-((3 S, 4R)-3-hydroxy-1-methylpiperidin-4-yl)-4-oxo-4H-chromen-5-yl methyl carbonate as a yellow solid (0.048 g, 16%). LC/MS m/z: 460.0 [M+H]$^+$; HPLC Purity: 96.19%; $^1$H NMR (400 MHz, DMSO-d$_6$) δ: 12.99 (s, 1H), 7.49-7.73 (m, 4H), 6.11 (s, 1H), 6.03 (s, 1H), 4.07 (s, 1H), 3.76 (s, 3H), 2.88-3.12 (m, 4H), 3.08-3.21 (m, 3H), 2.66-0.00 (m, 3H), 1.00 (d, J=12.80 Hz, 1H).

Example 29

Preparation of Compound 19

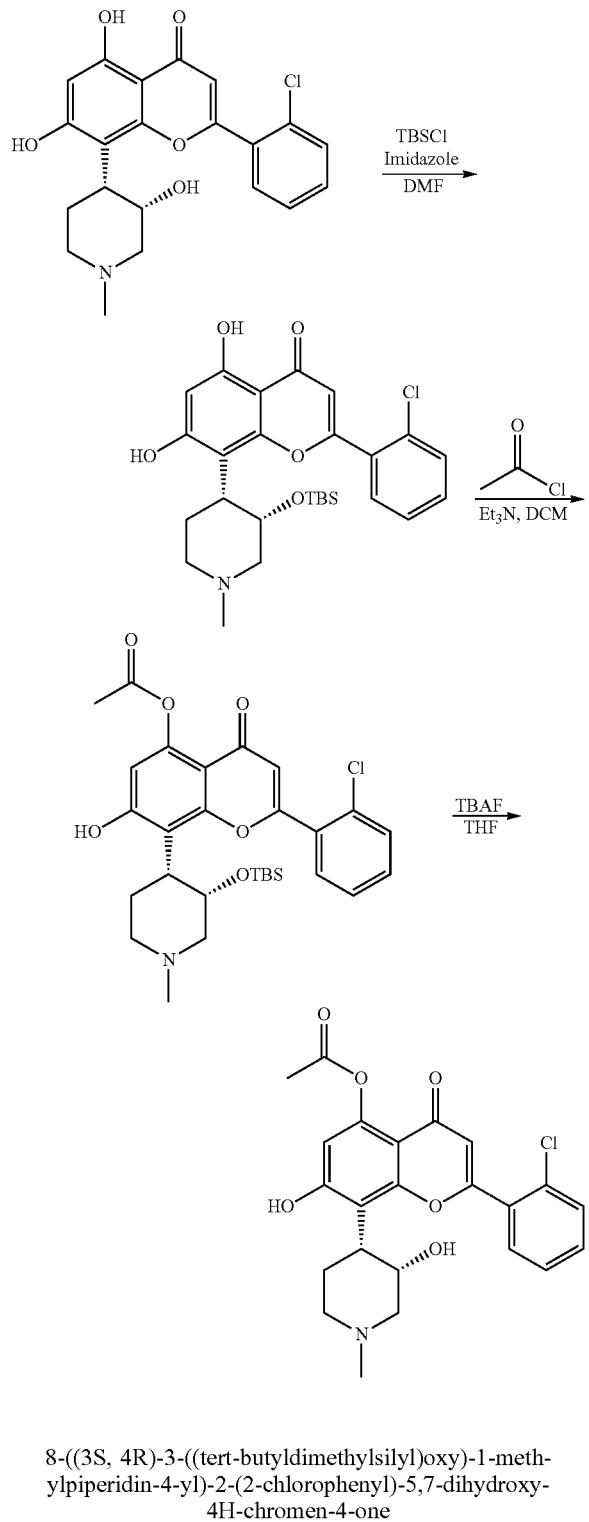

8-((3S, 4R)-3-((tert-butyldimethylsilyl)oxy)-1-methylpiperidin-4-yl)-2-(2-chlorophenyl)-5,7-dihydroxy-4H-chromen-4-one To a stirred solution of 2-(2-chlorophenyl)-5,7-dihydroxy-8-((3S, 4R)-3-hydroxy-1-methylpiperidin-4-yl)-4H-chromen-4-one (2 g, 4.57 mmol, 1.0 eq) and imidazole (0.70 g, 8.72 mmol, 2 eq) in dimethylformamide (20 mL) at 0° C., tert-Butyldimethylsilyl chloride (0.74 g, 2.28 mmol, 1.0 eq) was added. The reaction mixture was stirred for 16 hours at room temperature. After confirming the reaction by TLC, the solvent was evaporated under vacuum. The crude residue obtained was purified by preparative HPLC to afford 8-((3 S, 4R)-3-((tert-butyldimethylsilyl)oxy)-1-methylpiperidin-4-yl)-2-(2-chlorophenyl)-5,7-dihydroxy-4H-chromen-4-one as a yellow solid (1.6 g, 69%). LC/MS m/z: 514.0 [M−H]⁻; HPLC Purity: 99.38%.

8-((3S, 4R)-3-((tert-butyldimethylsilyl)oxy)-1-methylpiperidin-4-yl)-2-(2-chlorophenyl)-7-hydroxy-4-oxo-4H-chromen-5-yl acetate To a stirred solution of 8-((3 S, 4R)-3-((tert-butyldimethylsilyl)oxy)-1-methylpiperidin-4-yl)-2-(2-chlorophenyl)-5,7-dihydroxy-4H-chromen-4-one (0.8 g, 1.55 mmol, 1.0 eq.) in dichloromethane (10 ml) at 0° C., triethylamine (0.65 ml, 4.66 mmol, 3.0 eq.) and acetyl chloride (0.132 ml, 1.86 mmol, 1.0 eq.) were added dropwise. The reaction mixture was stirred for 6 h at room temperature. After confirming the reaction by TLC, the reaction mixture was quenched with ice cold water (20 ml) and extracted with dichloromethane (20 ml). The organic layer was dried over sodium sulphate the solvent was evaporated under vacuum. The crude residue obtained was lyophilized to afford 8-((3 S, 4R)-3-((tert-butyldimethyl silyl)oxy)-1-methylpiperidin-4-yl)-2-(2-chlorophenyl)-7-hydroxy-4-oxo-4H-chromen-5-yl acetate as a yellow solid (0.6 g). LC/MS m/z: 558.0 [M+H]⁺.

2-(2-chlorophenyl)-7-hydroxy-8-((3S, 4R)-3-hydroxy-1-methylpiperidin-4-yl)-4-oxo-4H-chromen-5-yl acetate To a stirred solution of 8-((3 S, 4R)-3-((tert-butyldimethylsilyl)oxy)-1-methylpiperidin-4-yl)-2-(2-chlorophenyl)-7-hydroxy-4-oxo-4H-chromen-5-yl acetate (0.6 g, 1.077 mmol, 1 eq.) in tetrahydrofuran (10 ml) at 0° C., Tetrabutylammonium fluoride (1.0 M in THF) (1.5 ml, 2 eq.) was added. The reaction mixture was stirred for 2 h at room temperature. After confirming the reaction by LCMS, the reaction mixture was concentrated. The crude residue obtained was purified by preparative HPLC to afford 2-(2-chlorophenyl)-7-hydroxy-8-((3 S, 4R)-3-hydroxy-1-methylpiperidin-4-yl)-4-oxo-4H-chromen-5-yl acetate as a yellow solid (0.022 g, 11%). LC/MS m/z: 442.0 [M−H]⁻; HPLC Purity: 97.82%; ¹H NMR (400 MHz, DMSO-d₆) δ: 12.97 (s, 1H), 7.53-7.78 (m, 4H), 6.31 (s, 1H), 6.24 (s, 1H), 4.12 (s, 1H), 3.48-3.52 (m, 1H), 3.29 (s, 2H), 2.98-3.19 (m, 4H), 2.70 (s, 3H), 2.26 (s, 3H), 1.66 (d, J=5.60 Hz, 2H).

Example 30

Preparation of Compound 20

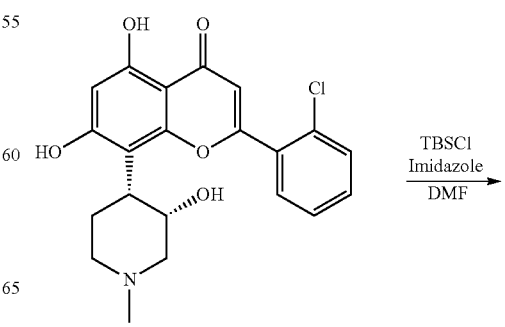

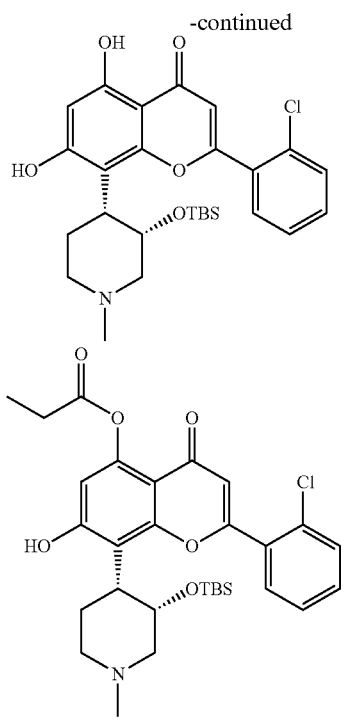

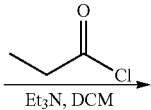

8-((3S, 4R)-3-((tert-butyldimethylsilyl)oxy)-1-methylpiperidin-4-yl)-2-(2-chlorophenyl)-5,7-dihydroxy-4H-chromen-4-one To a stirred solution of 2-(2-chlorophenyl)-5,7-dihydroxy-8-((3S, 4R)-3-hydroxy-1-methylpiperidin-4-yl)-4H-chromen-4-one (2 g, 4.57 mmol, 1.0 eq) and 5 imidazole (0.70 g, 8.72 mmol, 2 eq) in dimithylformamide (20 mL) at 0° C., tert-Butyldimethylsilyl chloride (0.74 g, 2.28 mmol, 1.0 eq) was added. The reaction mixture was stirred for 16 hours at room temperature. After confirming the reaction by TLC, the solvent was evaporated under vacuum. The crude residue obtained was purified by preparative HPLC to afford 8-((3 S, 4R)-3-((tert-butyldimethylsilyl)oxy)-1-methylpiperidin-4-yl)-2-(2-chlorophenyl)-5,7-dihydroxy-4H-chromen-4-one as a yellow solid (1.6 g, 69%). LC/MS m/z: 514.0 [M−H]⁻; HPLC Purity: 99.38%.

8-((3S, 4R)-3-((tert-butyldimethylsilyl)oxy)-1-methylpiperidin-4-yl)-2-(2-chlorophenyl)-7-hydroxy-4-oxo-4H-chromen-5-yl propionate To a stirred solution of 8-((3 S, 4R)-3-((tert-butyldimethylsilyl)oxy)-1-methylpiperidin-4-yl)-2-(2-chlorophenyl)-5, 7-dihydroxy-4H-chromen-4-one (0.8 g, 1.55 mmol, 1.0 eq.) in dichloromethane (10 ml) at 0° C., triethylamine (0.65 ml, 4.66 mmol, 3.0 eq.) and propionyl chloride (0.162 ml, 1.86 mmol, 1.2 eq.) were added dropwise. The reaction mixture was stirred for 6 h at room temperature. After confirming the reaction by TLC, the reaction mixture was quenched with ice cold water (20 ml) and extracted with dichloromethane (20 ml). The organic layer was dried over sodium sulphate and the solvent was evaporated under vacuum. The crude residue obtained was lyophilized to afford 8-((3S, 4R)-3-((tert-butyldimethylsilyl)oxy)-1-methylpiperidin-4-yl)-2-(2-chlorophenyl)-7-hydroxy-4-oxo-4H-chromen-5-yl propionate as a yellow solid (0.68 g). LC/MS m/z: 570.1 [M−H]⁻.

2-(2-chlorophenyl)-7-hydroxy-8-((3S, 4R)-3-hydroxy-1-methylpiperidin-4-yl)-4-oxo-4H-chromen-5-yl propionate To a stirred solution of 8-((3 S, 4R)-3-((tert-butyldimethylsilyl)oxy)-1-methylpiperidin-4-yl)-2-(2-chlorophenyl)-7-hydroxy-4-oxo-4H-chromen-5-yl propionate (0.8 g, 1.40 mmol, 1 eq.) in tetrahydrofuran (10 ml) at 0° C., Tetrabutylammonium fluoride (1.0 M in THF) (1.6 ml, 2 eq.) was added. The reaction mixture was stirred for 2 h at room temperature. After confirming the reaction by LCMS, the reaction mixture was concentrated. The crude residue obtained was purified by preparative HPLC to afford 2-(2-chlorophenyl)-7-hydroxy-8-((3 S, 4R)-3-hydroxy-1-methylpiperidin-4-yl)-4-oxo-4H-chromen-5-yl propionate as a yellow solid (0.07 g, 12%). LC/MS m/z: 458.0 [M−H]⁻;
HPLC Purity:
99.24%; 1H NMR (400 MHz, DMSO-$d_6$) δ: 12.97 (s, 1H), 7.52-7.77 (m, 4H), 6.24 (s, 1H), 6.25 (s, 1H), 4.12 (s, 1H), 3.46-3.51 (m, 2H), 3.24-3.33 (m, 3H), 2.96-3.12 (m, 3H), 2.69 (s, 3H), 2.58-2.64 (m, 2H), 1.63 (d, J=9.60 Hz, 1H), 1.12-1.16 (m, 3H).

Example 31

Pharmacokinetic Testing of Representative Compounds

Representative compounds were tested for pharmacokinetic activity in CD-1 mice. Mice were dosed orally with 10 mg/kg of each representative compound as well as alvocidib. The results of the study are shown in Table 3:

TABLE 3

Pharmacokinetic Results for Prodrug Compounds Compared to Alvocidib

| Analyte | Compound 39 | Alvocidib | Compound 40 | Alvocidib |
|---|---|---|---|---|
| $C_{max}$ (ng/mL or ng/G) | nd† | 1570.5 ± 403.6 | nd | 1256.2 ± 113.9 |
| $T_{max}$ (h) | nd | 0.5 ± 0.0 | nd | 0.5 ± 0.0 |

TABLE 3-continued

Pharmacokinetic Results for Prodrug Compounds Compared to Alvocidib

| | | | | |
|---|---|---|---|---|
| $AUC_{Last}$ (ng · h/mL) or (ng · h/G) | nd | 8341.8 ± 318.7 | nd | 4277.7 ± 256.1 |
| $AUC_{0 \to \infty}$ (ng · h/mL) or (ng · h/G) | nd | 8768.8 ± 378.0 | nd | 4391.1 ± 277.0 |
| Half Life (h) | nd | 5.3 ± 0.4 | nd | 4.4 ± 0.4 |

| Analyte | Compound 41 | Alvocidib | Compound 42 | Alvocidib |
|---|---|---|---|---|
| $C_{max}$ (ng/mL or ng/G) | nd | 1167.5 ± 116.9 | nd | 1591.9 ± 205.6 |
| $T_{max}$ (h) | nd | 0.6 ± 0.4 | nd | 0.4 ± 0.1 |
| $AUC_{Last}$ (ng · h/mL) or (ng · h/G) | nd | 8352.1 ± 2700.7 | nd | 6564.9 ± 765.6 |
| $AUC_{0 \to \infty}$ (ng · h/mL) or (ng · h/G) | nd | nd | nd | 6767.7 ± 757.6 |
| Half Life (h) | nd | nd | nd | 4.8 ± 0.3 |

Note:
Results are expressed as Mean ± Standard Deviation
[†]none detected

The results in Table 3 show the tested compounds afforded high exposure of released alvocidib and no apparent exposure of the prodrug compounds. Additional results are shown in Tables 4 and 5, including use of alvocidib.HCl as a control:

TABLE 4

Pharmacokinetic Results for Prodrug Compounds

| Analyte | Alvocidib•HCl | Compound 10 | Alvocidib | Compound 11 | Alvocidib |
|---|---|---|---|---|---|
| $C_{max}$ (ng/mL or ng/G) | 1632.4 ± 274.7 | 198.1 ± 27.2 | 64.9 ± 12.4 | 206.4 ± 11.7 | 38.8 ± 3.1 |
| $T_{max}$ (h) | 0.25 ± 0.0 | 0.25 ± 0.0 | 0.42 ± 0.14 | 0.25 ± 0.0 | 0.42 ± 0.14 |
| $AUC_{Last}$ (ng · h/mL) or (ng · h/G) | 7275.2 ± 2572.2 | 405.4 ± 215.6 | 376.2 ± 122.5 | 238.3 ± 43.9 | 150.1 ± 70.8 |
| $AUC_{0 \to \infty}$ (ng · h/mL) or (ng · h/G) | 10,933.3 ± 4498.0 | 646.8 ± 219.4 | 393.9 ± 128.0 | 275.1 ± 24.1 | 174.5 ± 49.0 |
| Half Life (h) | 16.0 ± 9.8 | 3.8 ± 0.6 | 5.2 ± 0.6 | 4.2 ± 0.1 | 5.5 ± 1.1 |

| | Alvocidib•HCl | Compound 12 | Alvocidib | Compound 13 | Alvocidib |
|---|---|---|---|---|---|
| $C_{max}$ (ng/mL or ng/G) | 1632.4 ± 274.7 | 131.1 ± 15.5 | 8.1 ± 0.9 | 248.4 ± 23.4 | 9.5 ± 1.1 |
| $T_{max}$ (h) | 0.25 ± 0.0 | 0.42 ± 0.1 | 0.42 ± 0.1 | 0.4 ± 0.1 | 0.4 ± 0.1 |
| $AUC_{Last}$ (ng · h/mL) or (ng · h/G) | 7275.2 ± 2572.2 | 262.2 ± 27.8 | 18.5 ± 3.1 | 594.7 ± 143.7 | 31.9 ± 10.2 |
| $AUC_{0 \to \infty}$ (ng · h/mL) or (ng · h/G) | 10,933.3 ± 4498.0 | 281.4 ± 28.3 | 22.7 ± 3.2 | 620.2 ± 147.7 | 50.9 ± 13.6 |
| Half Life (h) | 16.0 ± 9.8 | 2.1 ± 0.1 | 3.1 ± 0.6 | 2.0 ± 0.8 | 7.7 ± 4.5 |

Note:
Results are expressed as Mean ± Standard Deviation

TABLE 5

Pharmacokinetic Results for Prodrug Compounds

| Analyte | Alvocidib•HCl | Compound 3 | Alvocidib |
|---|---|---|---|
| $C_{max}$ (ng/mL or ng/G) | 2379.5 ± 786.3 | nd[†] | 755.6 ± 44.3 |
| $T_{max}$ (h) | 0.33 ± 0.14 | nd | 1.0 ± 0.0 |
| $AUC_{Last}$ (ng·h/mL) or (ng·h/G) | 9952.7 ± 1769.5 | nd | 5277 ± 268.2 |
| $AUG_{0\to\infty}$ (ng·h/mL) or (ng·h/G) | 10,603.8 ± 1968.4 | nd | 5603.5 ± 13.6 |
| Half Life (h) | 6.1 ± 0.4 | nd | 5.9 ± 1.2 |

Note:
Results are expressed as Mean ± Standard Deviation
[†]none detected
Compound 3 showed no apparent exposure.

Example 32

Comparison of Exposure of Released Alvocidib to Representative Prodrug Compounds Representative prodrug compounds (i.e., Compounds 10, 21-28 and 29-31) were tested to determine the resultant exposure of released alvocidib as well exposure of the parent compound. The exposure of the parent prodrug is expressed as a percentage of the released alvocidib exposure (% F). The released alvocidib exposure (% F) for each prodrug was calculated as a percentage of the exposure of alvocidib, dosed orally at an equivalent dose.

Figure 1B:
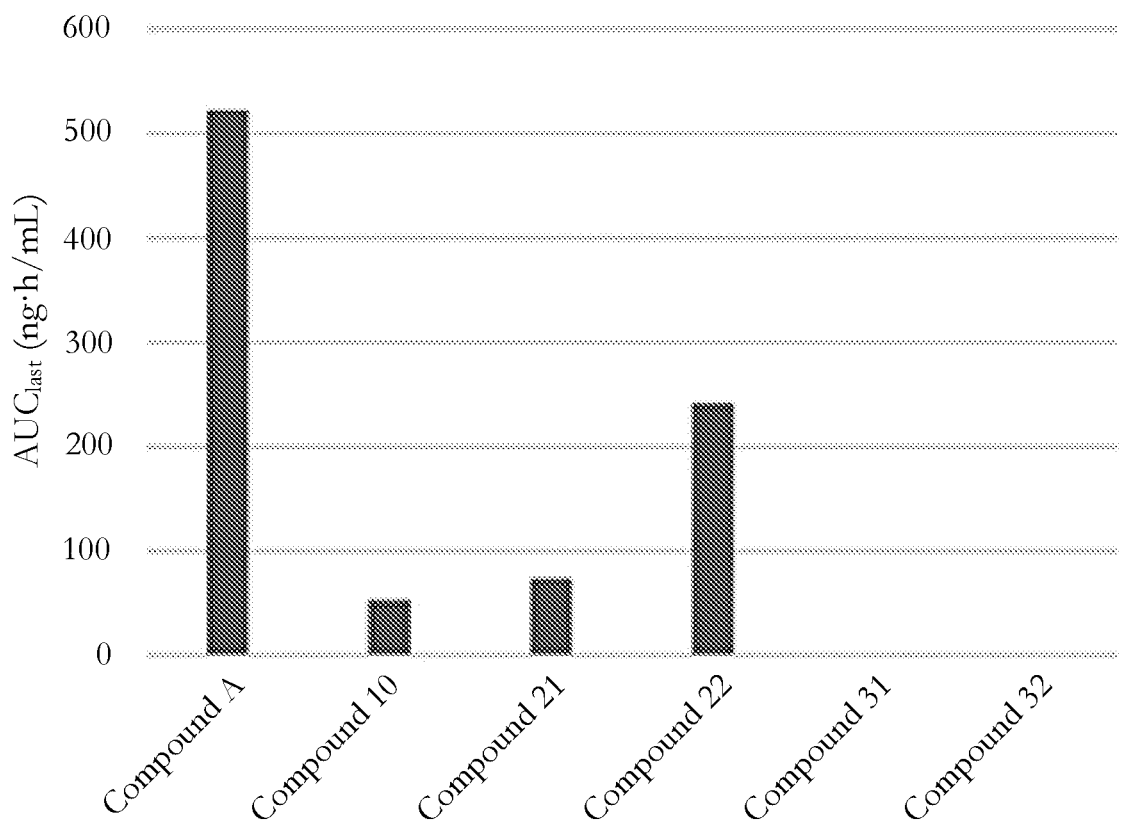

The released alvocidib and the parent prodrug exposure data generated for Compounds A, 10, 21, 22, 31 and 32 are shown in FIGS. 1A and 1B, respectively. Compounds 10, 21 and 32 had an exposure of alvocidib greater than 30% F. Exposure of the parent prodrug was 2% and 3% for Compounds 10 and 22, respectively, while exposure of the parent prodrug of Compounds 31 and 32 was not detected.

Figure 2A:
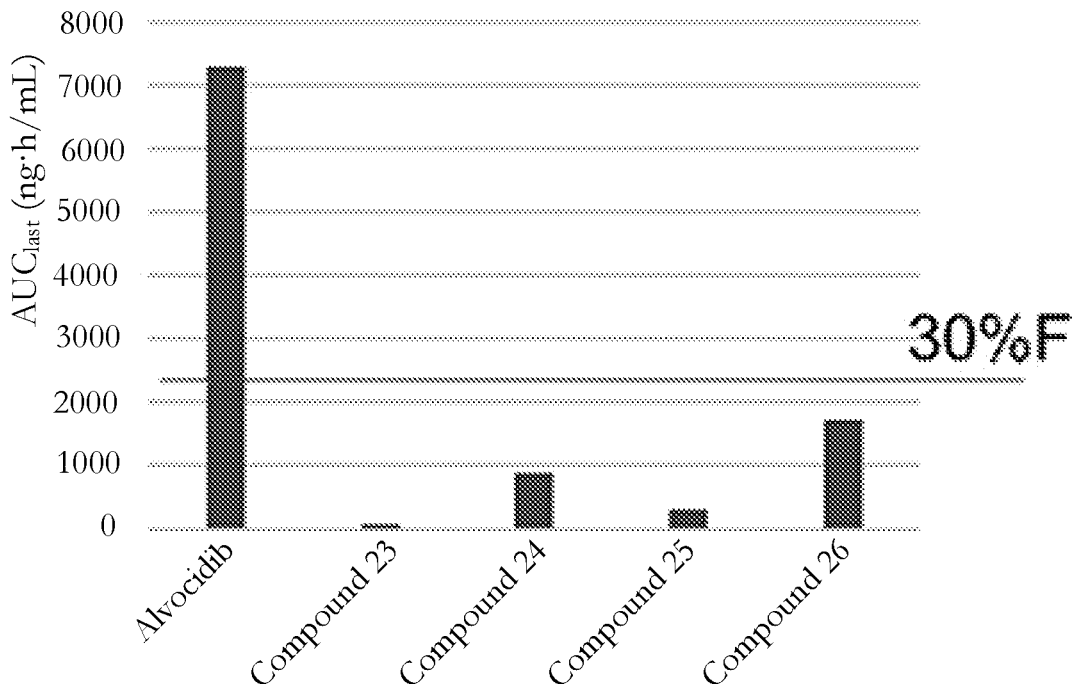
Figure 2B:
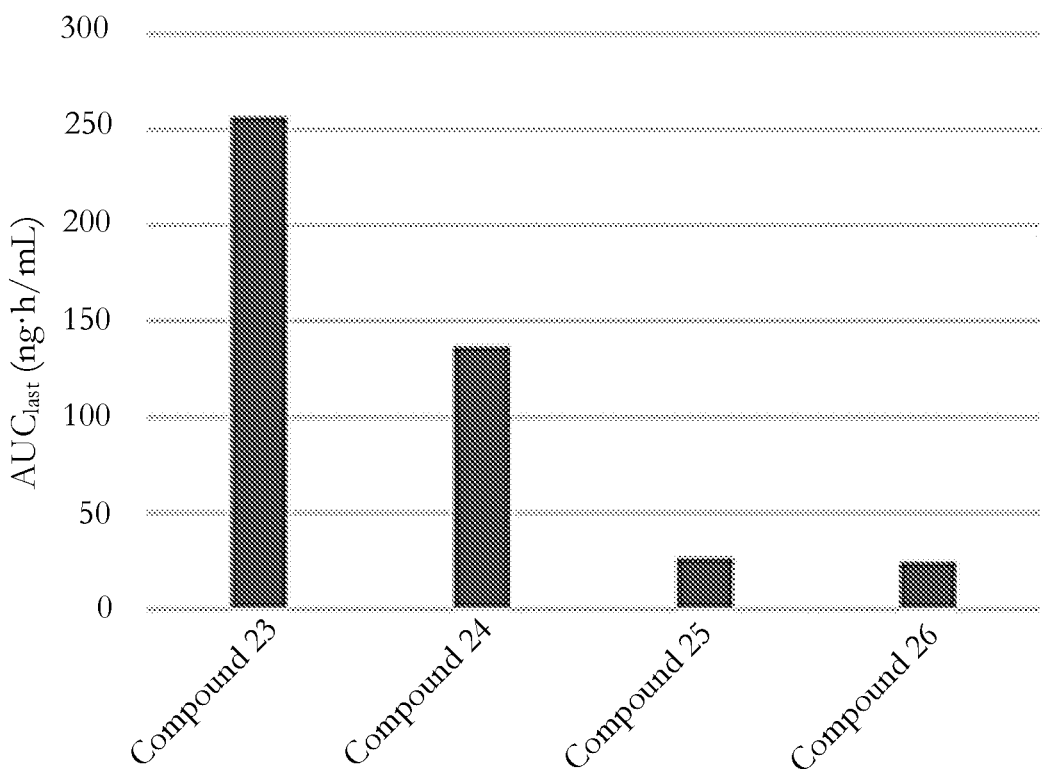
Figure 3A:
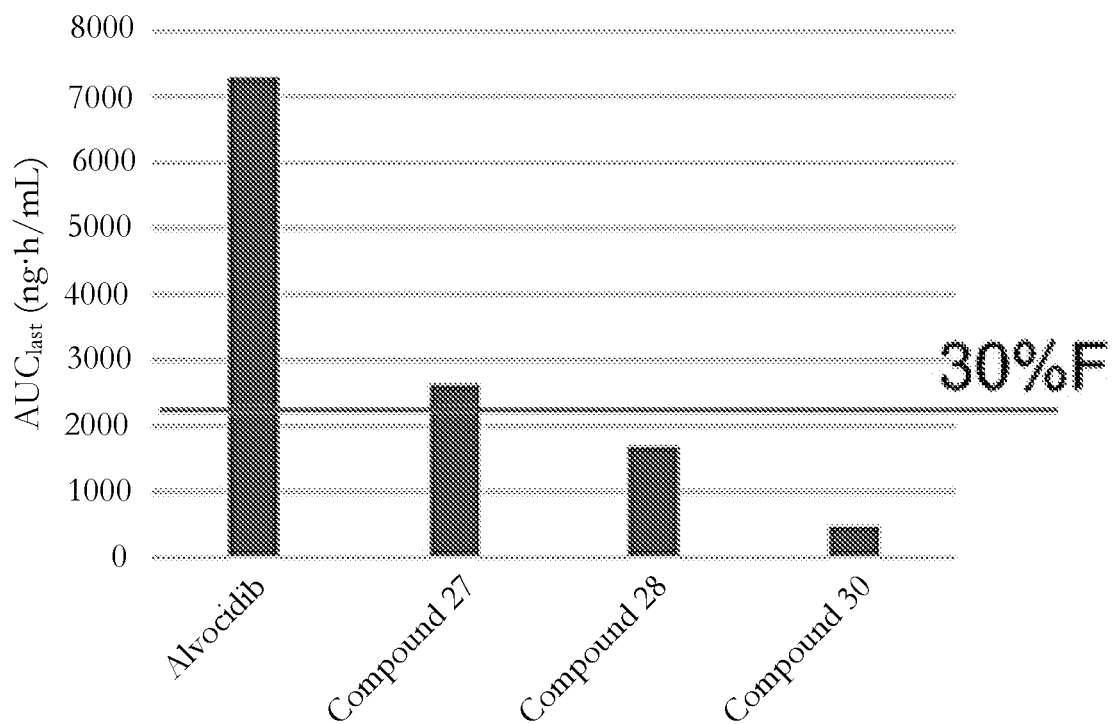
Figure 3B:
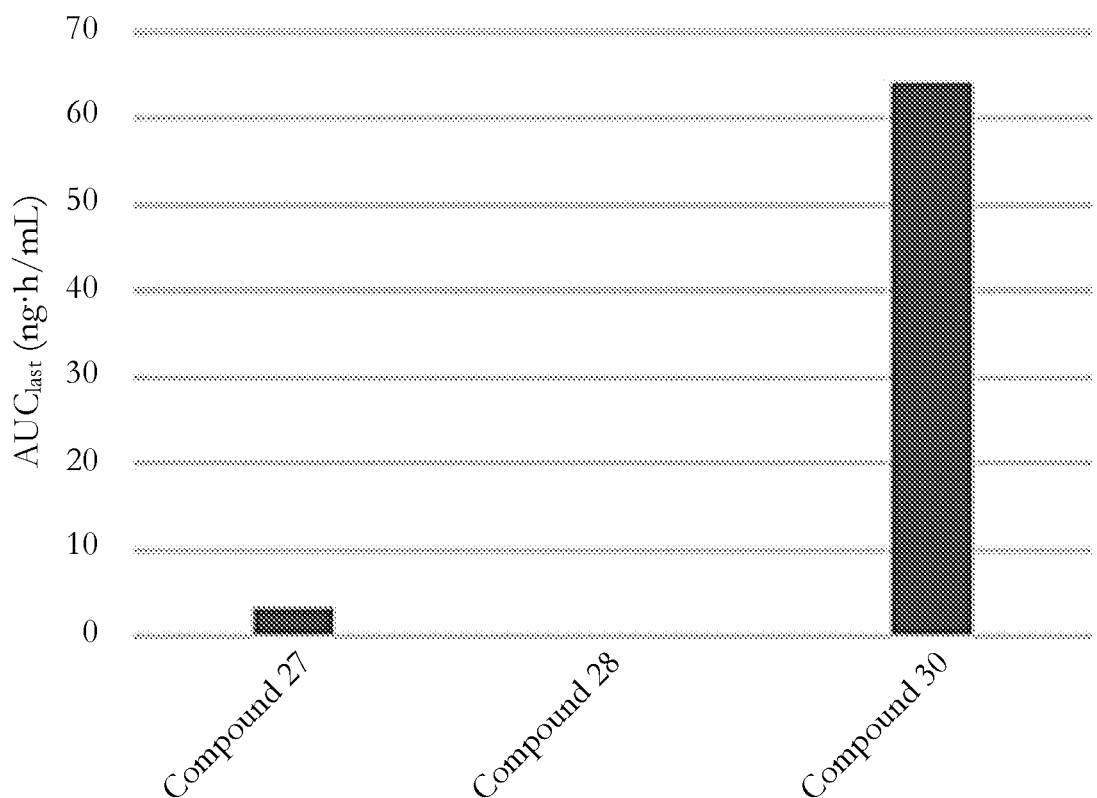

The same data for Compounds 23-26 is shown in FIGS. 2A and 2B and the data for Compounds 27, 28 and 30 is shown in FIGS. 3A and 3B. Compound 27 provided exposure of alvocidib greater than 30% F with low exposure of the parent prodrug compound. Exposure of the parent prodrug of Compound 28 was not detected.

All of the U.S. patents, U.S. patent application publications, U.S. patent applications, foreign patents, foreign patent applications and non-patent publications referred to in this specification, including U.S. Provisional Patent Application No. 62/424,255, filed Nov. 18, 2016, to which the present application claims priority, are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound having one of the following structures:

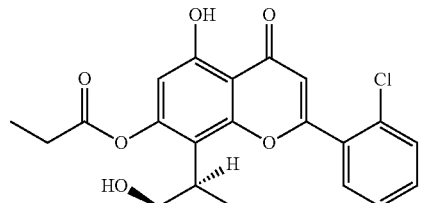
;

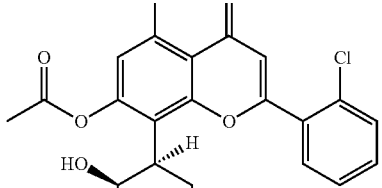
;

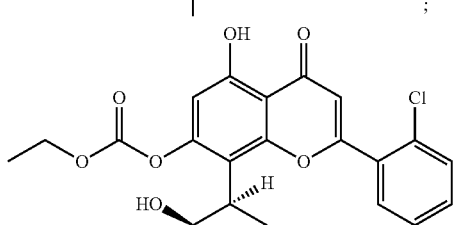
;

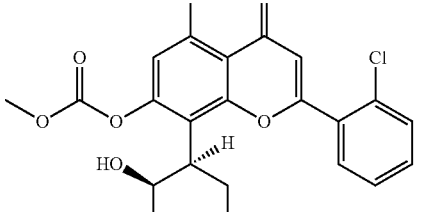
;

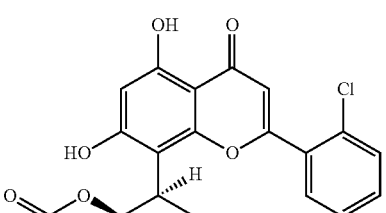
;

109
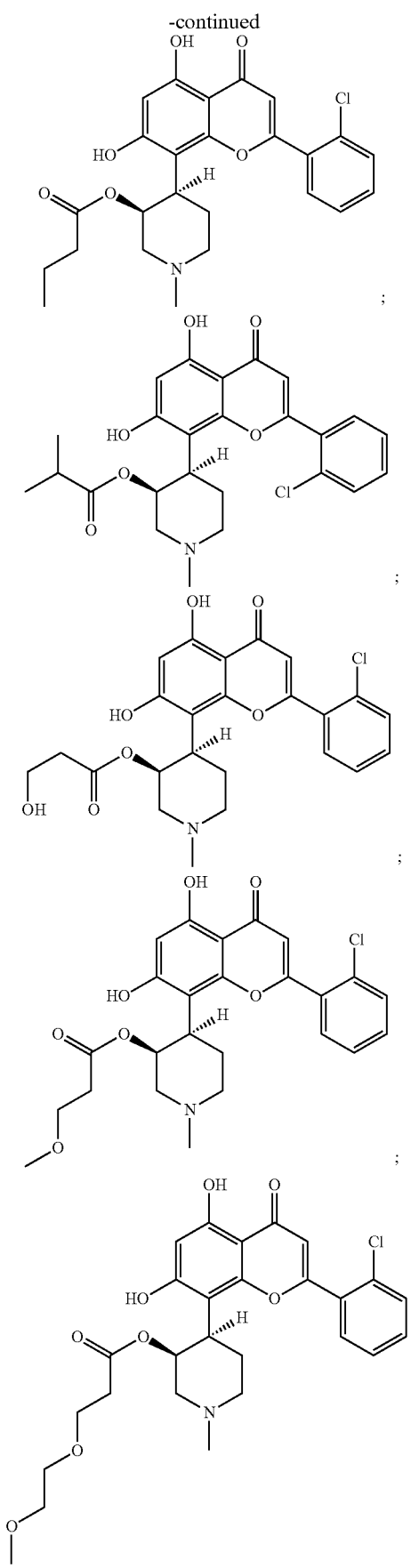
110
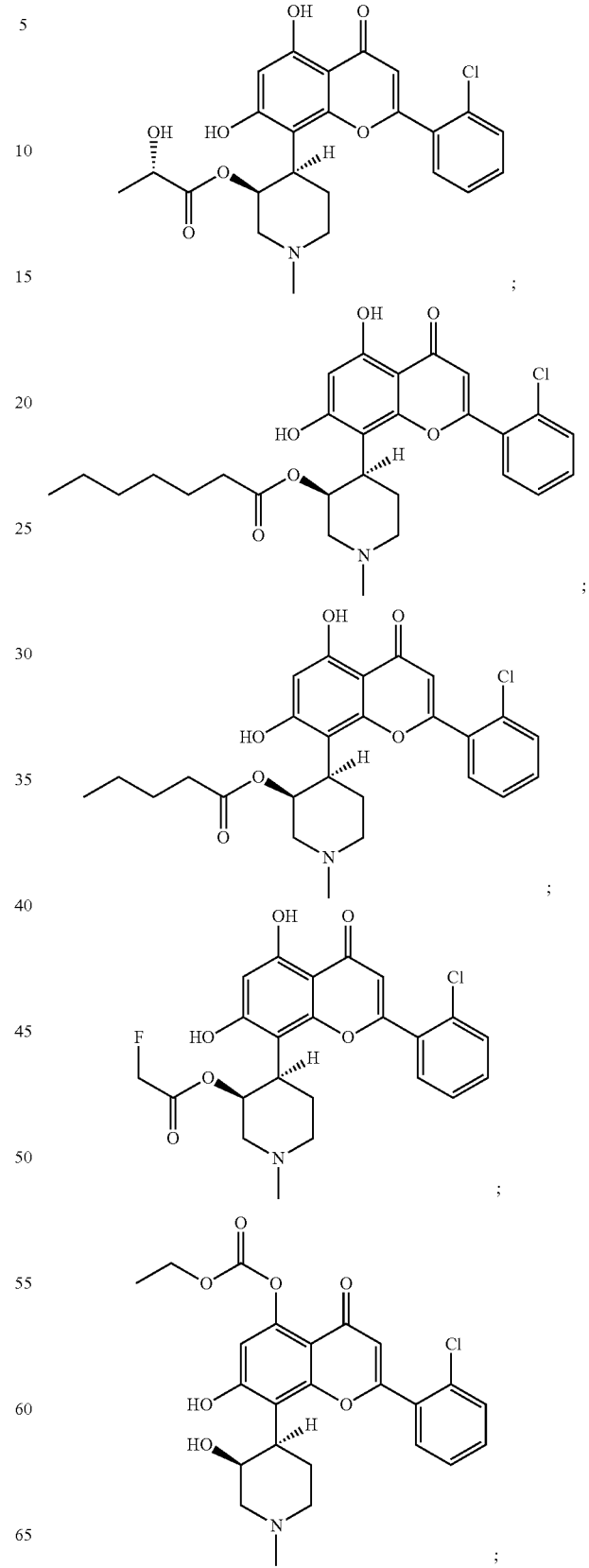

111
-continued

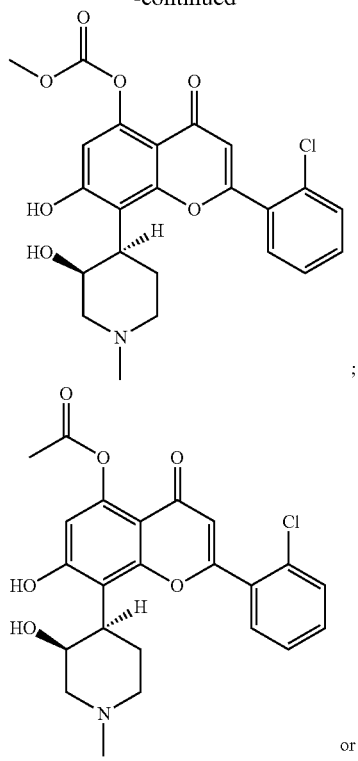

112
-continued

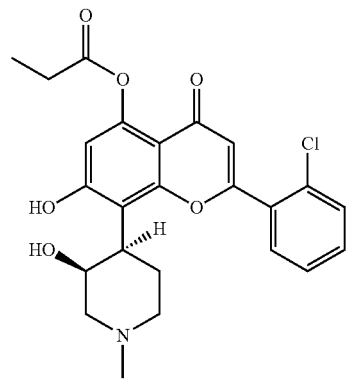

or a pharmaceutically acceptable salt thereof.

2. A pharmaceutically acceptable salt of a compound of claim 1.

3. A pharmaceutical composition comprising a pharmaceutically acceptable carrier or excipient, and a compound of claim 1, or a pharmaceutically acceptable salt thereof.

4. The pharmaceutical composition of claim 3, wherein the pharmaceutical composition is formulated for oral delivery.

* * * * *